US008252555B2

(12) United States Patent
Zelder et al.

(10) Patent No.: US 8,252,555 B2
(45) Date of Patent: Aug. 28, 2012

(54) NUCLEIC ACID ENCODING A COBALAMIN-DEPENDENT METHIONINE SYNTHASE POLYPEPTIDE

(75) Inventors: Oskar Zelder, Speyer (DE); Wolfgang Grabarse, Mannheim (DE); Corinna Klopprogge, Mannheim (DE); Hartwig Schröder, Nuβloch (DE); Stefan Haefner, Speyer (DE); Anja Knietsch, Unna (DE); Andrea Herold, Ketsch (DE)

(73) Assignee: Evonik Degussa AG, Essen (DE)

( * ) Notice: Subject to any disclaimer, the term of this patent is extended or adjusted under 35 U.S.C. 154(b) by 134 days.

(21) Appl. No.: 12/521,141

(22) PCT Filed: Dec. 21, 2007

(86) PCT No.: PCT/EP2007/064471

§ 371 (c)(1), (2), (4) Date: Jun. 25, 2009

(87) PCT Pub. No.: WO2008/080900

PCT Pub. Date: Jul. 10, 2008

(65) Prior Publication Data

US 2010/0035307 A1 Feb. 11, 2010

(30) Foreign Application Priority Data

Dec. 29, 2006 (EP) .................................... 06127363

(51) Int. Cl.
*C12P 21/06* (2006.01)

(52) U.S. Cl. ........ 435/69.1; 435/113; 435/7.1; 435/252; 435/320.1

(58) Field of Classification Search ........................ None
See application file for complete search history.

(56) References Cited

U.S. PATENT DOCUMENTS 7,884,066 B2 * 2/2011 Ting ............................... 514/1.1
7,884,069 B2 * 2/2011 Schaebitz et al. ............ 424/85.1
7,884,263 B2 * 2/2011 Dewey et al. ................ 800/285

FOREIGN PATENT DOCUMENTS

WO 02/10209 2/2002
WO 02/051231 7/2002

OTHER PUBLICATIONS

Alignment, (Accession No. AAG91409, Dec. 1999, Nakagawa et al. ).*

PCT Notification Concerning Transmittal of International Preliminary Report on Patentability (Form PCT/IB/326) dated Jan. 2004.

PCT International Preliminary Report on Patentability (Form PCT/IB/373) dated Jan. 2004.

PCT Written Opinion of the International Searching Authority (Form/ISA/237) dated Apr. 2005.

Goulding, et al, "Cobalamin-Dependent Methionine Synthase Is a Modular Protein with Distinct Regions for Binding . . . Adenosylmethionine", Biochemistry 1997, 1997 American Chemical Society, 36, pp. 8082-8091, XP009104977.

Nishio, et al., "Comparative Complete Genome Sequence Analysis of the Amino . . . efficiens", Genome Research, 2003, downloaded from www.genome.org on Jun. 28, 2006, pp. 1572-1579, XP-002387831.

Ruckert, et al., "Genome-wide analysis of the L-methionine biosynthetic . . . complementation", Journal of Biotechnology 104, 2003, pp. 213-228, XP-002329882.

* cited by examiner

*Primary Examiner* — Hope Robinson

(74) *Attorney, Agent, or Firm* — Smith, Gambrell & Russell, LLP

(57) ABSTRACT

The present invention relates to nucleotide sequences encoding enzymatically active cobalamin-methionine synthase and functional fragments thereof that are modified in comparison to the respective wild-type enzyme such that said enzymes show reduced product inhibition by methionine. The present invention also relates to polypeptides being encoded by such nucleotide sequences and host cells comprising such nucleotide sequences. Furthermore, the present invention relates to methods for producing methionine in host organisms by making use of such nucleotide sequences.

14 Claims, 21 Drawing Sheets

Figure 2

```
                                   1                                                 50
metH_Cglutamicum database    (1)   -MSTSVTSPAHNNAHSSEFLDALANHVLIGDGAMGTQLQGFDLDVEK---
     metH_Scoel_NC_003888    (1)   MASSPSTPPADTRTRVSALREALATRVVVADGAMGTMLQAQNPTLD----
               metH_Ecoli    (1)   ------------SSKVEQLRAQLNERILVLDGGMGTMIQSYRLNEADFRG
          metH_Thermotoga    (1)   ------------MRNRREVSKLLSERVLLLDGAYGTEFMKYGYDDLP---
                Consensus    (1)     SS   T PA    SKVSELRDALAERVLVLDGAMGTMLQAY LDLD
                                   51                                               100
metH_Cglutamicum database   (47)   -----DFLDLEGCNEILNDTRPDVLRQIHRAYEEAGADLVETNTFGCNLP
     metH_Scoel_NC_003888   (47)   -----DFQQLEGCNEVLNLTRPDIVRSVHEEYFAAGVDCVETNTFGANHS
               metH_Ecoli   (39)   ERFADWPCDLKGNNDLLVLSKPEVIAAIHNAYFEAGADIIETNTFNSTTI
          metH_Thermotoga   (36)   ---------------EELNIKAPDVVLKVHRSYIESGSDVILTNTFGATRM
                Consensus   (51)        DF DLEGCNEILNLTRPDVVRAIHRAYFEAGADIIETNTFGAT I
                                   101                                              150
metH_Cglutamicum database   (92)   NLADYDIADRCRELAYKGTAVAREVADEMGPGRNGMRRFVVGSLGPGTKL
     metH_Scoel_NC_003888   (92)   ALGEYDIPERVHELSEAGARVAREVADEFG-ARDGRQRWVLGSMGPGTKL
               metH_Ecoli   (89)   AMADYQMESLSAEINFAAAKLARACADEWTARTPEKPRYVAGVLGPTNRT
          metH_Thermotoga   (72)   KLRKHGLEDKLDPIVRNAVRIARRAAGEKL---------VFGDIGPTGEL
                Consensus  (101)   ALADYDIEDRL EIAFAAARVAREVADEFG AR GK RFVLGSLGPTTKL
                                   151                                              200
metH_Cglutamicum database  (142)   PSLG----------HAPYADLRGHYKEAALGIIDGGGDAFLIETAQDLLQV
     metH_Scoel_NC_003888  (141)   PTLG----------HAPYTVLRDAYQRNAEGLVAGGADALLVETTQDLLQT
               metH_Ecoli  (139)   ASISPDVNDPAFRNITFDGLVAAYRESTKALVEGGADLILIETVFDTLNA
          metH_Thermotoga  (113)   PYPLG---------STLFEEFYENFRETVEIMVEEGVDGIIFETFSDILEL
                Consensus  (151)   PSLG          HAPFDDLREAYRESAEGLVEGGADAILIET QDLLQL
                                   201                                              250
metH_Cglutamicum database  (183)   KAAVHGVQDAMAELDTFLPIICHVTVETTG-TMLMGSEIGAALTALQPLG
     metH_Scoel_NC_003888  (182)   FASVLGARRALDVLGLDLPLIVSVTVETTG-TMLLGSEIGAALTALEPLG
               metH_Ecoli  (189)   KAAVFAVKTEFEALGVELPIMISGTITDASGRTLSGQTTEAFYNSLRHAE
          metH_Thermotoga  (155)   KAAVLAAR----EVSRDVPLIAHMTFDEKG-RSLTGTDPANFAITFDELD
                Consensus  (201)   KAAVLAVR ALDELGLDLPIIISVTVETTG TMLSGSEIGAFLTALDPLG
                                   251                                              300
```

Figure 2 cont.

```
                                  301                                                350
metH_Cglutamicum database   (232) IDMIGLNCATGPDEMSEHLKYLSKHADIPVSVMPNAGLPVLGKNGAEYPL
     metH_Scoel_NC_003888   (231) IDMIGLNCATGPAEMSEHLRYLARHSKIPLTCMPNAGLPVLGKDGAHYPL
               metH_Ecoli   (239) ALTPGLNCALGPDELRQYVQELSRIAECYVTAHPNAGLPNAFG---EYDL
           metH_Thermotoga  (200) IDALGINCSLGPEEILPIFQELSQYTDKPLVVEPNAGKPIVENGKTVYPL
                Consensus   (251) IDMIGLNCATGPDEMSEHLRYLSRHADIPLTVMPNAGLPVLGK GAEYPL
                                  351                                                400
metH_Cglutamicum database   (282) EAEDLAQALAGFVSEYGLSMVGGCCGTTPEHIRAVREAVVGVPEQETSTL
     metH_Scoel_NC_003888   (281) TAPELADAHETFVREYGLSLVGGCCGTTPEHLRQVVERVRDTAP------
               metH_Ecoli   (286) DADTMAKQIREWAQAGFLNIVGGCCGTTPQHIAAMSRAVEGLAP------
           metH_Thermotoga  (250) KPEDFAVHIDSYYELG-VNIFGGCCGTTPEHVKLFRKVLGNRKP------
                Consensus   (301) DADDLA AIDSFV EYGLSIVGGCCGTTPEHIRAVRKAV GLAP
                                  401                                                450
metH_Cglutamicum database   (332) TKIFAGEVEQASPEVEKEDSVASLYTSVPLSQETGISMIGERTNSNGSKA
     metH_Scoel_NC_003888   (325) ----------TARDPRPEEGAASLYQTVPFRQDTSYLAIGERTNANGSKK
               metH_Ecoli   (330) ----------RKLPEIPVACRLSGLEPLNIGEDSLFVNVGERTNVTGSAK
           metH_Thermotoga  (293) ------------LQRKKKR-IFAVSSPSKLVTFDHFVVIGERINPAGRKK
                Consensus   (351)              ARD KPE  IASLYSPVPL QDT FVMIGERTNANGSKK
                                  451                                                500
metH_Cglutamicum database   (382) FREAMLSGDWEKCVDIAKQQTKDGAHMLDLCVDYVGRDGTADMATLAALL
     metH_Scoel_NC_003888   (365) FREAMLDGRWDDCVEMARDQIREGAHMLDLCVDYVGRDGVADMEELAGRF
               metH_Ecoli   (370) FKRLIKEEKYSEALDVARQQVENGAQIIDINMDEGMLDAEAAMVRFLNLI
           metH_Thermotoga  (330) LWAEMQKGNEEIVLKEAKTQVEKGAEVLDVNFGIESQIDVRYVEKIVQTL
                Consensus   (401) FREAMLDGKWEECVDIAKQQVRDGAHMLDLNVDYVGRDGVADMEELANLL
                                  501                                                550
metH_Cglutamicum database   (432) ATS---STLPIMIDSTEPEVIRTGLEHLGGRSIVNSVNFEDGDGPESRYQ
     metH_Scoel_NC_003888   (415) ATA---STLPIVLDSTEVDVIRAGLEKLGGRAVINSVNYEDGAGPESRFA
               metH_Ecoli   (420) AGEPDIARVPIMIDSSKWDVIEKGLKCIQGKGIVNSISMKEGVD---AFI
           metH_Thermotoga  (380) PYV---SNVPLSLDIQNVDLTERALRAYPGRSLFNSAKVDEEEL-----E
                Consensus   (451) ATA   STLPIMIDSTEVDVIRKGLE LGGRSIVNSVNVEDGDGPESRP
metH_Cglutamicum database   (479) RIMKLVKQHGAAVVALTIDEEGQARTAEHKVRIAKRLIDDITGSYGLDIK
     metH_Scoel_NC_003888   (462) RVTKLAREHGAALIALTIDEVGQARTAEKKVEIAERLIDDLTGNWGIHES
               metH_Ecoli   (467) HEAKLLRRYGAAVVVMAFDEQGQADTRARKIEICRRAYKILTEEVGFPPE
```

Figure 2 cont.

```
            metH_Thermotoga  (422) MKINLLKKYGGTLIVLLMG-KDVFKSFEERKEYFEKALKILERHD--FSD
                  Consensus  (501) RIIKLLKKHGAALIVLTIDE GQARTAEKKVEIAERLIKILTG WGI  D
                                   551                                            600
metH_Cglutamicum database  (529) DIVVDCLTFPISTGQEETRRDGIETIEAIRELKKLYPEIRTTLGLSNISF
      metH_Scoel_NC_003888  (512) DILVDCLTFTICTGQEESRKDGLATIEGIRELKRRHPDVQTTLGLSNISF
                 metH_Ecoli  (517) DIIFDPNIFAVATGIEEHNNYAQDFIGACEDIKRELPHALISGGVSNVSF
            metH_Thermotoga  (469) RVIFDPGVLPLGAEGKP-----VEVLKTIEFISSKG--FNTTVGLSNLSF
                  Consensus  (551) DIIVDPLTFPIATGQEESRKDGIETIEAIREIKRKHPDINTTLGLSNISF
                                   601                                            650
metH_Cglutamicum database  (579) GLN--PAARQVLNSVFLNECIEAGLDSAIARSSKILPMNRIDDRQREVAL
      metH_Scoel_NC_003888  (562) GLN--PAARILLNSVFLDECVKAGLDSAIVHASKILPIARFDEEQVTTAL
                 metH_Ecoli  (567) SFRGNDPVREAIHAVFLYYAIRNGMDMGIVNAGQLAIYDDLPAELRDAVE
            metH_Thermotoga  (512) GLP----DRSYYNTAFLVLGISKGLSSAIMNPLDETLMKTLNAT------
                  Consensus  (601) GLN  PAAR LLNSVFL ECIKAGLDSAIVNASKILPM RLDAEQRD AL
                                   651                                            700
metH_Cglutamicum database  (627) DMVYDRRTEDYDPLQEFMQLFEGVSAADAKDARAEQLAAMPLFERLAQRI
      metH_Scoel_NC_003888  (610) DLIYDRRREGYDPLQKLMQLFEGATAKSLKASKAEELAALPLEERLKRRI
                 metH_Ecoli  (617) DVILNRRDDGTERLLELAEKYRGSKTDDTANAQQAEWRSWEVNKRLEYSL
            metH_Thermotoga  (552) -------------LVILEKK---------------ELPRAEVKEEKLVEII
                  Consensus  (651) DLIYDRR EGYDPLQELMQLFEGASA D K AKAEELRALPLEERL  RI
                                   701                                            750
metH_Cglutamicum database  (677) IDGDKNGLEDDLEAGMKEKS-PIAIINEDLLNGMKTVGELFGSGQMQLPF
      metH_Scoel_NC_003888  (660) IDGEKNGLEQDLDEALRERP-ALEIVNDTLLDGMKVVGELFGSGQMQLPF
                 metH_Ecoli  (667) VKGITEFIEQDTEEARQQATRPIEVIEGPLMDGMNVVGDLFGEGKMFLPQ
            metH_Thermotoga  (575) LSGNRSELEKLVEDFLKEKD-PLSVIEEHLRPAMERIGELYDRGKIFLPQ
                  Consensus  (701) IDGDKNGLEQDLEEALKEKS PIEIINE LLDGMKVVGELFGSGQMQLPQ
                                   751                                            800
metH_Cglutamicum database  (726) VLQSAETMKTAVAYLEPFMEEEAEATGSAQAEGKGKIVVATVKGDVHDIG
      metH_Scoel_NC_003888  (709) VLQSAEVMKTAVAHLEPHMEKTDDDG-------KGTIVLATVRGDVHDIG
                 metH_Ecoli  (717) VVKSARVMKQAVAYLEPFIEASKEQG-----KTNGKMVIATVKGDVHDIG
            metH_Thermotoga  (624) LIIAAQTVKPVFDELTSMLPSDSQGE---------TFVIATVKGDVHDIG
                  Consensus  (751) VLQSAEVMKTAVAYLEPFMEASAEAG         KGTIVIATVKGDVHDIG
                                   801                                            850
```

Figure 2 cont.

```
                                     851                                              900
metH_Cglutamicum database   (776)  KNLVDIILSNNGYDVVNLGIKQPLSAMLEAAEEHKADVIGMSGLLVKSTV
      metH_Scoel_NC_003888  (752)  KNLVDIILSNNGYNVVNLGIKQPVSAILEAADEHRADVIGMSGLLVKSTV
                metH_Ecoli  (762)  KNIVGVVLQCNNYEIVDLGVMVPAEKILRTAKEVNADLIGLSGLITPSLD
           metH_Thermotoga  (665)  KNIVASVIRSSGYRVVDLGKDVDTSEIVEAVEKERPVALGLSAMMTTTVG
                 Consensus  (801)  KNIVDIILSNNGYDVVNLGIKVPLSAILEAAEEHRADVIGLSGLLVKSTV
                                   901                                              950
metH_Cglutamicum database   (826)  VMKENLEEMNN-AGASNYPVILGGAALTRTYVENDLNEVYTGEVYYARDA
      metH_Scoel_NC_003888  (802)  IMKENLEELNQPKLAADYPVILGGAALTRAYVEQDLEEIYDGEVRYARDA
                metH_Ecoli  (812)  EMVNVAKEMER--QGFTIPLLIGGATTSKAHTAVKIEQNYSGPTVYVQNA
           metH_Thermotoga  (715)  RIKEVVEKLKE--KNLKIPVIVGGASLN------EKLAKELGADYYAKNA
                 Consensus  (851)  IMKEVLEELNN    AA YPVILGGAALTRAYVENDL EIYSGEVYYARNA
                                   951                                             1000
metH_Cglutamicum database   (875)  FEGLRLMDEVMAEKRGEGLDPNSPEAIEQAKKKAERKARNERSRKIAAER
      metH_Scoel_NC_003888  (852)  FEGLRLMDALIGIKRG------VP-----GAKLPELKQR----RVRAATV
                metH_Ecoli  (860)  SRTVGVVAALLSDTQRDDFVARTRKEYETVRIQHGRKKP----RTPPVTL
           metH_Thermotoga  (757)  SEAVKILESLGR--------------------------------------
                 Consensus  (901)  SEGLRLMDALIADKRGD       SP    E AKK   ERK R     R  AATL
                                   1001                                            1050
metH_Cglutamicum database   (925)  KANAAPVIVPEERSDVSTDTPTAAPPFWGTRIVKGLPLAEFLGNLDERALF
      metH_Scoel_NC_003888  (887)  EIDERPEEGHVRSDVATDNPVPTPPFRGTRVVKGIQLKEYASWLDEGALF
                metH_Ecoli  (906)  EAAR-------DNDFAFDWQAYTPPVAHRLGVQEVEASIETLRNYIDWTPF
           metH_Thermotoga  (769)  --------------------------------------------------
                 Consensus  (951)  EA    E      DRSDVATDNP    PPF GTRVVKGI L EFL NLDE ALF
                                   1051                                            1100
metH_Cglutamicum database   (975)  MGQWGLRSTRGNEGPSYEDLVETEGRPRLRYWLDRLKSEGILDHVALVYG
      metH_Scoel_NC_003888  (937)  EGQWGLKQARTGEGPSYEELVESEGRPRLRGLLDRLQTD-NLLEAAVVYG
                metH_Ecoli  (950)  FMTWSLAGKYPRILEDEVVGVEAQRLFKDANDMLDKLSAEKTLNPRGVVG
           metH_Thermotoga  (769)  --------------------------------------------------
                 Consensus (1001)   GQWGLK   R  EGPSYEDLVESEGRPRLR   LDRL SD   LL   ALVYG

                                   1051                                            1100
metH_Cglutamicum database  (1025)  YFPAVAEGDDVVILESPDPHAAERMRFSFPRQQRGR---FLCIADFIRPR
      metH_Scoel_NC_003888  (986)  YFPCVSKDDDLIVLLDDG---NERTRFTFPRQKRGR---RLCLADFFRPE
```

Figure 2 cont.

```
                 metH_Ecoli  (1000) LFPANRVGDDIEIYRDETRTHVINVSHHLRQQTEKTGFANYCLADFVAPK
            metH_Thermotoga   (769) ~~~~~~~~~~~~~~~~~~~~~~~~~~~~~~~~~~~~~~~~~~~~~~~~~~
                  Consensus  (1051) YFPAVA GDDIIILDDD     ERMRFSFPRQ RGR    LCLADFIRPK
                                    1101                                           1150
metH_Cglutamicum database  (1072) EQAVKDGQVDVMPFQLVTMGNPIADFANELFAANEYREYLEVHGIGVQLT
      metH_Scoel_NC_003888  (1030) E----SGETDVVGFQVVTVGSRIGEETARMFEANAYRDYLELHGLSVQLA
                 metH_Ecoli  (1050) LS----GEADYIGAFAVTGGLEEDALADAFEAQHDDYNKIMVKALADRLA
            metH_Thermotoga   (769) ~~~~~~~~~~~~~~~~~~~~~~~~~~~~~~~~~~~~~~~~~~~~~~~~~~
                  Consensus  (1101) E     G  DVIGFQLVTMG  IAD A  LFAANDYRDYLEVHGLAVQLA
                                    1151                                           1200
metH_Cglutamicum database  (1122) EALAEYWHSRVRSELKLNDGGSVADFDPEDKTKFFDLDYRGARFSFGYGS
      metH_Scoel_NC_003888  (1076) EALAEYWHARVRSELGFAG~~~~~~EDPAEMEDMFALKYRGARFSLGYGA
                 metH_Ecoli  (1096) EAFAEYLHERVRKVYWGYAP-----NENLSNEELIRENYQGIRPAPGYPA
            metH_Thermotoga   (769) --------------------------------------------------
                  Consensus  (1151) EALAEYWHARVRSEL   A        DF D EDLF L YRGARFS GYGA
                                    1201                                           1250
metH_Cglutamicum database  (1172) CPDLEDRAKLVELLEPGR~IGVELSEELQLHPEQSTDAFVLYHPEAKYFN
      metH_Scoel_NC_003888  (1120) CPDLEDRAKIAALLEPER~IGVHLSEEFQLHPEQSTDAIVIHHPEAKYFN
                 metH_Ecoli  (1141) CPEHTEKATIWELLEVEKHTGMKLTESFAMWPGASVSGWYFSHPDSKYYA
            metH_Thermotoga   (769) ~~~~~~~~~~~~~~~~~~~~~~~~~~~~~~~~~~~~~~~~~~~~~~~~~~
                  Consensus  (1201) CPDLEDRAKI ELLEPER IGV LSEEFQLHPEQSTDAFVIHHPEAKYFN
                                    1251                               1286
metH_Cglutamicum database  (1221) V-----------------------------------
      metH_Scoel_NC_003888  (1169) AR~~~~~~~~~~~~~~~~~~~~~~~~~~~~~~~~~~
                 metH_Ecoli  (1191) VAQIQRDQVEDYARRKGMSVTEVERWLAPNLGYDAD
            metH_Thermotoga   (769) ~~~~~~~~~~~~~~~~~~~~~~~~~~~~~~~~~~~~
                  Consensus  (1251) V
```

Figure 3:

a) SEQ ID No. 1:

MSTSVTSPAHNNAHSSEFLDALANHVLIGDGAMGTQLQGFDLDVEKDFLDLEGCNEILNDTRPDVLRQIHRAYFEAGADLVETNTFGCNLPNLADYDIA
DRCRELAYKGTAVAREVADEMGPGRNGMRRFVVGSLGPGTKLPSLGHAPYADLRGHYKEAALGIIDGGGDAFLIETAQDLLQVKAAVHGVQDAMAELDT
FLPIICHVTVETTGTMLMGSEIGAALTALQPLGIDMIGLNCATGPDEMSEHLRYLSKHADIPVSVMPNAGLPVLGKNGAEYPLEAEDLAQALAGFVSEY
GLSMVGGCCGTTPEHIRAVRDAVVGVPEQETSTLTKIPAGPVEQASREVEKEDSVASLYTSVPLSQETGISMIGERTNSNGSKAFREAMLSGDWEKCVD
IAKQQTRDGAHMLDLCVDYVGRDGTADMATLAALLATSSTLPIMIDSTEPEVIRTGLEHLGGRSIVNSVNFEDGDGPESRYQRIMKLVKQHGAAVVALT
IDEEGQARTAEHKVRIAKRLIDDITGSYGLDIKDIVVDCLTFPISTGQEETRRDGIETIEAIRELKKLYPEIHTTLGLSNISFGLNPAARQVLNSVFLN
ECIEAGLDSAIAHSSKILPMNRIDDRQREVALDMVYDRRTEDYDPLQEFMQLFEGVSAADAKDARAEQLAAMPLFERLAQRIIDGDKNGLEDDLEAGMK
EKSPIAIINEDLLNGMKTVGELFGSGQMQLPFVLQSAETMKTAVAYLEPFMEEEAEATGSAQAEGKGKIVVATVKGDVHDIGKNLVDIILSNNGYDVVN
LGIKQPLSAMLEAAEEHKADVIGMSGLLVKSTVVMKENLEEMNNAGASNYPVILGGAALTRTYVENDLNEVYTGEVYYARDAFEGLRLMDEVMAEKRGE
GLDPNSPEAIEQAKKKAERKARNERSRKIAAERKANAAPVIVPERSDVSTDTPTAAPPFWGTRIVKGLPLAEFLGNLDERALFMGQWGLKSTRGNEGPS
YEDLVETEGRPRLRYWLDRLKSEGILDHVALVYGYFPAVAEGDDVVILESPDPHAAERMRFSFPRQQRGRFLCIADFIRPREQAVKDGQVDVMPFQLVT
MQNPIADFANELFAANEYREYLEVHGIGVQLTEALAEYWHSRVRSELKLNDGGSVADFDPEDKTKFFDLDYRGARFSFGYGSCPDLEDRAKLVELLEPG
RIGVELSEELQLHPEQSTDAFVLYHPEAKYFNV b) SEQ ID No. 23:

atgtctacttcagttacttcaccagcccacaacaacgcacattcctccgaatttttggatgcgttggcaaaccatgtgttgatcggcgacggcgccatg
ggcacccagctccaaggctttgacctggacgtggaaaaggatttccttgatctggaggggtgtaatgagattctcaacgacacccgccctgatgtgttg
aggcagattcaccgcgcctactttgaggcgggagctgaccttgttgagaccaatacttttggttgcaacctgccgaacttggcggattatgacatcgct
gatcgttgccgtgagcttgcctacaagggcactgcagtggctagggaagtggctgatgagatggggccgggccgaaacggcatgcggcgtttcgtggtt
ggttccctgggacctggaacgaagcttccatcgctgggccatgcaccgtatgcagatttgcgtgggcactacaaggaagcagcgcttggcatcatcgac
ggtggtggcgatgcctttttgattgagactgctcaggacttgcttcaggtcaaggctgcggttcacggcgttcaagatgccatggctgaacttgataca
ttcttgcccattatttgccacgtcaccgtagagaccaccggcaccatgctcatgggttctgagatcggtgccgcgttgacagcgctgcagccactgggt
atcgacatgattggtctgaactgcgccaccggccccgatgagatgagcgagcacctgcgttacctgtccaagcacgccgatattcctgtgtcggtgatg
ccgaacgcaggtcttcctgtcctgggtaaaaacggtgcagaatacccacttgaggctgaggatttggcgcaggcgctggctggattcgtctccgaatat
ggcctgtccatggtgggtggttgttgtggcaccacacctgagcacatccgtgcggtccgcgatgcggtggttggtgttccagagcaggaaacctccaca
ctgaccaagatccctgcaggccctgttgagcaggcctcccgcgaggtggagaaagaggactccgtcgcgtcgctgtacacctcggtgccattgtcccag
gaaaccggcatttccatgatcggtgagcgcaccaactccaacggttccaaggcattccgtgaggcaatgctgtctggcgattgggaaaagtgtgtggat
attgccaagcagcaaacccgcgatggtgcacacatgctggatctttgtgtggattacgtgggacgagacggcaccgccgatatggcgaccttggcagca
cttcttgctaccagctccactttgccaatcatgattgactccaccgagccagaggttattcgcacaggccttgagcacttgggtggacgaagcatcgtt
aactccgtcaactttgaagacggcgatggccctgagtcccgctaccagcgcatcatgaaactggtaaagcagcacggtgcggccgtggttgcgctgacc

Figure 3 cont.

attgatgaggaaggccaggcacgtaccgctgagcacaaggtgcgcattgctaaacgactgattgacgatatcaccggcagctacggcctggatatcaaa
gacatcgttgtggactgcctgaccttcccgatctctactggccaggaagaaaccaggcgagatggcattgaaaccatcgaagccatcccgcgagctgaag
aagctctacccagaaatccacaccacctgggtctgtccaatatttccttcggcctgaaccctgctgcacgccaggttcttaactctgtgttcctcaat
gagtgcattgaggctggtctggactctgcgattgcgcacagctccaagatttgccgatgaaccgcattgatgatcgccagcgcgaagtggcgttggat
atggtctatgatcgccgcaccgaggattacgatccgctgcaggaattcatgcagctgtttgagggcgtttctgctgccgatgccaaggatgctcgcgct
gaacagctggccgctatgcctttgtttgagcgtttggcacagcgcatcatcgacggcgataagaatggccttgaggatgatctggaagcaggcatgaag
gagaagtctcctattgcgatcatcaacgaggaccttctcaacggcatgaagaccgtgggtgagctgtttggttccggacagatgcagctgccattcgtg
ctgcaatcggcagaaaccatgaaaactgcggtggcctatttggaacgttcatggaagaggaagcagaagctaccggatctgcgcaggcagagggcaag
ggcaaaatcgtcgtggccaccgtcaagggtgacgtgcacgatatcggcaagaacttggtggacatcatttgtccaacaacggttacgacgtggtgaac
ttgggcatcaagcagccactgtccgccatgttggaagcagcggaagaacacaaagcagacgtcatcggcatgtcgggacttcttgtgaagtccaccgtg
gtgatgaaggaaaaccttgaggagatgaacaacgccggcgcatccaattacccagtcattttgggtggcgctgcgctgacgcgtacctacgtggaaaac
gatctcaacgaggtgtacaccggtgaggtgtactacgcccgtgatgctttcgagggcctgcgcctgatggatgaggtgatggcagaaaagcgtggtgaa
ggacttgatcccaactcaccagaagctattgagcaggcgaagaagaaggcggaacgtaaggctcgtaatgagcgttcccgcaagattgccgcggagcgt
aaagctaatgcggctcccgtgattgttccggagcgttctgatgtctccaccgatactccaaccgcggcaccaccgttctggggaacccgcattgtcaag
ggtctgcccttggcggagttcttgggcaaccttgatgagcgcgccttgttcatggggcagtggggtctgaaatccacccgcggcaacgagggtccaagc
tatgaggatttggtggaaactgaaggccgaccacgcctgcgctactggctggatcgcctgaagtctgagggcatttggaccacgtggccttggtgtat
ggctacttcccagcggtcgcggaaggcgatgacgtggtgatcttggaatccccggatccacacgcagccgaacgcatgcgctttagcttcccacgccag
cagcgcggcaggttcttgtgcatcgcggatttcattcgcccacgcgagcaagctgtcaaggacggccaagtggacgtcatgccattccagctggtcacc
atgggtaatcctattgctgatttcgccaacgagttgttcgcagccaatgaataccgcgagtacttggaagttcacggcatcggcgtgcagctcaccgaa
gcattggccgagtactggcactcccgagtgcgcagcgaactcaagctgaacgacggtggatctgtcgctgattttgatccagaagacaagaccaagttc
ttcgacctggattacccgcggcgcccgcttctcctttggttacggttcttgccctgatctggaagaccgcgcaaagctggtggaattgctcgagccaggc
cgtatcggcgtggagttgtccgaggaactccagctgcacccagagcagtccacagacgcgtttgtgctctaccacccagaggcaaagtactttaacgtc
taa

Figure 4 a) SEQ ID No. 2.

MSTSVTSPAHNNAHSSEFLDALANHVLIGDGAMGTQLQSFDLDVEKDFLDLEGCNEILNDTRPDVLRQIHRAYFEAGADLVETNTFGCNLPNLADYDIA
DRCEELAYKGTAVAREVADEMGPGRNGMRRFVVGSLGPGTKLPSLGHAPYADLRGHYKEAALGIIDGGGDAFLIETAQDLLQVKAAVHGVQDAMAELDE
FLPIICEVTVETTGTMLMGSEIGAALTALQPLGIDMIGINCATGPDE b) SEQ ID No. 24 atgtctacttcagttagttcacccagcccacaacaacgcacattcctccgaatttttggatgcgttggcaaaccatgtgttgatcggcgacggcgccatg
ggcacccagctccaaggctttgacctggacgtggaaaaggatttccttgatctggaggggtgtaatgagattctcaacgacacccgccctgatgtgttg
aggcagattcaccgcgcctactttgaggcgggagctgacttggttgagaccaatacttttggttgcaacctgccgaacttggcggattatgacatcgct
gatcgttgccgtgagcttgcctacaagggcactgcagtggctagggaagtggctgatgagatggggccggggccgaaacggcatgcggcgtttcgtggtt
ggttccctgggacctggaacgaagcttccatcgctgggccatgcaccgtatgcagatttgcgtgggcactacaaggaagcagcgcttggcatcatcgac
ggtggtggcgatgcctttttgattgagactgctcaggacttgcttcaggtcaaggctgcggttcacggcgttcaagatgccatggctgaacttgatacca
ttcttgcccattatttgccacgtcaccgtagagaccaccggcaccatgctcatgggttctgagatcggtgccgcgttgactgcgctgcagccactgggt
atcgacatgattggtctgaactgcgccaccggcccagatgag

Figure 5

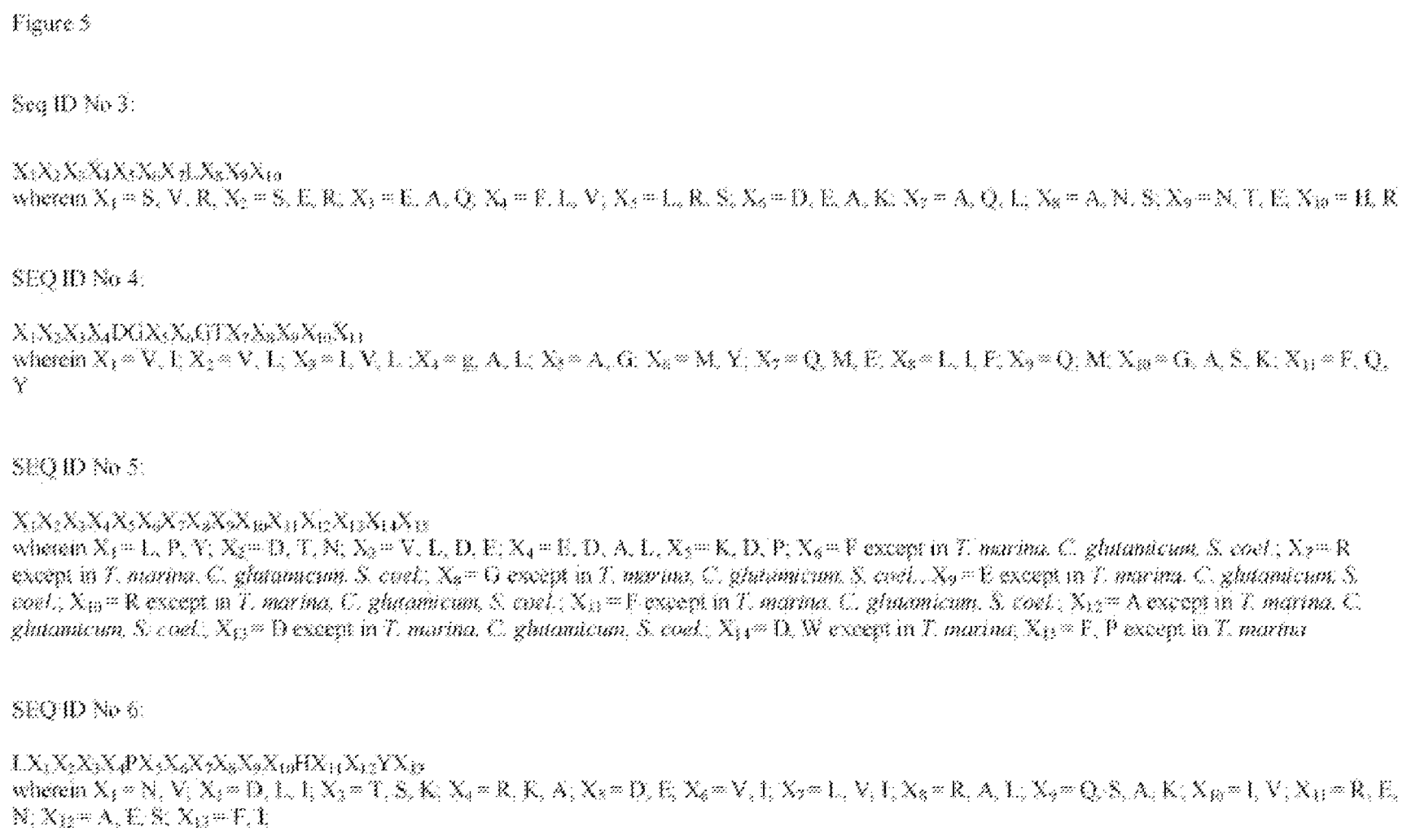

Seq ID No 3:

$X_1X_2X_3X_4X_5X_6X_7LX_8X_9X_{10}$
wherein $X_1$ = S, V, R; $X_2$ = S, E, R; $X_3$ = E, A, Q; $X_4$ = F, L, V; $X_5$ = L, R, S; $X_6$ = D, E, A, K; $X_7$ = A, Q, L; $X_8$ = A, N, S; $X_9$ = N, T, E; $X_{10}$ = H, R SEQ ID No 4:

$X_1X_2X_3X_4DGX_5X_6GTX_7X_8X_9X_{10}X_{11}$
wherein $X_1$ = V, I; $X_2$ = V, L; $X_3$ = I, V, L ;$X_4$ = g, A, L; $X_5$ = A, G; $X_6$ = M, Y; $X_7$ = Q, M, E; $X_8$ = L, I, F; $X_9$ = Q; M; $X_{10}$ = G, A, S, K; $X_{11}$ = F, Q, Y SEQ ID No 5:

$X_1X_2X_3X_4X_5X_6X_7X_8X_9X_{10}X_{11}X_{12}X_{13}X_{14}X_{15}$
wherein $X_1$ = L, P, Y; $X_2$ = D, T, N; $X_3$ = V, L, D, E; $X_4$ = E, D, A, L, $X_5$ = K, D, P; $X_6$ = F except in *T. marina, C. glutamicum, S. coel.*; $X_7$ = R except in *T. marina, C. glutamicum, S. coel.*; $X_8$ = G except in *T. marina, C. glutamicum, S. coel.*, $X_9$ = E except in *T. marina, C. glutamicum, S. coel.*; $X_{10}$ = R except in *T. marina, C. glutamicum, S. coel.*; $X_{11}$ = F except in *T. marina, C. glutamicum, S. coel.*; $X_{12}$ = A except in *T. marina, C. glutamicum, S. coel.*; $X_{13}$ = D except in *T. marina, C. glutamicum, S. coel.*; $X_{14}$ = D, W except in *T. marina*; $X_{15}$ = F, P except in *T. marina*

SEQ ID No 6:

$LX_1X_2X_3X_4PX_5X_6X_7X_8X_9X_{10}HX_{11}X_{12}YX_{13}$
wherein $X_1$ = N, V; $X_2$ = D, L, I; $X_3$ = T, S, K; $X_4$ = R, K, A; $X_5$ = D, E; $X_6$ = V, I; $X_7$ = L, V, I; $X_8$ = R, A, L; $X_9$ = Q, S, A, K; $X_{10}$ = I, V; $X_{11}$ = R, E, N; $X_{12}$ = A, E, S; $X_{13}$ = F, I

Figure 5 cont.

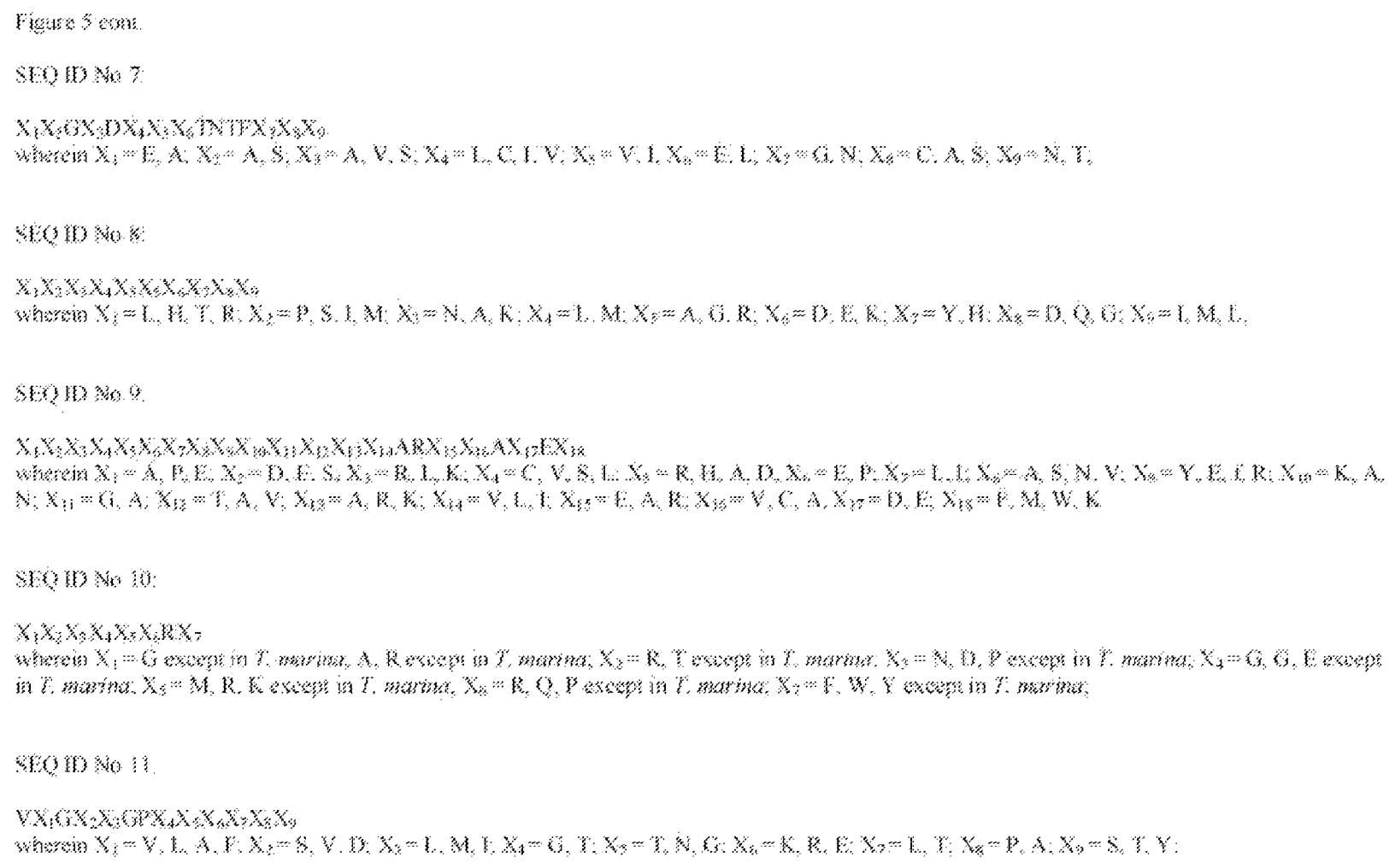

SEQ ID No 7:

$X_1X_2GX_3DX_4X_5X_6TNTFX_7X_8X_9$ wherein $X_1$ = E, A; $X_2$ = A, S; $X_3$ = A, V, S; $X_4$ = L, C, I, V; $X_5$ = V, I, $X_6$ = E, L; $X_7$ = G, N; $X_8$ = C, A, S; $X_9$ = N, T;

SEQ ID No 8:

$X_1X_2X_3X_4X_5X_6X_6X_7X_8X_9$ wherein $X_1$ = L, H, T, R; $X_2$ = P, S, I, M; $X_3$ = N, A, K; $X_4$ = L, M; $X_5$ = A, G, R; $X_6$ = D, E, K; $X_7$ = Y, H; $X_8$ = D, Q, G; $X_9$ = I, M, L, SEQ ID No 9:

$X_1X_2X_3X_4X_5X_6X_7X_8X_9X_{10}X_{11}X_{12}X_{13}X_{14}ARX_{15}X_{16}AX_{17}EX_{18}$ wherein $X_1$ = A, P, E; $X_2$ = D, E, S; $X_3$ = R, L, K; $X_4$ = C, V, S, L; $X_5$ = R, H, A, D, $X_6$ = E, P; $X_7$ = L, I; $X_8$ = A, S, N, V; $X_9$ = Y, E, I, R; $X_{10}$ = K, A, N; $X_{11}$ = G, A; $X_{12}$ = T, A, V; $X_{13}$ = A, R, K; $X_{14}$ = V, L, I; $X_{15}$ = E, A, R; $X_{16}$ = V, C, A, $X_{17}$ = D, E; $X_{18}$ = F, M, W, K SEQ ID No 10:

$X_1X_2X_3X_4X_5X_6RX_7$ wherein $X_1$ = G except in *T. marina*, A, R except in *T. marina*; $X_2$ = R, T except in *T. marina*; $X_3$ = N, D, P except in *T. marina*; $X_4$ = G, G, E except in *T. marina*; $X_5$ = M, R, K except in *T. marina*, $X_6$ = R, Q, P except in *T. marina*; $X_7$ = F, W, Y except in *T. marina*;

SEQ ID No 11:

$VX_1GX_2X_3GPX_4X_5X_6X_7X_8X_9$ wherein $X_1$ = V, L, A, F; $X_2$ = S, V, D; $X_3$ = L, M, I; $X_4$ = G, T; $X_5$ = T, N, G; $X_6$ = K, R, E; $X_7$ = L, T; $X_8$ = P, A; $X_9$ = S, T, Y;

Figure 5 cont.

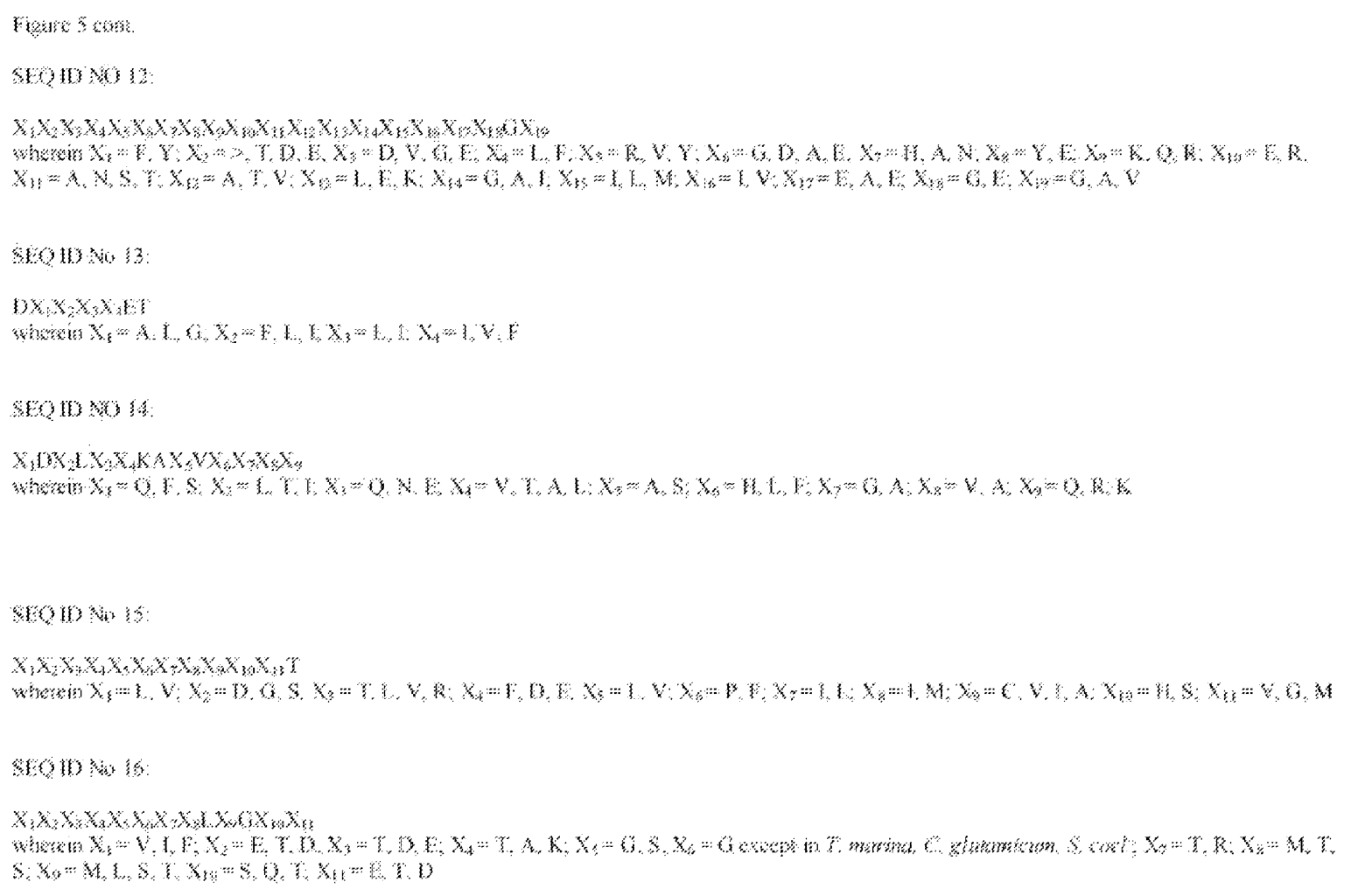

SEQ ID NO 12:

$X_1X_2X_3X_4X_5X_6X_7X_8X_9X_{10}X_{11}X_{12}X_{13}X_{14}X_{15}X_{16}X_{17}X_{18}GX_{19}$
wherein $X_1$ = F, Y; $X_2$ = >, T, D, E, $X_3$ = D, V, G, E, $X_4$ = L, F; $X_5$ = R, V, Y; $X_6$ = G, D, A, E, $X_7$ = H, A, N; $X_8$ = Y, E; $X_9$ = K, Q, R; $X_{10}$ = E, R, $X_{11}$ = A, N, S, T; $X_{12}$ = A, T, V; $X_{13}$ = L, E, K; $X_{14}$ = G, A, I; $X_{15}$ = I, L, M; $X_{16}$ = I, V; $X_{17}$ = E, A, E; $X_{18}$ = G, E; $X_{19}$ = G, A, V SEQ ID No 13:

$DX_1X_2X_3X_4ET$
wherein $X_1$ = A, L, G, $X_2$ = F, L, I, $X_3$ = L, I; $X_4$ = I, V, F

SEQ ID NO 14:

$X_1DX_2LX_3X_4KAX_5VX_6X_7X_8X_9$
wherein $X_1$ = Q, F, S; $X_2$ = L, T, I; $X_3$ = Q, N, E; $X_4$ = V, T, A, L; $X_5$ = A, S; $X_6$ = H, L, F; $X_7$ = G, A; $X_8$ = V, A; $X_9$ = Q, R, K SEQ ID No 15:

$X_1X_2X_3X_4X_5X_6X_7X_8X_9X_{10}X_{11}T$
wherein $X_1$ = L, V; $X_2$ = D, G, S, $X_3$ = T, L, V, R; $X_4$ = F, D, E, $X_5$ = I, V; $X_6$ = P, F; $X_7$ = I, L; $X_8$ = I, M; $X_9$ = C, V, I, A; $X_{10}$ = H, S; $X_{11}$ = V, G, M SEQ ID No 16:

$X_1X_2X_3X_4X_5X_6X_7X_8LX_9GX_{10}X_{11}$
wherein $X_1$ = V, I, F; $X_2$ = E, T, D, $X_3$ = T, D, E; $X_4$ = T, A, K; $X_5$ = G, S, $X_6$ = G except in *T. marina, C. glutamicum, S. coel*; $X_7$ = T, R; $X_8$ = M, T, S; $X_9$ = M, L, S, T, $X_{10}$ = S, Q, T, $X_{11}$ = E, T, D

Figure 5 cont.

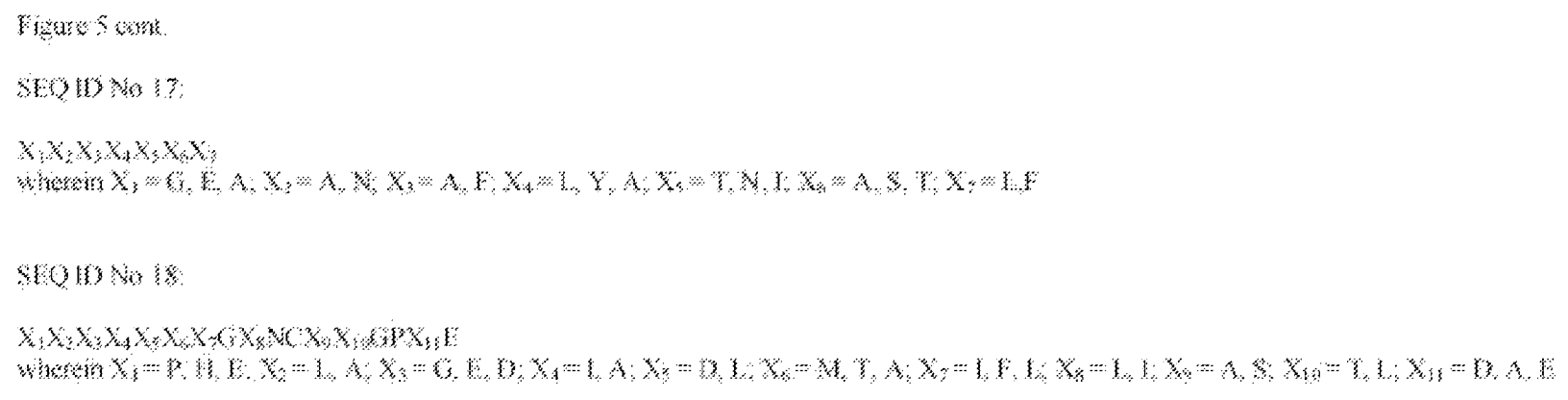

SEQ ID No 17:

$X_1X_2X_3X_4X_5X_6X_7$
wherein $X_1$ = G, E, A; $X_2$ = A, N; $X_3$ = A, F; $X_4$ = L, Y, A; $X_5$ = T, N, I; $X_6$ = A, S, T; $X_7$ = L,F SEQ ID No 18:

$X_1X_2X_3X_4X_5X_6X_7GX_8NCX_9X_{10}GPX_{11}E$
wherein $X_1$ = P, H, E; $X_2$ = L, A; $X_3$ = G, E, D; $X_4$ = I, A; $X_5$ = D, L; $X_6$ = M, T, A; $X_7$ = I, F, L; $X_8$ = L, I; $X_9$ = A, S; $X_{10}$ = T, L; $X_{11}$ = D, A, E a) SEQ ID No. 19:
b) SEQ ID No. 25:

Figure 6 cont.

```
attgatgaggaaggccaggcacgtaccgctgagcacaaggtgcgcattgctaaacgactgattgacgatatcaccggcagctacggcctggatatcaaa
gacatcgttgtggactgcctgacctttcccgatctctactggccaggaagaaaccaggcgagatggcattgaaaccatcgaagccatccgcgagctgaag
aagctctacccagaaatccacaccaccctgggtctgtccaatatttccttcggcctgaaccctgctgcacgccaggttcttaactctgtgttcctcaat
gagtgcattgaggctggtctggactctgcgattgcgcacagctccaagatttgccgatgaaccgcattgatgatcgccagcgcgaagtggcgttggat
atggtctatgatcgccgcaccgaggattacgatccgctgcaggaattcatgcagctgtttgagggcgtttctgctgccgatgccaaggatgctcgcgct
gaacagctggccgctatgcctttgtttgagcgttttggcacagcgcatcatcgacggcgataagaatggccttgaggatgatctggaagcaggcatgaag
gagaagtctcctattgcgatcatcaacgaggaccttctcaacggcatgaagaccgtgggtgagctgtttggttccggacagatgcagctgccattcgtg
ctgcaatcggcagaaaccatgaaaactgcggtggcctatttggaaccgttcatggaagaggaagcagaagctaccggatctgcgcaggcagagggcaag
ggcaaaatcgtcgtggccaccgtcaagggtgacgtgcacgatatcggcaagaacttggtggacatcattttgtccaacaacggttacgacgtggtgaac
ttgggcatcaagcagccactgtccgccatgttggaagcagcggaagaacacaaagcagacgtcatcggcatgtcgggacttcttgtgaagtccaccgtg
gtgatgaaggaaaaccttgaggagatgaacaacgccggcgcatccaattacccagtcattttgggtggcgctgcgctgacgcgtacctacgtggaaaac
gatctcaacgaggtgtacaccggtgaggtgtactacgcccgtgatgctttcgagggcctgcgcctgatggatgaggtgatggcagaaaagcgtggtgaa
ggacttgatcccaactcaccagaagctattgagcaggcgaagaagaaggcggaacgtaaggctcgtaatgagcgttcccgcaagattgccgcggagcgt
aaagctaatgcggctcccgtgattgttccggagcgttctgatgtctccaccgatactccaacccgcggcaccacccgttctggggaacccgcattgtcaag
ggtctgccctttggcggagttcttgggcaaccttgatgagcgcgccttgttcatgggggcagtggggtctgaaatccacccgcggcaacgagggtccaagc
tatgaggatttggtggaaactgaaggccgaccacgcctgcgctactggcctggatcgcctgaagtctgagggcatttggaccacgtggccttggtgtat
ggctactttcccagcggtcgcggaaggcgatgacgtggtgatcttggaatccccggatccacacgcagccgaacgcatgcgctttagcttcccacgccag
cagcgcggcaggttcttgtgcatcgcggatttcattcgcccacgcgagcaagctgtcaaggacggccaagtggacgtcatgccattccagctggtcacc
atgggtaatcctattgctgatttcgccaacgagttgttcgcagccaatgaataccgcgagtacttggaagttcacggcatcggcgtgcagctcaccgaa
gcattggccgagtactggcactcccgagtgcgcagcgaactcaagctgaacgacggtggatctgtcgctgatttgatccagaagacaagaccaagttc
ttcgacctggattacccgcggcgcccgcttctcctttggttacggttcttgcccttgattctggaagacccgcgcaaagctggtggaattgctcgagccaggc
cgtatcggcgtggagttgtccgaggaactccagctgcacccagagcagtccacagacgcgtttgtgctctaccacccagaggcaaagtactttaacgtc
taa
```

Figure 7 a) SEQ ID No. 20:

MSTSVTSPAHNNAHSSEFLDALANHVLIGDGAAGTQLQGFDLDVEKDFLDLEGCNEILNDTRPDVLRQIHRAYFEAGADLVETNTFGCNLPNLADYDIA
DHCRELAYKGTAVAREVADEMGPGRNGMRRFVVGSLGPGTKLPSLGRAPYADLRGHYKEAALGIIDGGGDAFLIETAQDLLQVKAAVHGVQDAMAELDT
FLPIICHVTVETTGTMLMGSEIGAALTALQPLGIDMIGLNCATGPDEMSEHLRYLSKHADIFVSVMPNAGLPVLGKNGAEYPLEAEDLAQALAGFVSEY
GLSMVGGCCGTTPEHIRAVRDAVVGVPEQETSTLTKIPAGPVEQASREVEKEDSVASLYTSVPLSQETGISMIGERTNSNGSKAFREAMLSGDWEKCVD
IAKQQTRDGAHMLDLCVDYVGRDGTADMATLAALLATSSTLPIMIDSTEPEVIRTGLEHLGGRSIVNSVNFEDGDGPESRYQRIMKLVKQHGAAVVALT
IDEEGQARTAEHKVRIAKRLIDDITGSYGLDIKDIVVDCLTFPISTGQEETRRDGIETIEAIRELKKLYPEIHTTLGLSNISFGLNPAARQVLNSVFLN
ECIEAGLDSAIAHSSKILPMNRIDDRQREVALDMVYDRRTEDYDPLQEFMQLFEGVSAADAKDARAEQLAAMPLFERLAQRIIDGDKNGLEDDLEAGMK
EKSPIAIINEDLLNGMKTVGELFGSGQMQLPFVLQSAETMKTAVAYLEPFMEEEAEATGSAQAEGKGKIVVATVKGDVHDIGKNLVDIILSNNGYDVVN
LGIKQPLSAMLEAAEEHKADVIGMSGLLVKSTVVMKENLEEMNNAGASNYPVILGGAALTRTYVENDLNEVYTGEVYYARDAFEGLRLMDEVMAEKRGE
GLDENSPEAIEQAKKKAERKARNERSREIAAERKANAAPVIVPERSDVSTDTPTAAPPFWGTRIVKGLPLAEFLGNLDERALFMGQWGLKSTRGNEGPS
YEDLVETEGRPRLRYWLDRLKSEGILDHVALVYGYFPAVAEGDDVVILESPDPHAAERMRFSFPRQQRGRFLCIADFIRPREQAVKDGQVDVMPFQLVT
MGNPIADFANELFAANEYREYLEVHGIGVQLTEALAEYWHSRVRSELKLNDGGSVADFDPEDKTKFFDLDYRGARFSFGYGSCPDLEDRAKLVELLEPG
RIGVELSEELQLHPEQSTDAFVLYHPEAKYFNV b) SEQ ID No. 26:

atgtctacttcagttacttcaccagcccacaacaacgcacattcctccgaatttttggatgcgttggcaaaccatgtgttgatcggcgacggcgccatg
ggcacccagctccaaggctttgacctggacgtggaaaaggatttccttgatctggagggctgtaatgagattctcaacgacacccgccctgatgtgttg
aggcagattcaccgcgcctactttgaggcgggagctgacttggttgagaccaatacttttggttgcaacctgccgaacttggcggattatgacatcgct
gatcgttgccgtgagcttgcctacaagggcactgcagtggctagggaagtggctgatgagatgggcccgggccgaaacggcatgcggcgtttcgtggtt
ggttccctgggacctggaacgaagcttccatcgctgggccatgcaccgtatgcagatttgcgtgggcactacaaggaagcagcgcttggcatcatcgac
ggtggtggcgatgcctttttgattgagactgctcaggacttgcttcaggtcaaggctgcggttcacggcgttcaagatgccatggctgaacttgataca
ttcttgcccattatttgccacgtcaccgtagagaccaccggcaccatgctcatgggttctgagatcggtgccgcgttgacagcgctgcagccactgggt
atcgacatgattggtctgaactgcgccaccggcccagatgagatgagcgagcacctgcgttacctgtccaagcacgccgatattcctgtgtcggtgatg
cctaacgcaggtcttcctgtcctgggtaaaaacggtgcagaatacccacttgaggctgaggatttggcgcaggcgctggctggattcgtctccgaatat
ggcctgtccatggtgggtggttgttgtggcaccacacctgagcacatccgtgcggtccgcgatgcggtggttggtgttccagagcaggaaacctccaca
ctgaccaagatccctgcaggccctgttgagcaggcctcccgcgaggtggagaaagaggactccgtcgcgtcgctgtacacctcggtgccattgtcccag
gaaaccggcatttccatgatcggtgagcgcaccaactccaacggttccaaggcattccgtgaggcaatgctgtctggcgattgggaaaagtgtgtggat
attgccaagcagcaaacccgcgatggtgcacacatgctggatctttgtgtggattacgtgggacgagacggcaccgccgatatggcgaccttggcagca
cttcttgctaccagctccactttgccaatcatgattgactccaccgagccagaggttattcgcacaggccttgagcacttgggtggacgaagcatcgtt
aactccgtcaactttgaagacggcgatggccctgagtcccgctaccagcgcatcatgaaactggtaaagcagcacggtgcggccgtggttgcgctgacc

Figure 7 cont.

attgatgaggaaggccaggcacgtaccgctgagcacaaggtgcgcattgctaaacgactgatttgacgatatcaccggcagctacggcctggatatcaaa
gacatcgttgtggactgcctgacctttcccgatctctactggccaggaagaaaccaggcgagatggcattgaaaccatcgaagccatccgcgagctgaag
aagctctaccagaaatccacaccacccctgggtctgtccaacatttccttcggcctgaaccctgcctgcacgccaggcttcttaactctgtgttcctcaat
gagtgcattgaggctggtctggactctgcgattgcgcacagctccaagatttttgccgatgaacgcattgatgatcgccagcgcgaagtggcgttggat
atggtctatgatcgccgcaccgaggattacgatccgctgcaggaattcatgcagctgtttgagggcgtttctgctgccgatgccaaggatgctcgcgct
gaacagctggccgctatgcctttgtttgagcgtttggcacagcgcatcatcgacggcgataagaatggccttgaggatgatctggaagcaggcatgaag
gagaagtctcctattgcgatcatcaacgaggacctttctcaacggcatgaagaccgtgggtgagctgtttggttccggacagatgcagctgccattcgtg
ctgcaatcggcagaaaccatgaaaactgcggtggcctatttggaaccgttcatggaagaggaagcagaagctaccggatctgcgcaggcagagggcaag
ggcaaaatcgtcgtggccaccgtcaagggtgacgtgcacgatatcggcaagaaccttgtggacatcattttgtccaacaacggttacgacgtggtgaac
ttgggcatcaagcagccactgtccgccatgttggaagcagcggaagaacacaaagcagacgtcatcggcatgtcgggacttcttgtgaagtccaccgtg
gtgatgaaggaaaaccttgaggagatgaacaacgccggcgcatccaattacccagtcattttgggtggcgctgcgctgacgcgtacctacgtggaaaac
gatctcaacgaggtgtacaccggtgaggtgtactacgcccgcgatgcttttcgagggcctgcgcctgatggatgaggtgatggcagaaaagcgtggtgaa
ggacttgatcccaactcaccagaagctattgagcaggcgaagaagaaggcggaacgtaaggctcgtaatgagcgtttcccgcaagattgccgcggagcgt
aaagctaatgcggctcccggtgattgttccggagcgttctgatgttccaccgatacttcaacccgcggcaccaccgttctgggaacccgcattgtcaag
ggtctgcccttggcggagttcttgggcaaccttgatgagcgcgcgcttgttcatggggcagtgggggtctgaaatccaccgcggcaacgagggtccaagc
tatgaggatttggtggaaactgaaggcccgaccacgcctgcgctactggctggatcgcctgaagtctgagggcattttggaccacgtggccttggtgtat
ggctacttcccagcggtcgcggaaggcgatgacgtggtgatcttggaatctcccggatccacacgcagcccgaacgcatgcgctttagcttcccacgccag
cagcgcggcaggttcttgtgcatcgcggatttcattcgcccacgcgagcaagcgtgcaaggacggcaagtggacgtcatgccattccagctggtcacc
atgggtaatcctattgctgatttcgccaacgagttgttcgcagccaatgaataccgcgagtacttggaagttcacggcatcggcgtgcagctcaccgaa
gcattggccgagtactggcactcccgagtgcgcagcgaactcaagctgaacgacggtggatctgtcgctgattttgatccagaagacaagaccaagttc
ttcgacctggattacccgcggcgcccgcttctcctttggttacggttcttgccctgatctggaagacccgcgcaaagctggtggaattgctcgagcccaggc
cgtatcggcgtggagttgtccgaggaactccagctgcacccagagcagtcccacagacgcgtttgtgctctaccacccagaggcaaagtactttaacgtc
taa

Figure 8 a) SEQ ID No. 22:

MSTSVTSPAHNNAHSSEFLDALANHVLIGDGAMGTQLQGFDLDVEKDFLDLEGCNEILNDTRPDVLRQIHRAYFEAGADLVETNTLGCNLPNLADYDIA
DRCRELAYKGTAVAREVADEMGPGRNGMRRFVVGSLGPGTKLPSLGHAPYADLRGHYKEAALGIIDGGGDAFLIETAQDLLQVKAAVHGVQDAMAELDT
FLPIICHVTVETTGTMLMGSEIGAALTALQPLGIDMIGLNCATGPDEMSEHLRYLSKHADIPVSVMPNAGLPVLGKNGAEYPLEAEDLAQALAGFVSEY
GLSMVGGCCGTTPEHIRAVRDAVVGVPEQETSTLTKIPAGPVEQASREVEKEDSVASLYTSVPLSQETGISMIGERTNSNGSKAFREAMLSGDWEKCVD
IAKQQTRDGAHMLDLCVDYVGRDGTADMATLAALLATSSTLPIMIDSTEPEVIRTGLEHLGGRSIVNSVNFEDGDGPESRYQRIMKLVKQHGAAVVALT
IDEEGQARTAEHKVRIAERLIDDITGSYGLDIKDIVVDCLTFPISTGQEETRRDGIETIEAIRELKKLYPEIHTTLGLSNISFGLNPAARQVLNSVFLN
ECIEAGLDSAIAHSSKILPMNRIDDRQREVALDMVYDRRTEDYDPLQEFMQLFEGVSAADAKDARAEQLAAMPLPERLAQRIIDGDRNGLEDDLEAGMK
EKSPIAIINEDLLNGMKTVGELFGSGQMQLPFVLQSAETMKTAVAYLEPFMEEEAEATGSAQAEGKGKIVVATVKGDVHDIGKNLVDIILSNNGYDVVN
LGIKQPLSAMLEAAEEHKADVIGMSGLLVKSTVVMKENLEEMNNAGASNYPVILGGAALTRTYVENDLNEVYTGEVYYARDAFEGLRLMDEVMAEKRGE
GLDPNSPEAIEQAKKEAERKARNERSRKIAAERAANAAPVIVPERSDVSTDTPTAAPPFWGTRIVKGLPLAEFLGNLDERALFMGQWGLKSTRGNEGPS
YEDLVETEGRPRLRYWLDRLKSEGILDHVALVYGYFPAVAEGDDVVILESPDPHAAERMRFSFPRQQRGRFLCIADFIRPREQAVKDGQVDVMPFQLVT
MGNPIADFANELFAANEYREYLEVHGIGVQLTEALAEYWHSRVRSELKLNDGGSVADFDPEDKTKFFDLDYRGARFSFGYGSCPDLEDRAKLVELLEPG
RIGVELSEELQLHPEQSTDAFVLYHPEAKYFNV b) SEQ ID No. 27:

atgtctacttcagttacttcaccagcccacaacaacgcacattcctccgaatttttggatgcgttggcaaaccatgtgttgatcggcgacggcgccatg
ggcacccagctccaaggctttgacctggacgtggaaaaggatttccttgatctggagggctgtaatgagattctcaacgacacccgccctgatgtgctg
aggcagattcaccgcgcctactttgaggcgggagctgacttggttgagaccaatacttttggttgcaacctgccgaacttggcggattatgacatcgct
gatcgttgccgtgagcttgcctacaagggcactgcagtggctagggaagtggctgatgagatgggcccgggccgaaacggcatgcggcgtttcgtggtt
ggttccctgggacctggaacgaagcttccatcgctgggccatgcaccgtatgcagatttgcgtggccactacaaggaagcagcgcttggcatcatcgac
ggtggtggcgatgcctttttgattgagactgctcaggacttgcttcaggtcaaggctgcggttcacggcgttcaagatgccatggctgaacttgataca
ttcttgcccattatttgccacgtcaccgtagagaccaccggcaccatgctcatgggttctgagatcggtgccgcgttgacagcgctgcagccactgggt
atcgacatgattggtctgaactgcgccaccggcccagatgagatgagcgagcacctgcgttacctgtccaagcacgccgatattcctgtgtcggtgatg
cctaacgcaggtcttcctgtcctgggtaaaaacggtgcagaatacccacttgaggctgaggatttggcgcaggcgctggctggattcgtctccgaatat
ggcctgtccatggtgggtggttgttgtggcaccacacctgagcacatccgtgcggtccgcgatgcggtggttggtgttccagagcaggaaacctccaca
ctgaccaagatccctgcaggccctgttgagcaggcctcccgcgaggtggagaaagaggactccgtcgcgtcgctgtacacctcggtgccattgtcccag
gaaaccggcatttccatgatcggtgagcgcaccaactccaacggttccaaggcattccgtgaggcaatgctgtctggcgattgggaaaagtgtgtggat
attgccaagcagcaaacccgcgatggtgcacacatgctggatctttgtgtggattacgtgggacgagacggcaccgccgatatggcgaccttggcagca
cttcttgctaccagctccactttgccaatcatgattgactccaccgagccagaggttattcgcacaggccttgagcacttgggtggacgaagcatcgtt
aactccgtcaactttgaagacggcgatggccctgagtcccgctaccagcgcatcatgaaactggtaaagcagcacggtgcggccgtggttgcgctgacc

Figure 8 cont.

attgatgaggaaggccaggcacgtaccgctgagcacaaggtgcgcattgctaaacgactgattgacgatatcaccggcagctacggcctggatatcaaa
gacatcgttgtggactgcctgaccttcccgatctctactggccaggaagaaaccaggcgagatggcattgaaaccatcgaagccatccgcgagctgaag
aagctctacccagaaatccacaccaccctgggtctgtccaatatttccttcggcctgaaccctgctgcacgccaggttcttaactctgtgttcctcaat
gagtgcattgaggctggtctggactctgcgattgcgcacagctccaagatttgccgatgaaccgcattgatgatcgccagcgcgaagtggcgttggat
atggtctatgatcgccgcaccgaggattacgatccgctgcaggaattcatgcagctgtttgagggcgtttctgctgccgatgccaaggatgctcgcgct
gaacagctggccgctatgcctttgtttgagcgtttggcacagcgcatcatcgacggcgataagaatggccttgaggatgatctggaagcaggcatgaag
gagaagtctcctattgcgatcatcaacgaggaccttctcaacggcatgaagaccgtgggtgagctgtttggttccggacagatgcagctgccattcgtg
ctgcaatcggcagaaaccatgaaaactgcggtggcctatttggaaccgttcatggaagaggaagcagaagctaccggatctgcgcaggcagagggcaag
ggcaaaatcgtcgtggccaccgtcaagggtgacgtgcacgatatcggcaagaacttggtggacatcattttgtccaacaacggttacgacgtggtgaac
ttgggcatcaagcagccactgtccgccatgttggaagcagcggaagaacacaaagcagacgtcatcggcatgtcgggacttcttgtgaagtccaccgtg
gtgatgaaggaaaaccttgaggagatgaacaacgccggcgcatccaattacccagtcattttgggtggcgctgcgctgacgcgtacctacgtggaaaac
gatctcaacgaggtgtacaccggtgaggtgtactacgcccgtgatgctttcgagggcctgcgcctgatggatgaggtgatggcagaaaagcgtggtgaa
ggacttgatcccaactcaccagaagctattgagcaggcgaagaagaaggcggaacgtaaggctcgtaatgagcgttcccgcaagattgccgcggagcgt
aaagctaatgcggctcccgtgattgttccggagcgttctgatgtctccaccgatactccaaccgcggcaccacggttctgggaacccgcattgtcaag
ggtctgcccttggcggagttcttgggcaaccttgatgagcgcgccttgttcatggggcagtggggtctgaaatccacccgcggcaacgagggtccaagc
tatgaggatttggtggaaactgaaggccgaccacgcctgcgctactggctggatcgcctgaagtctgagggcattttggaccacgtggccttggtgtat
ggctacttcccagcggtcgcggaaggcgatgacgtggtgatcttggaatccccggatccacacgcagccgaacgcatgcgctttagcttcccacgccag
cagcgcggcaggttcttgtgcatcgcggatttcattcgcccacgcgagcaagctgtcaaggacggccaagtggacgtcatgccattccagctggtcacc
atgggtaatcctattgctgatttcgccaacgagttgttcgcagccaatgaatacccgagtacttggaagttcacggcatcggcgtgcagctcaccgaa
gcattggccgagtactggcactcccgagtgcgcagcgaactcaagctgaacgacggtggatctgtcgctgattttgatccagaagacaagaccaagttc
ttcgacctggattacgcgggcgcccgcttctcctttggttacggttcttgccctgatctggaagaccgcgcaaagctggtggaattgctcgagcccaggc
cgtatcggcgtggagttgtccgaggaactccagctgcacccagagcagtccacagacgcgtttgtgctctaccacccagaggcaaagtactttaacgtc
taa

Figure 9 a) SEQ ID No. 22:

MSTSVTSPAHNNAHSSEFLDALANHVLIGDGAMGTQLQGFDLDVEKDFLDLEGCNEILNDTRPDVLRQIHRAYFEAGADLVETNTFGCNLPNLADYDIA
DHCRELAYKGTAVAREVADEMGPGRNGMRRFVVGNLGPGTKLPSLGHAPYADLRGHYKEAALGIIDGGGDAFLIETAQDLLQVKAAVHGVQDAMAELDT
FLPIICHVTVETTGTMLMGSEIGAALTALQPLGIDMIGLNCATGPDEMSEHLRYLSKHADIPVSVMPNAGLPVLGKNGAEYPLEAEDLAQALAGFVSEY
GLSMVGGCCGTTPEHIRAVRDAVVGVPEQETSTLTKIPAGPVEQASREVEKEDSVASLYTSVPLSQETGISMIGERTNSNGSKAFREAMLSGDWEKCVD
IAKQQTRDGAHMLDLCVDYVGRDGTADMATLAALLATSSTLPIMIDSTEPEVIRTGLEHLGGRSIVNSVNFEDGDGPESRYQRIMKLVKQHGAAVVALT
IDEEGQARTAEKKVRIAKRLIDDITGSYGLDIKDIVVDCLTFPISTGQEETRRDGIETIEAIRELKKLYPEIHTTLGLSNISFGLNPAARQVLNSVFLN
ECIEAGLDSAIAHSSKILPMNRIDDRQREVALDMVYDRRTEDYDPLQEFMQLFEGVSAADAKDARAEQLAAMPLFERLAQRIIDGDKNGLEDDLEAGMK
EKSPIAIINEDLLNGMKTVGELFGSGQMQLPFVLQSAETMKTAVAYLEPFMEEEAEATGSAQAEGKGKIVVATVKGDVHDIGKNLVDIILSNNGYDVVN
LGIKQPLSAMLEAAEEHKADVIGMSGLLVKSTVVMKENLEEMNNAGASNYPVILGGAALTRTYVENDLNEVYTGEVYYARDAFEGLRLMDEVMAEKRGE
GLDPNSPEAIRQAEEKAERRAPMERSRKIAAERKANAAPVIVPERSDVSTDTPTAAPPWGTRIVEGLPLAEPLGNLDERALFMGQWGLKSTPGNEGPS
YEDLVETEGRPRLRYWLDRLKSEGILDHVALVYGYFPAVAEGDDVVILESPDPHAAERMRFSFPRQQRGRFLCIADFIRPREQAVKDGQVDVMPFQLVT
MGNPIADFANELFAANEYREYLEVHGIGVQLTEALAEYWHSRVRSELKLNDGGSVADFDPEDKTKFFDLDYRGARFSFGYGSCPDLEDRAKLVELLEPG
RIGVELSEELQLHPEQSTDAFVLYHPEAKYFNV b) SEQ ID No. 58.

atgtctacttcagttacttcaccagcccacaacaacgcacattcctccgaatttttggatgcgttggcaaaccatgtgttgatcggcgacggcgccatg
ggcacccagctccaaggctttgacctggacgtggaaaaggatttccttgatctggaggggtgtaatgagattctcaacgacacccgccctgatgtgttg
aggcagattcaccgcgcctactttgaggcgggagctgacttggttgagaccaatacttttggttgcaacctgccgaacttggcggattatgacatcgct
gatcattgccgtgagcttgcctacaagggcactgcagtggctagggaagtggctgatgagatgggcccgggccgaaacggcatgcggcgtttcgtggtt
ggttccctgggacctggaacgaagcttccatcgctgggccatgccccgtatgcagatttgcgtgggcactacaaggaagcagcgcttggcatcatcgac
ggtggtggcgatgcctttttgattgagactgctcaggacttgcttcaggtcaaggctgcggttcacggcgttcaagatgccatggctgaacttgataca
ttcttgcccattatttgctacgtcaccgtagagaccacgggcaccatgctcatgggttctgagatcggtgccgcgttgacagcgctgcagccactgggt
atcgacatgattggtctgaactgcgccaccggcccagatgagatgagcgagcacctgcgttacctgtccaagcacgccgatattcctgtgtcggtgatg
cctaacgcaggtcttcctgtcctgggtaaaaacggtgcagaatacccacttgaggctgaggatttggcgcaggcgctggctggattcgtctccgaatat
ggcctgtccatggtgggtggttgttgtggcaccacacctgagcacatccgtgcggtccgcgatgcggtggttggtgttccagagcaggaaacctccacc
ctgaccaagatccctgcaggccctgttgagcaggcctcccgcgaggtggagaaagaggactccgtcgcgtcgctgtacacctcggtgccattgtcccag
gaaacgggcatttccatgatcggtgagcgcaccaactccaacggttccaaggcgttccgtgaggcaatgctgtctggcgattgggaaaagtgtgtggat
attgccaagcagcaaacccgcgatggtgcacacatgctggatctttgtgtggattacgtgggacgagatggcaccgcggatatggcgaccttggcagca
cttcttgctaccagctccactttgccaatcatgattgactccaccgagccagaggttattcgcacaggccttgagcacttgggtggacgaagcatcgtt
aactcggtcaactttgaagacggcgatggccctgagtcccgctaccagcgcatcatgaaactggtaaagcagcacggtgcggccgtggttgcgctgacc

Figure 9 cont.

attgatgaggaaggccaggcacgtaccgctgagcacaaggtgcgcattgctaaacgactgattgacgatatcacgggcagctacggcctggatatcaaa
gacatcgttgtggactgcctgaccttcccgatctctactggccaggaagaaaccaggcgagatggcattgaaaccatcgaagccatccggcgagctgaag
aagctctacccagaaatccacaccacctgggtctgtccaatatttccttcggccttgaacctgctgcacgccaggttcttaactctgtgttcctcaat
gagtgcattgaggctggtctggactctgcgattgcgcacagctccaagattttgccgatgaacgcattgatgatcgccagcgcgaagtggcgttggat
atggtctatgatcgccgcaccgaggattacgatccgctgcaggaattcatgcagctgtttgagggcgttttctgctgccgatgccaaggatgctcgcgct
gaacagctggccgctatgcctttgtttgagcgtttggcacagcgcatcatcgacggcgataagaatggccttgaggatgatctggaagcaggcatgaag
gagaagtctcctattgcgatcatcaacgaggaccttctcaacggcatgaagacgcgtgggtgagctgtttggttccggacagatgcagctgccattcgtg
ctgcaatcggcagaaaccatgaaaactgcggtggcctatttggaaccgttcatggaagaggaagcagaagctaccggatctgcgcaggcagagggcaag
ggcaaaatcgtcgtggccacgtcaagggtgacgtgcacgatatcggcaagaacttggtggacatcatttgtccaacaacggttacgacgtggtgaac
ttgggcatcaagcagccactgtccgccatgttggaagcagcggaagaacacaaagcagacgtcatcggcatgtcgggacttcttgtgaagtccaccgtg
gtgatgaaggaaaaccttgaggagatgaacaacgcgggcgcatccaattacccagtcatttgggtggcgctgcgctgacgcgtacctacgtggaaaac
gatctcaacgaggtgtacaccggtgaggtgtactacgccgtgatgctttcgagggcctgcgctgatggatgaggtgatggcagaaagcgtggtgaa
ggacttgatcccaactcaccagaagctattgagcaggcgaagaagaaggcggaacgtaaggctcgtaatgagcgttcccgcaagattgcccgcgagcgt
aaagctaatgcggctcccgtgattgttccggagcgttctgatgtctccaccgatactccaaccgcggcaccaccgttctggggaaccccgcattgtcaag
ggtctgcccttggcggagttcttgggcaaccttgatgagcgcgccttgttcatgggcagtggggtctgaaatccacccgcggcaacgagggtccaagc
tatgaggatttggtggaaactgaaggccgaccacgcctgcgctactggctggatcgcctgaagtctgagggcatttggaccacgtggccttggtgtat
ggctacttcccagcggtcgcggaaggcgatgacgtggtgatcttggaatccccggatccacacgcagccgaacgcatgcgctttagcttcccacgccag
cagcgcggcaggttcttgtgcatcgcggatttcattcgcccacgcgagcaagctgtcaaggacggccaagtggacgtcatgccattccagctggtcacc
atgggtaatcctattgctgatttcgccaacgagttgttcgcagccaatgaatacccgcagtacttggaagttcacggcatcggcgtgcagctcaccgaa
gcattggcccgagtactggcactcccgagtgcgcagcgaactcaagctgaacgacggtggatctgtcgctgatttgatccagaagacaagaccaagttc
ttcgacctggattacgcggcgcccgcttctcctttggttacggttcttgccctgatctggaagaccgcgcaaagctggtggaattgctcgagccaggc
cgtatcggcgtggagttgtccgaggaactccagctgcacccagagcagtcccacagacgcgtttgtgctctacccaccagaggcaaagtactttaacgtc
taa

SEQUENCE LISTING

```
<160> NUMBER OF SEQ ID NOS: 32

<210> SEQ ID NO 1
<211> LENGTH: 1221
<212> TYPE: PRT
<213> ORGANISM: Corynebacterium glutamicum
<220> FEATURE:
<221> NAME/KEY: misc_feature
<223> OTHER INFORMATION: methionine synthase MetH

<400> SEQUENCE: 1

Met Ser Thr Ser Val Thr Ser Pro Ala His Asn Asn Ala His Ser Ser
1               5                   10                  15

Glu Phe Leu Asp Ala Leu Ala Asn His Val Leu Ile Gly Asp Gly Ala
            20                  25                  30

Met Gly Thr Gln Leu Gln Gly Phe Asp Leu Asp Val Glu Lys Asp Phe
        35                  40                  45
```

```
Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
65                  70                  75                  80

Val Glu Thr Asn Thr Phe Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
            340                 345                 350

Ala Ser Leu Tyr Thr Ser Val Pro Leu Ser Gln Glu Thr Gly Ile Ser
        355                 360                 365

Met Ile Gly Glu Arg Thr Asn Ser Asn Gly Ser Lys Ala Phe Arg Glu
    370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
            420                 425                 430

Thr Ser Ser Thr Leu Pro Ile Met Ile Asp Ser Thr Glu Pro Glu Val
        435                 440                 445

Ile Arg Thr Gly Leu Glu His Leu Gly Gly Arg Ser Ile Val Asn Ser
    450                 455                 460

Val Asn Phe Glu Asp Gly Asp Gly Pro Glu Ser Arg Tyr Gln Arg Ile
465                 470                 475                 480
```

```
Met Lys Leu Val Lys Gln His Gly Ala Ala Val Val Ala Leu Thr Ile
                485                 490                 495

Asp Glu Glu Gly Gln Ala Arg Thr Ala Glu His Lys Val Arg Ile Ala
            500                 505                 510

Lys Arg Leu Ile Asp Asp Ile Thr Gly Ser Tyr Gly Leu Asp Ile Lys
        515                 520                 525

Asp Ile Val Val Asp Cys Leu Thr Phe Pro Ile Ser Thr Gly Gln Glu
    530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575

Ser Phe Gly Leu Asn Pro Ala Ala Arg Gln Val Leu Asn Ser Val Phe
            580                 585                 590

Leu Asn Glu Cys Ile Glu Ala Gly Leu Asp Ser Ala Ile Ala His Ser
        595                 600                 605

Ser Lys Ile Leu Pro Met Asn Arg Ile Asp Asp Arg Gln Arg Glu Val
    610                 615                 620

Ala Leu Asp Met Val Tyr Asp Arg Arg Thr Glu Asp Tyr Asp Pro Leu
625                 630                 635                 640

Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Glu Ala Glu Ala Thr Gly
            740                 745                 750

Ser Ala Gln Ala Glu Gly Lys Gly Lys Ile Val Val Ala Thr Val Lys
        755                 760                 765

Gly Asp Val His Asp Ile Gly Lys Asn Leu Val Asp Ile Ile Leu Ser
    770                 775                 780

Asn Asn Gly Tyr Asp Val Val Asn Leu Gly Ile Lys Gln Pro Leu Ser
785                 790                 795                 800

Ala Met Leu Glu Ala Ala Glu Glu His Lys Ala Asp Val Ile Gly Met
                805                 810                 815

Ser Gly Leu Leu Val Lys Ser Thr Val Val Met Lys Glu Asn Leu Glu
            820                 825                 830

Glu Met Asn Asn Ala Gly Ala Ser Asn Tyr Pro Val Ile Leu Gly Gly
        835                 840                 845

Ala Ala Leu Thr Arg Thr Tyr Val Glu Asn Asp Leu Asn Glu Val Tyr
    850                 855                 860

Thr Gly Glu Val Tyr Tyr Ala Arg Asp Ala Phe Glu Gly Leu Arg Leu
865                 870                 875                 880

Met Asp Glu Val Met Ala Glu Lys Arg Gly Glu Gly Leu Asp Pro Asn
                885                 890                 895

Ser Pro Glu Ala Ile Glu Gln Ala Lys Lys Lys Ala Glu Arg Lys Ala
```

```
            900                 905                 910

Arg Asn Glu Arg Ser Arg Lys Ile Ala Ala Glu Arg Lys Ala Asn Ala
        915                 920                 925

Ala Pro Val Ile Val Pro Glu Arg Ser Asp Val Ser Thr Asp Thr Pro
    930                 935                 940

Thr Ala Ala Pro Pro Phe Trp Gly Thr Arg Ile Val Lys Gly Leu Pro
945                 950                 955                 960

Leu Ala Glu Phe Leu Gly Asn Leu Asp Glu Arg Ala Leu Phe Met Gly
                965                 970                 975

Gln Trp Gly Leu Lys Ser Thr Arg Gly Asn Glu Gly Pro Ser Tyr Glu
            980                 985                 990

Asp Leu Val Glu Thr Glu Gly Arg  Pro Arg Leu Arg Tyr  Trp Leu Asp
        995                 1000                1005

Arg Leu  Lys Ser Glu Gly Ile  Leu Asp His Val Ala  Leu Val Tyr
    1010                1015                1020

Gly Tyr  Phe Pro Ala Val Ala  Glu Gly Asp Asp Val  Val Ile Leu
    1025                1030                1035

Glu Ser  Pro Asp Pro His Ala  Ala Glu Arg Met Arg  Phe Ser Phe
    1040                1045                1050

Pro Arg  Gln Gln Arg Gly Arg  Phe Leu Cys Ile Ala  Asp Phe Ile
    1055                1060                1065

Arg Pro  Arg Glu Gln Ala Val  Lys Asp Gly Gln Val  Asp Val Met
    1070                1075                1080

Pro Phe  Gln Leu Val Thr Met  Gly Asn Pro Ile Ala  Asp Phe Ala
    1085                1090                1095

Asn Glu  Leu Phe Ala Ala Asn  Glu Tyr Arg Glu Tyr  Leu Glu Val
    1100                1105                1110

His Gly  Ile Gly Val Gln Leu  Thr Glu Ala Leu Ala  Glu Tyr Trp
    1115                1120                1125

His Ser  Arg Val Arg Ser Glu  Leu Lys Leu Asn Asp  Gly Gly Ser
    1130                1135                1140

Val Ala  Asp Phe Asp Pro Glu  Asp Lys Thr Lys Phe  Phe Asp Leu
    1145                1150                1155

Asp Tyr  Arg Gly Ala Arg Phe  Ser Phe Gly Tyr Gly  Ser Cys Pro
    1160                1165                1170

Asp Leu  Glu Asp Arg Ala Lys  Leu Val Glu Leu Leu  Glu Pro Gly
    1175                1180                1185

Arg Ile  Gly Val Glu Leu Ser  Glu Glu Leu Gln Leu  His Pro Glu
    1190                1195                1200

Gln Ser  Thr Asp Ala Phe Val  Leu Tyr His Pro Glu  Ala Lys Tyr
    1205                1210                1215

Phe Asn  Val
    1220


<210> SEQ ID NO 2
<211> LENGTH: 245
<212> TYPE: PRT
<213> ORGANISM: Corynebacterium glutamicum
<220> FEATURE:
<221> NAME/KEY: DOMAIN
<222> LOCATION: (1)..(245)
<223> OTHER INFORMATION: homocysteine binding domain of methionine
      synthase MetH

<400> SEQUENCE: 2

Met Ser Thr Ser Val Thr Ser Pro Ala His Asn Asn Ala His Ser Ser
1               5                   10                  15
```

```
Glu Phe Leu Asp Ala Leu Ala Asn His Val Leu Ile Gly Asp Gly Ala
            20                  25                  30

Met Gly Thr Gln Leu Gln Gly Phe Asp Leu Asp Val Glu Lys Asp Phe
        35                  40                  45

Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
65                  70                  75                  80

Val Glu Thr Asn Thr Phe Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu
                245


<210> SEQ ID NO 3
<211> LENGTH: 11
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(11)
<223> OTHER INFORMATION: /Note="methionine synthase sequence motif"
<220> FEATURE:
<221> NAME/KEY: VARIANT
<222> LOCATION: (1)..(1)
<223> OTHER INFORMATION: /replace="Val"       /replace="Arg"
<220> FEATURE:
<221> NAME/KEY: VARIANT
<222> LOCATION: (2)..(2)
<223> OTHER INFORMATION: /replace="Glu"       /replace="Arg"
<220> FEATURE:
<221> NAME/KEY: VARIANT
<222> LOCATION: (3)..(3)
<223> OTHER INFORMATION: /replace="Ala"       /replace="Gln"
<220> FEATURE:
<221> NAME/KEY: VARIANT
<222> LOCATION: (4)..(4)
<223> OTHER INFORMATION: /replace="Leu"       /replace="Val"
<220> FEATURE:
<221> NAME/KEY: VARIANT
<222> LOCATION: (5)..(5)
<223> OTHER INFORMATION: /replace="Arg"       /replace="Ser"
<220> FEATURE:
<221> NAME/KEY: VARIANT
<222> LOCATION: (6)..(6)
```

<223> OTHER INFORMATION: /replace="Glu" /replace="Ala"
/replace="Lys"
<220> FEATURE:
<221> NAME/KEY: VARIANT
<222> LOCATION: (7)..(7)
<223> OTHER INFORMATION: /replace="Gln" /replace="Leu"
<220> FEATURE:
<221> NAME/KEY: VARIANT
<222> LOCATION: (9)..(9)
<223> OTHER INFORMATION: /replace="Asn" /replace="Ser"
<220> FEATURE:
<221> NAME/KEY: VARIANT
<222> LOCATION: (10)..(10)
<223> OTHER INFORMATION: /replace="Thr" /replace="Glu"
<220> FEATURE:
<221> NAME/KEY: VARIANT
<222> LOCATION: (11)..(11)
<223> OTHER INFORMATION: /replace="Arg"
<220> FEATURE:
<221> NAME/KEY: MISC_FEATURE
<222> LOCATION: (1)..(7),(9)..(11)
<223> OTHER INFORMATION: /note="residues given in the sequence have
no preference with respect to those in the annotations for said
positions'"

<400> SEQUENCE: 3

Ser Ser Glu Phe Leu Asp Ala Leu Ala Asn His
1 5 10

<210> SEQ ID NO 4
<211> LENGTH: 15
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(15)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Ile"
<220> FEATURE:
<221> NAME/KEY: VARIANT
<222> LOCATION: (2)..(2)
<223> OTHER INFORMATION: /replace="Leu"
<220> FEATURE:
<221> NAME/KEY: VARIANT
<222> LOCATION: (3)..(3)
<223> OTHER INFORMATION: /replace="Val" /replace="Leu"
<220> FEATURE:
<221> NAME/KEY: VARIANT
<222> LOCATION: (4)..(4)
<223> OTHER INFORMATION: /replace="Ala" /replace="Leu"
<220> FEATURE:
<221> NAME/KEY: VARIANT
<222> LOCATION: (7)..(7)
<223> OTHER INFORMATION: /replace="Gly"
<220> FEATURE:
<221> NAME/KEY: VARIANT
<222> LOCATION: (8)..(8)
<223> OTHER INFORMATION: /replace="Tyr"
<220> FEATURE:
<221> NAME/KEY: VARIANT
<222> LOCATION: (11)..(11)
<223> OTHER INFORMATION: /replace="Met" /replace="Glu"
<220> FEATURE:
<221> NAME/KEY: VARIANT
<222> LOCATION: (12)..(12)
<223> OTHER INFORMATION: /replace="Ile" /replace="Phe"
<220> FEATURE:
<221> NAME/KEY: VARIANT
<222> LOCATION: (13)..(13)
<223> OTHER INFORMATION: /replace="Met"
<220> FEATURE:
<221> NAME/KEY: VARIANT
<222> LOCATION: (14)..(14)

```
<223> OTHER INFORMATION: /replace="Ala"       /replace="Ser"
      /replace="Lys"
<220> FEATURE:
<221> NAME/KEY: VARIANT
<222> LOCATION: (15)..(15)
<223> OTHER INFORMATION: /replace="Gln"       /replace="Tyr"
<220> FEATURE:
<221> NAME/KEY: MISC_FEATURE
<222> LOCATION: (1)..(4),(7)..(8),(11)..(15)
<223> OTHER INFORMATION: /note="residues given in the sequence have no
      preference with respect to those in the annotations for said
      positions"

<400> SEQUENCE: 4

Val Val Ile Gly Asp Gly Ala Met Gly Thr Gln Leu Gln Gly Phe
1               5                   10                  15


<210> SEQ ID NO 5
<211> LENGTH: 15
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(15)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Pro"       /replace="Tyr"
<220> FEATURE:
<221> NAME/KEY: VARIANT
<222> LOCATION: (2)..(2)
<223> OTHER INFORMATION: /replace="Thr"       /replace="Asn"
<220> FEATURE:
<221> NAME/KEY: VARIANT
<222> LOCATION: (3)..(3)
<223> OTHER INFORMATION: /replace="Leu"       /replace="Asp"
      /replace="Glu"
<220> FEATURE:
<221> NAME/KEY: VARIANT
<222> LOCATION: (4)..(4)
<223> OTHER INFORMATION: /replace="Asp"       /replace="Ala"
      /replace="Leu"
<220> FEATURE:
<221> NAME/KEY: VARIANT
<222> LOCATION: (5)..(5)
<223> OTHER INFORMATION: /replace="Asp"       /replace="Pro"
<220> FEATURE:
<221> NAME/KEY: MISC_FEATURE
<222> LOCATION: (6)..(6)
<223> OTHER INFORMATION: /note="no amino acid at this position in
      microorganisms T. maritima, C. glutamicum, Str. coelicolor"
<220> FEATURE:
<221> NAME/KEY: MISC_FEATURE
<222> LOCATION: (7)..(7)
<223> OTHER INFORMATION: /note="no amino acid at this position in
      microorganisms T. maritima, C. glutamicum, Str. coelicolor"
<220> FEATURE:
<221> NAME/KEY: MISC_FEATURE
<222> LOCATION: (8)..(8)
<223> OTHER INFORMATION: /note="no amino acid at this position in
      microorganisms T. maritima, C. glutamicum, Str. coelicolor"
<220> FEATURE:
<221> NAME/KEY: MISC_FEATURE
<222> LOCATION: (9)..(9)
<223> OTHER INFORMATION: /note="no amino acid at this position in
      microorganisms T. maritima, C. glutamicum, Str. coelicolor"
<220> FEATURE:
<221> NAME/KEY: MISC_FEATURE
<222> LOCATION: (10)..(10)
<223> OTHER INFORMATION: /note="no amino acid at this position in
      microorganisms T. maritima, C. glutamicum, Str. coelicolor"
<220> FEATURE:
<221> NAME/KEY: MISC_FEATURE
<222> LOCATION: (11)..(11)
<223> OTHER INFORMATION: /note="no amino acid at this position in
```

```
      microorganisms T. maritima, C. glutamicum, Str. coelicolor"
<220> FEATURE:
<221> NAME/KEY: MISC_FEATURE
<222> LOCATION: (12)..(12)
<223> OTHER INFORMATION: /note="no amino acid at this position in
      microorganisms T. maritima, C. glutamicum, Str. coelicolor"
<220> FEATURE:
<221> NAME/KEY: MISC_FEATURE
<222> LOCATION: (13)..(13)
<223> OTHER INFORMATION: /note="no amino acid at this position in
      microorganisms T. maritima, C. glutamicum, Str. coelicolor"
<220> FEATURE:
<221> NAME/KEY: VARIANT
<222> LOCATION: (14)..(14)
<223> OTHER INFORMATION: /replace="Trp"
<220> FEATURE:
<221> NAME/KEY: MISC_FEATURE
<222> LOCATION: (14)..(14)
<223> OTHER INFORMATION: /note="no amino acid at this position in
      microorganism T. maritima"
<220> FEATURE:
<221> NAME/KEY: VARIANT
<222> LOCATION: (15)..(15)
<223> OTHER INFORMATION: /replace="Pro"
<220> FEATURE:
<221> NAME/KEY: MISC_FEATURE
<222> LOCATION: (15)..(15)
<223> OTHER INFORMATION: /note="no amino acid at this position in
      microorganism T. maritima"
<220> FEATURE:
<221> NAME/KEY: MISC_FEATURE
<222> LOCATION: (1)..(15)
<223> OTHER INFORMATION: /note="residues given in the sequence have
      no preference with respect to those in the annotations for
      said positions"

<400> SEQUENCE: 5

Leu Asp Val Glu Lys Phe Arg Gly Glu Arg Phe Ala Asp Asp Phe
1               5                   10                  15


<210> SEQ ID NO 6
<211> LENGTH: 17
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(17)
<223> OTHER INFORMATION: /note="methionine synthase sequence motif"
<220> FEATURE:
<221> NAME/KEY: VARIANT
<222> LOCATION: (2)..(2)
<223> OTHER INFORMATION: /replace="Val"
<220> FEATURE:
<221> NAME/KEY: VARIANT
<222> LOCATION: (3)..(3)
<223> OTHER INFORMATION: /replace="Leu"       /replace="Ile"
<220> FEATURE:
<221> NAME/KEY: VARIANT
<222> LOCATION: (4)..(4)
<223> OTHER INFORMATION: /replace="Ser"       /replace="Lys"
<220> FEATURE:
<221> NAME/KEY: VARIANT
<222> LOCATION: (5)..(5)
<223> OTHER INFORMATION: /replace="Lys"       /replace="Ala"
<220> FEATURE:
<221> NAME/KEY: VARIANT
<222> LOCATION: (7)..(7)
<223> OTHER INFORMATION: /replace="Glu"
<220> FEATURE:
<221> NAME/KEY: VARIANT
<222> LOCATION: (8)..(8)
<223> OTHER INFORMATION: /replace="Ile"
<220> FEATURE:
<221> NAME/KEY: VARIANT
<222> LOCATION: (9)..(9)
<223> OTHER INFORMATION: /replace="Val"       /replace="Ile"
```

```
<220> FEATURE:
<221> NAME/KEY: VARIANT
<222> LOCATION: (10)..(10)
<223> OTHER INFORMATION: /replace="Ala"      /replace="Leu"
<220> FEATURE:
<221> NAME/KEY: VARIANT
<222> LOCATION: (11)..(11)
<223> OTHER INFORMATION: /replace="Ser"      /replace="Ala"
      /replace="Lys"
<220> FEATURE:
<221> NAME/KEY: VARIANT
<222> LOCATION: (12)..(12)
<223> OTHER INFORMATION: /replace="Val"
<220> FEATURE:
<221> NAME/KEY: VARIANT
<222> LOCATION: (14)..(14)
<223> OTHER INFORMATION: /replace="Glu"      /replace="Asn"
<220> FEATURE:
<221> NAME/KEY: VARIANT
<222> LOCATION: (15)..(15)
<223> OTHER INFORMATION: /replace="Glu"      /replace="Ser"
<220> FEATURE:
<221> NAME/KEY: VARIANT
<222> LOCATION: (17)..(17)
<223> OTHER INFORMATION: /replace="Ile"
<220> FEATURE:
<221> NAME/KEY: MISC_FEATURE
<222> LOCATION: (2)..(5),(7)..(12),(14)..(15),(17)
<223> OTHER INFORMATION: /note="residues given in the sequence have
      no preference with respect to those in the annotations for
      said positions"

<400> SEQUENCE: 6

Leu Asn Asp Thr Arg Pro Asp Val Leu Arg Gln Ile His Arg Ala Tyr
1               5                   10                  15

Phe


<210> SEQ ID NO 7
<211> LENGTH: 15
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(15)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Ala"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (4)..(4)
<223> OTHER INFORMATION: /replace="Val"      /replace="Ser"
<220> FEATURE:
<221> NAME/KEY: VARIANT
<222> LOCATION: (6)..(6)
<223> OTHER INFORMATION: /replace="Cys"      /replace="Ile"
      /replace="Val"
<220> FEATURE:
<221> NAME/KEY: VARIANT
<222> LOCATION: (7)..(7)
<223> OTHER INFORMATION: /replace="Ile"
<220> FEATURE:
<221> NAME/KEY: VARIANT
<222> LOCATION: (8)..(8)
<223> OTHER INFORMATION: /replace="Leu"
<220> FEATURE:
<221> NAME/KEY: VARIANT
<222> LOCATION: (13)..(13)
<223> OTHER INFORMATION: /replace="Asn"
<220> FEATURE:
```

```
<221> NAME/KEY: VARIANT
<222> LOCATION: (14)..(14)
<223> OTHER INFORMATION: /replace="Ala"       /replace="Ser"
<220> FEATURE:
<221> NAME/KEY: VARIANT
<222> LOCATION: (15)..(15)
<223> OTHER INFORMATION: /replace="Thr"
<220> FEATURE:
<221> NAME/KEY: MISC_FEATURE
<222> LOCATION: (1)..(2),(4),(6)..(8),(13)..(15)
<223> OTHER INFORMATION: /note="residues given in the sequence have
      no preference with respect to those in the annotations for said
      positions"

<400> SEQUENCE: 7

Glu Ala Gly Ala Asp Leu Val Glu Thr Asn Thr Phe Gly Cys Asn
1               5                   10                  15


<210> SEQ ID NO 8
<211> LENGTH: 9
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(9)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="His"       /replace="Thr"
      /replace="Arg"
<220> FEATURE:
<221> NAME/KEY: VARIANT
<222> LOCATION: (2)..(2)
<223> OTHER INFORMATION: /replace="Ser"       /replace="Ile"
      /replace="Met"
<220> FEATURE:
<221> NAME/KEY: VARIANT
<222> LOCATION: (3)..(3)
<223> OTHER INFORMATION: /replace="Ala"       /replace="Lys"
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (5)..(5)
<223> OTHER INFORMATION: /replace="Gly"       /replace="Arg"
<220> FEATURE:
<221> NAME/KEY: VARIANT
<222> LOCATION: (6)..(6)
<223> OTHER INFORMATION: /replace="Glu"       /replace="Lys"
<220> FEATURE:
<221> NAME/KEY: VARIANT
<222> LOCATION: (7)..(7)
<223> OTHER INFORMATION: /replace="His"
<220> FEATURE:
<221> NAME/KEY: VARIANT
<222> LOCATION: (8)..(8)
<223> OTHER INFORMATION: /replace="Gln"       /replace="Gly"
<220> FEATURE:
<221> NAME/KEY: VARIANT
<222> LOCATION: (9)..(9)
<223> OTHER INFORMATION: /replace="Met"       /replace="Leu"
<220> FEATURE:
<221> NAME/KEY: MISC_FEATURE
<222> LOCATION: (1)..(9)
<223> OTHER INFORMATION: /note="residues given in the sequence have
      no preference with respect to those in the annotations for
      said positions"

<400> SEQUENCE: 8

Leu Pro Asn Leu Ala Asp Tyr Asp Ile
1               5
```

```
<210> SEQ ID NO 9
<211> LENGTH: 22
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(22)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Pro"       /replace="Glu"
<220> FEATURE:
<221> NAME/KEY: VARIANT
<222> LOCATION: (2)..(2)
<223> OTHER INFORMATION: /replace="Glu"       /replace="Ser"
<220> FEATURE:
<221> NAME/KEY: VARIANT
<222> LOCATION: (3)..(3)
<223> OTHER INFORMATION: /replace="Leu"       /replace="Lys"
<220> FEATURE:
<221> NAME/KEY: VARIANT
<222> LOCATION: (4)..(4)
<223> OTHER INFORMATION: /replace="Val"       /replace="Ser"
      /replace="Leu"
<220> FEATURE:
<221> NAME/KEY: VARIANT
<222> LOCATION: (5)..(5)
<223> OTHER INFORMATION: /replace="His"       /replace="Ala"
      /replace="Asp"
<220> FEATURE:
<221> NAME/KEY: VARIANT
<222> LOCATION: (6)..(6)
<223> OTHER INFORMATION: /replace="Pro"
<220> FEATURE:
<221> NAME/KEY: VARIANT
<222> LOCATION: (7)..(7)
<223> OTHER INFORMATION: /replace="Ile"
<220> FEATURE:
<221> NAME/KEY: VARIANT
<222> LOCATION: (8)..(8)
<223> OTHER INFORMATION: /replace="Ser"       /replace="Asn"
      /replace="Val"
<220> FEATURE:
<221> NAME/KEY: VARIANT
<222> LOCATION: (9)..(9)
<223> OTHER INFORMATION: /replace="Glu"       /replace="Phe"
      /replace="Arg"
<220> FEATURE:
<221> NAME/KEY: VARIANT
<222> LOCATION: (10)..(10)
<223> OTHER INFORMATION: /replace="Ala"       /replace="Asn"
<220> FEATURE:
<221> NAME/KEY: VARIANT
<222> LOCATION: (11)..(11)
<223> OTHER INFORMATION: /replace="Ala"
<220> FEATURE:
<221> NAME/KEY: VARIANT
<222> LOCATION: (12)..(12)
<223> OTHER INFORMATION: /replace="Ala"       /replace="Val"
<220> FEATURE:
<221> NAME/KEY: VARIANT
<222> LOCATION: (13)..(13)
<223> OTHER INFORMATION: /replace="Arg"       /replace="Lys"
<220> FEATURE:
<221> NAME/KEY: VARIANT
<222> LOCATION: (14)..(14)
<223> OTHER INFORMATION: /replace="Leu"       /replace="Ile"
<220> FEATURE:
<221> NAME/KEY: VARIANT
<222> LOCATION: (17)..(17)
<223> OTHER INFORMATION: /replace="Ala"       /replace="Arg"
<220> FEATURE:
<221> NAME/KEY: VARIANT
<222> LOCATION: (18)..(18)
<223> OTHER INFORMATION: /replace="Cys"       /replace="Ala"
<220> FEATURE:
```

```
<221> NAME/KEY: VARIANT
<222> LOCATION: (20)..(20)
<223> OTHER INFORMATION: /replace="Glu"
<220> FEATURE:
<221> NAME/KEY: VARIANT
<222> LOCATION: (22)..(22)
<223> OTHER INFORMATION: /replace="Met"       /replace="Trp"
      /replace="Lys"
<220> FEATURE:
<221> NAME/KEY: MISC_FEATURE
<222> LOCATION: (1)..(14),(17)..(18),(20),(22)
<223> OTHER INFORMATION: /note="residues given in the sequence have
      no preference with respect to those in the annotations for
      said positions"

<400> SEQUENCE: 9

Ala Asp Arg Cys Arg Glu Leu Ala Tyr Lys Gly Thr Ala Val Ala Arg
1               5                   10                  15

Glu Val Ala Asp Glu Phe
            20


<210> SEQ ID NO 10
<211> LENGTH: 8
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(8)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Ala"       /replace="Arg"
<220> FEATURE:
<221> NAME/KEY: VARIANT
<222> LOCATION: (2)..(2)
<223> OTHER INFORMATION: /replace="Thr"
<220> FEATURE:
<221> NAME/KEY: VARIANT
<222> LOCATION: (3)..(3)
<223> OTHER INFORMATION: /replace="Asp"       /replace="Pro"
<220> FEATURE:
<221> NAME/KEY: VARIANT
<222> LOCATION: (4)..(4)
<223> OTHER INFORMATION: /replace="Glu"
<220> FEATURE:
<221> NAME/KEY: VARIANT
<222> LOCATION: (5)..(5)
<223> OTHER INFORMATION: /replace="Arg"       /replace="Lys"
<220> FEATURE:
<221> NAME/KEY: VARIANT
<222> LOCATION: (6)..(6)
<223> OTHER INFORMATION: /replace="Gln"       /replace="Pro"
<220> FEATURE:
<221> NAME/KEY: VARIANT
<222> LOCATION: (8)..(8)
<223> OTHER INFORMATION: /replace="Trp"       /replace="Tyr"
<220> FEATURE:
<221> NAME/KEY: MISC_FEATURE
<222> LOCATION: (1)..(8)
<223> OTHER INFORMATION: /note="no amino acid at this position in
      microorganism T. maritima"
<220> FEATURE:
<221> NAME/KEY: MISC_FEATURE
<222> LOCATION: (1)..(6),(8)
<223> OTHER INFORMATION: /note="residues given in the sequence have
      no preference with respect to those in the annotations for
      said positions"

<400> SEQUENCE: 10

Gly Arg Asn Gly Met Arg Arg Phe
1               5
```

<210> SEQ ID NO 11
<211> LENGTH: 13
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(13)
<223> OTHER INFORMATION: /note="methionine synthase sequence motif"
<220> FEATURE:
<221> NAME/KEY: VARIANT
<222> LOCATION: (2)..(2)
<223> OTHER INFORMATION: /replace="Leu" /replace="Ala" /replace="Phe"
<220> FEATURE:
<221> NAME/KEY: VARIANT
<222> LOCATION: (4)..(4)
<223> OTHER INFORMATION: /replace="Val" /replace="Asp"
<220> FEATURE:
<221> NAME/KEY: VARIANT
<222> LOCATION: (5)..(5)
<223> OTHER INFORMATION: /replace="Met" /replace="Ile"
<220> FEATURE:
<221> NAME/KEY: VARIANT
<222> LOCATION: (8)..(8)
<223> OTHER INFORMATION: /replace="Thr"
<220> FEATURE:
<221> NAME/KEY: VARIANT
<222> LOCATION: (9)..(9)
<223> OTHER INFORMATION: /replace="Asn" /replace="Gly"
<220> FEATURE:
<221> NAME/KEY: VARIANT
<222> LOCATION: (10)..(10)
<223> OTHER INFORMATION: /replace="Arg" /replace="Glu"
<220> FEATURE:
<221> NAME/KEY: VARIANT
<222> LOCATION: (11)..(11)
<223> OTHER INFORMATION: /replace="Thr"
<220> FEATURE:
<221> NAME/KEY: VARIANT
<222> LOCATION: (12)..(12)
<223> OTHER INFORMATION: /replace="Ala"
<220> FEATURE:
<221> NAME/KEY: VARIANT
<222> LOCATION: (13)..(13)
<223> OTHER INFORMATION: /replace="Thr" /replace="Tyr"
<220> FEATURE:
<221> NAME/KEY: MISC_FEATURE
<222> LOCATION: (2),(4)..(5),(8)..(13)
<223> OTHER INFORMATION: /note="residues given in the sequence have no preference with respect to those in the annotations for said positions"

<400> SEQUENCE: 11

Val Val Gly Ser Leu Gly Pro Gly Thr Lys Leu Pro Ser
1 5 10

<210> SEQ ID NO 12
<211> LENGTH: 20
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(20)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Tyr"
<220> FEATURE:
<221> NAME/KEY: VARIANT
<222> LOCATION: (2)..(2)
<223> OTHER INFORMATION: /replace="Asp" /replace="Glu"
<220> FEATURE:
<221> NAME/KEY: VARIANT
<222> LOCATION: (3)..(3)
<223> OTHER INFORMATION: /replace="Val" /replace="Gly"
/replace="Glu"
<220> FEATURE:
<221> NAME/KEY: VARIANT
<222> LOCATION: (4)..(4)
<223> OTHER INFORMATION: /replace="Phe"
<220> FEATURE:
<221> NAME/KEY: VARIANT
<222> LOCATION: (5)..(5)
<223> OTHER INFORMATION: /replace="Val" /replace="Tyr"
<220> FEATURE:
<221> NAME/KEY: VARIANT
<222> LOCATION: (6)..(6)
<223> OTHER INFORMATION: /replace="Asp" /replace="Ala"
/replace="Glu"
<220> FEATURE:
<221> NAME/KEY: VARIANT
<222> LOCATION: (7)..(7)
<223> OTHER INFORMATION: /replace="Ala" /replace="Asn"
<220> FEATURE:
<221> NAME/KEY: VARIANT
<222> LOCATION: (8)..(8)
<223> OTHER INFORMATION: /replace="Glu"
<220> FEATURE:
<221> NAME/KEY: VARIANT
<222> LOCATION: (9)..(9)
<223> OTHER INFORMATION: /replace="Gln" /replace="Arg"
<220> FEATURE:
<221> NAME/KEY: VARIANT
<222> LOCATION: (10)..(10)
<223> OTHER INFORMATION: /replace="Arg"
<220> FEATURE:
<221> NAME/KEY: VARIANT
<222> LOCATION: (11)..(11)
<223> OTHER INFORMATION: /replace="Asn" /replace="Ser"
/replace="Thr"
<220> FEATURE:
<221> NAME/KEY: VARIANT
<222> LOCATION: (12)..(12)
<223> OTHER INFORMATION: /replace="Thr" /replace="Val"
<220> FEATURE:
<221> NAME/KEY: VARIANT
<222> LOCATION: (13)..(13)
<223> OTHER INFORMATION: /replace="Glu" /replace="Lys"
<220> FEATURE:
<221> NAME/KEY: VARIANT
<222> LOCATION: (14)..(14)
<223> OTHER INFORMATION: /replace="Ala" /replace="Ile"
<220> FEATURE:
<221> NAME/KEY: VARIANT
<222> LOCATION: (15)..(15)
<223> OTHER INFORMATION: /replace="Leu" /replace="Met"
<220> FEATURE:
<221> NAME/KEY: VARIANT
<222> LOCATION: (16)..(16)
<223> OTHER INFORMATION: /replace="Val"
<220> FEATURE:
<221> NAME/KEY: VARIANT
<222> LOCATION: (17)..(17)
<223> OTHER INFORMATION: /replace="Ala"
<220> FEATURE:
<221> NAME/KEY: VARIANT
<222> LOCATION: (18)..(18)
<223> OTHER INFORMATION: /replace="Glu"
<220> FEATURE:
<221> NAME/KEY: VARIANT
<222> LOCATION: (20)..(20)
<223> OTHER INFORMATION: /replace="Ala" /replace="Val"
<220> FEATURE:
<221> NAME/KEY: misc_feature
<222> LOCATION: (1)..(18),(20)
<223> OTHER INFORMATION: /note="residues given in the sequence have
no preference with respect to those in the annotations for said
positions"

<400> SEQUENCE: 12

Phe Thr Asp Leu Arg Gly His Tyr Lys Glu Ala Ala Leu Gly Ile Ile
1 5 10 15

```
Glu Gly Gly Gly
            20


<210> SEQ ID NO 13
<211> LENGTH: 7
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(7)
<223> OTHER INFORMATION: /note="methionine synthase sequence motif"
<220> FEATURE:
<221> NAME/KEY: VARIANT
<222> LOCATION: (2)..(2)
<223> OTHER INFORMATION: /replace="Leu"       /replace="Gly"
<220> FEATURE:
<221> NAME/KEY: VARIANT
<222> LOCATION: (3)..(3)
<223> OTHER INFORMATION: /replace="Leu"       /replace="Ile"
<220> FEATURE:
<221> NAME/KEY: VARIANT
<222> LOCATION: (4)..(4)
<223> OTHER INFORMATION: /replace="Ile"
<220> FEATURE:
<221> NAME/KEY: VARIANT
<222> LOCATION: (5)..(5)
<223> OTHER INFORMATION: /replace="Val"       /replace="Phe"
<220> FEATURE:
<221> NAME/KEY: MISC_FEATURE
<222> LOCATION: (2)..(5)
<223> OTHER INFORMATION: /note="residues given in the sequence have
      no preference with respect to those in the annotations for said
      positions"

<400> SEQUENCE: 13

Asp Ala Phe Leu Ile Glu Thr
1               5


<210> SEQ ID NO 14
<211> LENGTH: 14
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(14)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Phe"       /replace="Ser"
<220> FEATURE:
<221> NAME/KEY: VARIANT
<222> LOCATION: (3)..(3)
<223> OTHER INFORMATION: /replace="Thr"       /replace="Ile"
<220> FEATURE:
<221> NAME/KEY: VARIANT
<222> LOCATION: (5)..(5)
<223> OTHER INFORMATION: /replace="Asn"       /replace="Glu"
<220> FEATURE:
<221> NAME/KEY: VARIANT
<222> LOCATION: (6)..(6)
<223> OTHER INFORMATION: /replace="Thr"       /replace="Ala"
      /replace="Leu"
<220> FEATURE:
<221> NAME/KEY: VARIANT
<222> LOCATION: (9)..(9)
<223> OTHER INFORMATION: /replace="Ser"
<220> FEATURE:
<221> NAME/KEY: VARIANT
<222> LOCATION: (11)..(11)
<223> OTHER INFORMATION: /replace="Leu"       /replace="Phe"
<220> FEATURE:
```

```
<221> NAME/KEY: VARIANT
<222> LOCATION: (12)..(12)
<223> OTHER INFORMATION: /replace="Ala"
<220> FEATURE:
<221> NAME/KEY: VARIANT
<222> LOCATION: (13)..(13)
<223> OTHER INFORMATION: /replace="Ala"
<220> FEATURE:
<221> NAME/KEY: VARIANT
<222> LOCATION: (14)..(14)
<223> OTHER INFORMATION: /replace="Arg"       /replace="Lys"
<220> FEATURE:
<221> NAME/KEY: MISC_FEATURE
<222> LOCATION: (1),(3),(5)..(6),(9),(11)..(14)
<223> OTHER INFORMATION: /note="residues given in the sequence have
      no preference with respect to those in the annotations for
      said positions"

<400> SEQUENCE: 14

Gln Asp Leu Leu Gln Val Lys Ala Ala Val His Gly Val Gln
1               5                   10


<210> SEQ ID NO 15
<211> LENGTH: 12
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(12)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Val"
<220> FEATURE:
<221> NAME/KEY: VARIANT
<222> LOCATION: (2)..(2)
<223> OTHER INFORMATION: /replace="Gly"       /replace="Ser"
<220> FEATURE:
<221> NAME/KEY: VARIANT
<222> LOCATION: (3)..(3)
<223> OTHER INFORMATION: /replace="Leu"       /replace="Val"
      /replace="Arg"
<220> FEATURE:
<221> NAME/KEY: VARIANT
<222> LOCATION: (4)..(4)
<223> OTHER INFORMATION: /replace="Asp"       /replace="Glu"
<220> FEATURE:
<221> NAME/KEY: VARIANT
<222> LOCATION: (5)..(5)
<223> OTHER INFORMATION: /replace="Val"
<220> FEATURE:
<221> NAME/KEY: VARIANT
<222> LOCATION: (6)..(6)
<223> OTHER INFORMATION: /replace="Phe"
<220> FEATURE:
<221> NAME/KEY: VARIANT
<222> LOCATION: (7)..(7)
<223> OTHER INFORMATION: /replace="Leu"
<220> FEATURE:
<221> NAME/KEY: VARIANT
<222> LOCATION: (8)..(8)
<223> OTHER INFORMATION: /replace="Met"
<220> FEATURE:
<221> NAME/KEY: VARIANT
<222> LOCATION: (9)..(9)
<223> OTHER INFORMATION: /replace="Val"       /replace="Ile"
      /replace="Ala"
<220> FEATURE:
<221> NAME/KEY: VARIANT
<222> LOCATION: (10)..(10)
<223> OTHER INFORMATION: /replace="Ser"
<220> FEATURE:
<221> NAME/KEY: VARIANT
<222> LOCATION: (11)..(11)
<223> OTHER INFORMATION: /replace="Gly"       /replace="Met"
```

```
<220> FEATURE:
<221> NAME/KEY: MISC_FEATURE
<222> LOCATION: (1)..(11)
<223> OTHER INFORMATION: /note="residues given in the sequence have
      no preference with respect to those in the annotations for
      said positions"

<400> SEQUENCE: 15

Leu Asp Thr Phe Leu Pro Ile Ile Cys His Val Thr
1               5                   10


<210> SEQ ID NO 16
<211> LENGTH: 13
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(13)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Ile"       /replace="Phe"
<220> FEATURE:
<221> NAME/KEY: VARIANT
<222> LOCATION: (2)..(2)
<223> OTHER INFORMATION: /replace="Thr"       /replace="Asp"
<220> FEATURE:
<221> NAME/KEY: VARIANT
<222> LOCATION: (3)..(3)
<223> OTHER INFORMATION: /replace="Asp"       /replace="Glu"
<220> FEATURE:
<221> NAME/KEY: VARIANT
<222> LOCATION: (4)..(4)
<223> OTHER INFORMATION: /replace="Ala"       /replace="Lys"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: MISC_FEATURE
<222> LOCATION: (6)..(6)
<223> OTHER INFORMATION: /note="no amino acid at this position in
      microorganisms T. maritima, C. glutamicum, Str. coelicolor"
<220> FEATURE:
<221> NAME/KEY: VARIANT
<222> LOCATION: (7)..(7)
<223> OTHER INFORMATION: /replace="Arg"
<220> FEATURE:
<221> NAME/KEY: VARIANT
<222> LOCATION: (8)..(8)
<223> OTHER INFORMATION: /replace="Thr"       /replace="Ser"
<220> FEATURE:
<221> NAME/KEY: VARIANT
<222> LOCATION: (10)..(10)
<223> OTHER INFORMATION: /replace="Leu"       /replace="Ser"
      /replace="Thr"
<220> FEATURE:
<221> NAME/KEY: VARIANT
<222> LOCATION: (12)..(12)
<223> OTHER INFORMATION: /replace="Gln"       /replace="Thr"
<220> FEATURE:
<221> NAME/KEY: VARIANT
<222> LOCATION: (13)..(13)
<223> OTHER INFORMATION: /replace="Thr"       /replace="Asp"
<220> FEATURE:
<221> NAME/KEY: MISC_FEATURE
<222> LOCATION: (1)..(8),(10),(12)..(13)
<223> OTHER INFORMATION: /note="residues given in the sequence have
      no preference with respect to those in the annotations for
      said positions"

<400> SEQUENCE: 16

Val Glu Thr Thr Gly Gly Thr Met Leu Met Gly Ser Glu
1               5                   10
```

```
<210> SEQ ID NO 17
<211> LENGTH: 7
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(7)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="Glu"       /replace="Ala"
<220> FEATURE:
<221> NAME/KEY: VARIANT
<222> LOCATION: (2)..(2)
<223> OTHER INFORMATION: /replace="Asn"
<220> FEATURE:
<221> NAME/KEY: VARIANT
<222> LOCATION: (3)..(3)
<223> OTHER INFORMATION: /replace="Phe"
<220> FEATURE:
<221> NAME/KEY: VARIANT
<222> LOCATION: (4)..(4)
<223> OTHER INFORMATION: /replace="Tyr"       /replace="Ala"
<220> FEATURE:
<221> NAME/KEY: VARIANT
<222> LOCATION: (5)..(5)
<223> OTHER INFORMATION: /replace="Asn"       /replace="Ile"
<220> FEATURE:
<221> NAME/KEY: VARIANT
<222> LOCATION: (6)..(6)
<223> OTHER INFORMATION: /replace="Ser"       /replace="Thr"
<220> FEATURE:
<221> NAME/KEY: VARIANT
<222> LOCATION: (7)..(7)
<223> OTHER INFORMATION: /replace="Phe"
<220> FEATURE:
<221> NAME/KEY: MISC_FEATURE
<222> LOCATION: (1)..(7)
<223> OTHER INFORMATION: /note="residues given in the sequence have
      no preference with respect to those in the annotations for
      said positions"

<400> SEQUENCE: 17

Gly Ala Ala Leu Thr Ala Leu
1               5


<210> SEQ ID NO 18
<211> LENGTH: 17
<212> TYPE: PRT
<213> ORGANISM: Artificial
<220> FEATURE:
<223> OTHER INFORMATION: methionine synthase sequence motif
<220> FEATURE:
<221> NAME/KEY: SOURCE
<222> LOCATION: (1)..(17)
<223> OTHER INFORMATION: /note="methionine synthase sequence motif"
<220> FEATURE:
<221> NAME/KEY: VARIANT
<222> LOCATION: (1)..(1)
<223> OTHER INFORMATION: /replace="His"       /replace="Glu"
<220> FEATURE:
<221> NAME/KEY: VARIANT
<222> LOCATION: (2)..(2)
<223> OTHER INFORMATION: /replace="Ala"
<220> FEATURE:
<221> NAME/KEY: VARIANT
<222> LOCATION: (3)..(3)
<223> OTHER INFORMATION: /replace="Glu"       /replace="Asp"
<220> FEATURE:
<221> NAME/KEY: VARIANT
<222> LOCATION: (4)..(4)
<223> OTHER INFORMATION: /replace="Ala"
<220> FEATURE:
```

```
<221> NAME/KEY: VARIANT
<222> LOCATION: (5)..(5)
<223> OTHER INFORMATION: /replace="Leu"
<220> FEATURE:
<221> NAME/KEY: VARIANT
<222> LOCATION: (6)..(6)
<223> OTHER INFORMATION: /replace="Thr"      /replace="Ala"
<220> FEATURE:
<221> NAME/KEY: VARIANT
<222> LOCATION: (7)..(7)
<223> OTHER INFORMATION: /replace="Phe"      /replace="Leu"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (12)..(12)
<223> OTHER INFORMATION: /replace="Ser"
<220> FEATURE:
<221> NAME/KEY: VARIANT
<222> LOCATION: (13)..(13)
<223> OTHER INFORMATION: /replace="Leu"
<220> FEATURE:
<221> NAME/KEY: VARIANT
<222> LOCATION: (16)..(16)
<223> OTHER INFORMATION: /replace="Ala"      /replace="Glu"
<220> FEATURE:
<221> NAME/KEY: MISC_FEATURE
<222> LOCATION: (1)..(7),(9),(12)..(13),(16)
<223> OTHER INFORMATION: /note="residues given in the sequence have
      no preference with respect to those in the annotations for
      said positions"

<400> SEQUENCE: 18

Pro Leu Gly Ile Asp Met Ile Gly Leu Asn Cys Ala Thr Gly Pro Asp
1               5                   10                  15

Glu


<210> SEQ ID NO 19
<211> LENGTH: 1221
<212> TYPE: PRT
<213> ORGANISM: Corynebacterium glutamicum
<220> FEATURE:
<221> NAME/KEY: MUTAGEN
<222> LOCATION: (33)..(33)
<223> OTHER INFORMATION: methionine synthase MetH carrying M33A mutation

<400> SEQUENCE: 19

Met Ser Thr Ser Val Thr Ser Pro Ala His Asn Asn Ala His Ser Ser
1               5                   10                  15

Glu Phe Leu Asp Ala Leu Ala Asn His Val Leu Ile Gly Asp Gly Ala
            20                  25                  30

Ala Gly Thr Gln Leu Gln Gly Phe Asp Leu Asp Val Glu Lys Asp Phe
        35                  40                  45

Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
65                  70                  75                  80

Val Glu Thr Asn Thr Phe Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140
```

```
Gly His Ala Pro Tyr Ala Asp Leu Arg Gly His Tyr Lys Glu Ala Ala
145                 150                 155                 160

Leu Gly Ile Ile Asp Gly Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
            340                 345                 350

Ala Ser Leu Tyr Thr Ser Val Pro Leu Ser Gln Glu Thr Gly Ile Ser
        355                 360                 365

Met Ile Gly Glu Arg Thr Asn Ser Asn Gly Ser Lys Ala Phe Arg Glu
    370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
            420                 425                 430

Thr Ser Ser Thr Leu Pro Ile Met Ile Asp Ser Thr Glu Pro Glu Val
        435                 440                 445

Ile Arg Thr Gly Leu Glu His Leu Gly Gly Arg Ser Ile Val Asn Ser
    450                 455                 460

Val Asn Phe Glu Asp Gly Asp Gly Pro Glu Ser Arg Tyr Gln Arg Ile
465                 470                 475                 480

Met Lys Leu Val Lys Gln His Gly Ala Ala Val Val Ala Leu Thr Ile
                485                 490                 495

Asp Glu Glu Gly Gln Ala Arg Thr Ala Glu His Lys Val Arg Ile Ala
            500                 505                 510

Lys Arg Leu Ile Asp Asp Ile Thr Gly Ser Tyr Gly Leu Asp Ile Lys
        515                 520                 525

Asp Ile Val Val Asp Cys Leu Thr Phe Pro Ile Ser Thr Gly Gln Glu
    530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575
```

```
Ser Phe Gly Leu Asn Pro Ala Ala Arg Gln Val Leu Asn Ser Val Phe
            580                 585                 590

Leu Asn Glu Cys Ile Glu Ala Gly Leu Asp Ser Ala Ile Ala His Ser
        595                 600                 605

Ser Lys Ile Leu Pro Met Asn Arg Ile Asp Asp Arg Gln Arg Glu Val
    610                 615                 620

Ala Leu Asp Met Val Tyr Asp Arg Arg Thr Glu Asp Tyr Asp Pro Leu
625                 630                 635                 640

Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Glu Ala Glu Ala Thr Gly
            740                 745                 750

Ser Ala Gln Ala Glu Gly Lys Gly Lys Ile Val Val Ala Thr Val Lys
        755                 760                 765

Gly Asp Val His Asp Ile Gly Lys Asn Leu Val Asp Ile Ile Leu Ser
    770                 775                 780

Asn Asn Gly Tyr Asp Val Val Asn Leu Gly Ile Lys Gln Pro Leu Ser
785                 790                 795                 800

Ala Met Leu Glu Ala Ala Glu Glu His Lys Ala Asp Val Ile Gly Met
                805                 810                 815

Ser Gly Leu Leu Val Lys Ser Thr Val Val Met Lys Glu Asn Leu Glu
            820                 825                 830

Glu Met Asn Asn Ala Gly Ala Ser Asn Tyr Pro Val Ile Leu Gly Gly
        835                 840                 845

Ala Ala Leu Thr Arg Thr Tyr Val Glu Asn Asp Leu Asn Glu Val Tyr
    850                 855                 860

Thr Gly Glu Val Tyr Tyr Ala Arg Asp Ala Phe Glu Gly Leu Arg Leu
865                 870                 875                 880

Met Asp Glu Val Met Ala Glu Lys Arg Gly Glu Gly Leu Asp Pro Asn
                885                 890                 895

Ser Pro Glu Ala Ile Glu Gln Ala Lys Lys Lys Ala Glu Arg Lys Ala
            900                 905                 910

Arg Asn Glu Arg Ser Arg Lys Ile Ala Ala Glu Arg Lys Ala Asn Ala
        915                 920                 925

Ala Pro Val Ile Val Pro Glu Arg Ser Asp Val Ser Thr Asp Thr Pro
    930                 935                 940

Thr Ala Ala Pro Pro Phe Trp Gly Thr Arg Ile Val Lys Gly Leu Pro
945                 950                 955                 960

Leu Ala Glu Phe Leu Gly Asn Leu Asp Glu Arg Ala Leu Phe Met Gly
                965                 970                 975

Gln Trp Gly Leu Lys Ser Thr Arg Gly Asn Glu Gly Pro Ser Tyr Glu
            980                 985                 990

Asp Leu Val Glu Thr Glu Gly Arg  Pro Arg Leu Arg Tyr  Trp Leu Asp
```

```
        995                 1000                1005

Arg Leu  Lys Ser Glu Gly Ile  Leu Asp His Val Ala  Leu Val Tyr
    1010                 1015                 1020

Gly Tyr  Phe Pro Ala Val Ala  Glu Gly Asp Asp Val  Val Ile Leu
    1025                 1030                 1035

Glu Ser  Pro Asp Pro His Ala  Ala Glu Arg Met Arg  Phe Ser Phe
    1040                 1045                 1050

Pro Arg  Gln Gln Arg Gly Arg  Phe Leu Cys Ile Ala  Asp Phe Ile
    1055                 1060                 1065

Arg Pro  Arg Glu Gln Ala Val  Lys Asp Gly Gln Val  Asp Val Met
    1070                 1075                 1080

Pro Phe  Gln Leu Val Thr Met  Gly Asn Pro Ile Ala  Asp Phe Ala
    1085                 1090                 1095

Asn Glu  Leu Phe Ala Ala Asn  Glu Tyr Arg Glu Tyr  Leu Glu Val
    1100                 1105                 1110

His Gly  Ile Gly Val Gln Leu  Thr Glu Ala Leu Ala  Glu Tyr Trp
    1115                 1120                 1125

His Ser  Arg Val Arg Ser Glu  Leu Lys Leu Asn Asp  Gly Gly Ser
    1130                 1135                 1140

Val Ala  Asp Phe Asp Pro Glu  Asp Lys Thr Lys Phe  Phe Asp Leu
    1145                 1150                 1155

Asp Tyr  Arg Gly Ala Arg Phe  Ser Phe Gly Tyr Gly  Ser Cys Pro
    1160                 1165                 1170

Asp Leu  Glu Asp Arg Ala Lys  Leu Val Glu Leu Leu  Glu Pro Gly
    1175                 1180                 1185

Arg Ile  Gly Val Glu Leu Ser  Glu Glu Leu Gln Leu  His Pro Glu
    1190                 1195                 1200

Gln Ser  Thr Asp Ala Phe Val  Leu Tyr His Pro Glu  Ala Lys Tyr
    1205                 1210                 1215

Phe Asn  Val
    1220


<210> SEQ ID NO 20
<211> LENGTH: 1221
<212> TYPE: PRT
<213> ORGANISM: Corynebacterium glutamicum
<220> FEATURE:
<221> NAME/KEY: MUTAGEN
<222> LOCATION: (33)..(33)
<223> OTHER INFORMATION: methionine synthase MetH carrying M33L
      mutation

<400> SEQUENCE: 20

Met Ser Thr Ser Val Thr Ser Pro Ala His Asn Asn Ala His Ser Ser
1               5                   10                  15

Glu Phe Leu Asp Ala Leu Ala Asn His Val Leu Ile Gly Asp Gly Ala
            20                  25                  30

Gly Gly Thr Gln Leu Gln Gly Phe Asp Leu Asp Val Glu Lys Asp Phe
        35                  40                  45

Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
65                  70                  75                  80

Val Glu Thr Asn Thr Phe Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110
```

```
Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
            340                 345                 350

Ala Ser Leu Tyr Thr Ser Val Pro Leu Ser Gln Glu Thr Gly Ile Ser
        355                 360                 365

Met Ile Gly Glu Arg Thr Asn Ser Asn Gly Ser Lys Ala Phe Arg Glu
    370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
            420                 425                 430

Thr Ser Ser Thr Leu Pro Ile Met Ile Asp Ser Thr Glu Pro Glu Val
        435                 440                 445

Ile Arg Thr Gly Leu Glu His Leu Gly Gly Arg Ser Ile Val Asn Ser
    450                 455                 460

Val Asn Phe Glu Asp Gly Asp Gly Pro Glu Ser Arg Tyr Gln Arg Ile
465                 470                 475                 480

Met Lys Leu Val Lys Gln His Gly Ala Ala Val Val Ala Leu Thr Ile
                485                 490                 495

Asp Glu Glu Gly Gln Ala Arg Thr Ala Glu His Lys Val Arg Ile Ala
            500                 505                 510

Lys Arg Leu Ile Asp Asp Ile Thr Gly Ser Tyr Gly Leu Asp Ile Lys
        515                 520                 525

Asp Ile Val Val Asp Cys Leu Thr Phe Pro Ile Ser Thr Gly Gln Glu
```

```
    530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575

Ser Phe Gly Leu Asn Pro Ala Ala Arg Gln Val Leu Asn Ser Val Phe
            580                 585                 590

Leu Asn Glu Cys Ile Glu Ala Gly Leu Asp Ser Ala Ile Ala His Ser
        595                 600                 605

Ser Lys Ile Leu Pro Met Asn Arg Ile Asp Asp Arg Gln Arg Glu Val
    610                 615                 620

Ala Leu Asp Met Val Tyr Asp Arg Arg Thr Glu Asp Tyr Asp Pro Leu
625                 630                 635                 640

Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Glu Ala Glu Ala Thr Gly
            740                 745                 750

Ser Ala Gln Ala Glu Gly Lys Gly Lys Ile Val Val Ala Thr Val Lys
        755                 760                 765

Gly Asp Val His Asp Ile Gly Lys Asn Leu Val Asp Ile Ile Leu Ser
    770                 775                 780

Asn Asn Gly Tyr Asp Val Val Asn Leu Gly Ile Lys Gln Pro Leu Ser
785                 790                 795                 800

Ala Met Leu Glu Ala Ala Glu Glu His Lys Ala Asp Val Ile Gly Met
                805                 810                 815

Ser Gly Leu Leu Val Lys Ser Thr Val Val Met Lys Glu Asn Leu Glu
            820                 825                 830

Glu Met Asn Asn Ala Gly Ala Ser Asn Tyr Pro Val Ile Leu Gly Gly
        835                 840                 845

Ala Ala Leu Thr Arg Thr Tyr Val Glu Asn Asp Leu Asn Glu Val Tyr
    850                 855                 860

Thr Gly Glu Val Tyr Tyr Ala Arg Asp Ala Phe Glu Gly Leu Arg Leu
865                 870                 875                 880

Met Asp Glu Val Met Ala Glu Lys Arg Gly Glu Gly Leu Asp Pro Asn
                885                 890                 895

Ser Pro Glu Ala Ile Glu Gln Ala Lys Lys Lys Ala Glu Arg Lys Ala
            900                 905                 910

Arg Asn Glu Arg Ser Arg Lys Ile Ala Ala Glu Arg Lys Ala Asn Ala
        915                 920                 925

Ala Pro Val Ile Val Pro Glu Arg Ser Asp Val Ser Thr Asp Thr Pro
    930                 935                 940

Thr Ala Ala Pro Pro Phe Trp Gly Thr Arg Ile Val Lys Gly Leu Pro
945                 950                 955                 960
```

```
Leu Ala Glu Phe Leu Gly Asn Leu Asp Glu Arg Ala Leu Phe Met Gly
                965                 970                 975

Gln Trp Gly Leu Lys Ser Thr Arg Gly Asn Glu Gly Pro Ser Tyr Glu
            980                 985                 990

Asp Leu Val Glu Thr Glu Gly Arg  Pro Arg Leu Arg Tyr  Trp Leu Asp
        995                 1000                1005

Arg Leu  Lys Ser Glu Gly Ile  Leu Asp His Val Ala  Leu Val Tyr
    1010                1015                1020

Gly Tyr  Phe Pro Ala Val Ala  Glu Gly Asp Asp Val  Val Ile Leu
    1025                1030                1035

Glu Ser  Pro Asp Pro His Ala  Ala Glu Arg Met Arg  Phe Ser Phe
    1040                1045                1050

Pro Arg  Gln Gln Arg Gly Arg  Phe Leu Cys Ile Ala  Asp Phe Ile
    1055                1060                1065

Arg Pro  Arg Glu Gln Ala Val  Lys Asp Gly Gln Val  Asp Val Met
    1070                1075                1080

Pro Phe  Gln Leu Val Thr Met  Gly Asn Pro Ile Ala  Asp Phe Ala
    1085                1090                1095

Asn Glu  Leu Phe Ala Ala Asn  Glu Tyr Arg Glu Tyr  Leu Glu Val
    1100                1105                1110

His Gly  Ile Gly Val Gln Leu  Thr Glu Ala Leu Ala  Glu Tyr Trp
    1115                1120                1125

His Ser  Arg Val Arg Ser Glu  Leu Lys Leu Asn Asp  Gly Gly Ser
    1130                1135                1140

Val Ala  Asp Phe Asp Pro Glu  Asp Lys Thr Lys Phe  Phe Asp Leu
    1145                1150                1155

Asp Tyr  Arg Gly Ala Arg Phe  Ser Phe Gly Tyr Gly  Ser Cys Pro
    1160                1165                1170

Asp Leu  Glu Asp Arg Ala Lys  Leu Val Glu Leu Leu  Glu Pro Gly
    1175                1180                1185

Arg Ile  Gly Val Glu Leu Ser  Glu Glu Leu Gln Leu  His Pro Glu
    1190                1195                1200

Gln Ser  Thr Asp Ala Phe Val  Leu Tyr His Pro Glu  Ala Lys Tyr
    1205                1210                1215

Phe Asn  Val
    1220


<210> SEQ ID NO 21
<211> LENGTH: 1221
<212> TYPE: PRT
<213> ORGANISM: Corynebacterium glutamicum
<220> FEATURE:
<221> NAME/KEY: MUTAGEN
<222> LOCATION: (86)..(86)
<223> OTHER INFORMATION: methionine synthase MetH carrying F86L
      mutation

<400> SEQUENCE: 21

Met Ser Thr Ser Val Thr Ser Pro Ala His Asn Asn Ala His Ser Ser
1               5                   10                  15

Glu Phe Leu Asp Ala Leu Ala Asn His Val Leu Ile Gly Asp Gly Ala
            20                  25                  30

Met Gly Thr Gln Leu Gln Gly Phe Asp Leu Asp Val Glu Lys Asp Phe
        35                  40                  45

Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
```

```
65                  70                  75                  80

Val Glu Thr Asn Thr Leu Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
            340                 345                 350

Ala Ser Leu Tyr Thr Ser Val Pro Leu Ser Gln Glu Thr Gly Ile Ser
        355                 360                 365

Met Ile Gly Glu Arg Thr Asn Ser Asn Gly Ser Lys Ala Phe Arg Glu
    370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
            420                 425                 430

Thr Ser Ser Thr Leu Pro Ile Met Ile Asp Ser Thr Glu Pro Glu Val
        435                 440                 445

Ile Arg Thr Gly Leu Glu His Leu Gly Gly Arg Ser Ile Val Asn Ser
    450                 455                 460

Val Asn Phe Glu Asp Gly Asp Gly Pro Glu Ser Arg Tyr Gln Arg Ile
465                 470                 475                 480

Met Lys Leu Val Lys Gln His Gly Ala Ala Val Val Ala Leu Thr Ile
                485                 490                 495
```

```
Asp Glu Glu Gly Gln Ala Arg Thr Ala Glu His Lys Val Arg Ile Ala
            500                 505                 510

Lys Arg Leu Ile Asp Asp Ile Thr Gly Ser Tyr Gly Leu Asp Ile Lys
        515                 520                 525

Asp Ile Val Val Asp Cys Leu Thr Phe Pro Ile Ser Thr Gly Gln Glu
    530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575

Ser Phe Gly Leu Asn Pro Ala Ala Arg Gln Val Leu Asn Ser Val Phe
            580                 585                 590

Leu Asn Glu Cys Ile Glu Ala Gly Leu Asp Ser Ala Ile Ala His Ser
        595                 600                 605

Ser Lys Ile Leu Pro Met Asn Arg Ile Asp Asp Arg Gln Arg Glu Val
    610                 615                 620

Ala Leu Asp Met Val Tyr Asp Arg Arg Thr Glu Asp Tyr Asp Pro Leu
625                 630                 635                 640

Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Glu Ala Glu Ala Thr Gly
            740                 745                 750

Ser Ala Gln Ala Glu Gly Lys Gly Lys Ile Val Val Ala Thr Val Lys
        755                 760                 765

Gly Asp Val His Asp Ile Gly Lys Asn Leu Val Asp Ile Ile Leu Ser
    770                 775                 780

Asn Asn Gly Tyr Asp Val Val Asn Leu Gly Ile Lys Gln Pro Leu Ser
785                 790                 795                 800

Ala Met Leu Glu Ala Ala Glu Glu His Lys Ala Asp Val Ile Gly Met
                805                 810                 815

Ser Gly Leu Leu Val Lys Ser Thr Val Val Met Lys Glu Asn Leu Glu
            820                 825                 830

Glu Met Asn Asn Ala Gly Ala Ser Asn Tyr Pro Val Ile Leu Gly Gly
        835                 840                 845

Ala Ala Leu Thr Arg Thr Tyr Val Glu Asn Asp Leu Asn Glu Val Tyr
    850                 855                 860

Thr Gly Glu Val Tyr Tyr Ala Arg Asp Ala Phe Glu Gly Leu Arg Leu
865                 870                 875                 880

Met Asp Glu Val Met Ala Glu Lys Arg Gly Glu Gly Leu Asp Pro Asn
                885                 890                 895

Ser Pro Glu Ala Ile Glu Gln Ala Lys Lys Lys Ala Glu Arg Lys Ala
            900                 905                 910

Arg Asn Glu Arg Ser Arg Lys Ile Ala Ala Glu Arg Lys Ala Asn Ala
        915                 920                 925
```

```
Ala Pro Val Ile Val Pro Glu Arg Ser Asp Val Ser Thr Asp Thr Pro
    930                 935                 940

Thr Ala Ala Pro Pro Phe Trp Gly Thr Arg Ile Val Lys Gly Leu Pro
945                 950                 955                 960

Leu Ala Glu Phe Leu Gly Asn Leu Asp Glu Arg Ala Leu Phe Met Gly
                965                 970                 975

Gln Trp Gly Leu Lys Ser Thr Arg Gly Asn Glu Gly Pro Ser Tyr Glu
            980                 985                 990

Asp Leu Val Glu Thr Glu Gly Arg  Pro Arg Leu Arg Tyr  Trp Leu Asp
        995                 1000                1005

Arg Leu  Lys Ser Glu Gly Ile  Leu Asp His Val Ala  Leu Val Tyr
    1010                1015                1020

Gly Tyr  Phe Pro Ala Val Ala  Glu Gly Asp Asp Val  Val Ile Leu
    1025                1030                1035

Glu Ser  Pro Asp Pro His Ala  Ala Glu Arg Met Arg  Phe Ser Phe
    1040                1045                1050

Pro Arg  Gln Gln Arg Gly Arg  Phe Leu Cys Ile Ala  Asp Phe Ile
    1055                1060                1065

Arg Pro  Arg Glu Gln Ala Val  Lys Asp Gly Gln Val  Asp Val Met
    1070                1075                1080

Pro Phe  Gln Leu Val Thr Met  Gly Asn Pro Ile Ala  Asp Phe Ala
    1085                1090                1095

Asn Glu  Leu Phe Ala Ala Asn  Glu Tyr Arg Glu Tyr  Leu Glu Val
    1100                1105                1110

His Gly  Ile Gly Val Gln Leu  Thr Glu Ala Leu Ala  Glu Tyr Trp
    1115                1120                1125

His Ser  Arg Val Arg Ser Glu  Leu Lys Leu Asn Asp  Gly Gly Ser
    1130                1135                1140

Val Ala  Asp Phe Asp Pro Glu  Asp Lys Thr Lys Phe  Phe Asp Leu
    1145                1150                1155

Asp Tyr  Arg Gly Ala Arg Phe  Ser Phe Gly Tyr Gly  Ser Cys Pro
    1160                1165                1170

Asp Leu  Glu Asp Arg Ala Lys  Leu Val Glu Leu Leu  Glu Pro Gly
    1175                1180                1185

Arg Ile  Gly Val Glu Leu Ser  Glu Glu Leu Gln Leu  His Pro Glu
    1190                1195                1200

Gln Ser  Thr Asp Ala Phe Val  Leu Tyr His Pro Glu  Ala Lys Tyr
    1205                1210                1215

Phe Asn  Val
    1220


<210> SEQ ID NO 22
<211> LENGTH: 1221
<212> TYPE: PRT
<213> ORGANISM: Corynebacterium glutamicum
<220> FEATURE:
<221> NAME/KEY: MUTAGEN
<222> LOCATION: (134)..(134)
<223> OTHER INFORMATION: methionine synthase MetH carrying S134N
      mutation

<400> SEQUENCE: 22

Met Ser Thr Ser Val Thr Ser Pro Ala His Asn Asn Ala His Ser Ser
1               5                   10                  15

Glu Phe Leu Asp Ala Leu Ala Asn His Val Leu Ile Gly Asp Gly Ala
            20                  25                  30
```

```
Met Gly Thr Gln Leu Gln Gly Phe Asp Leu Asp Val Glu Lys Asp Phe
        35                  40                  45

Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
65                  70                  75                  80

Val Glu Thr Asn Thr Phe Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Asn Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
            340                 345                 350

Ala Ser Leu Tyr Thr Ser Val Pro Leu Ser Gln Glu Thr Gly Ile Ser
        355                 360                 365

Met Ile Gly Glu Arg Thr Asn Ser Asn Gly Ser Lys Ala Phe Arg Glu
    370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
            420                 425                 430

Thr Ser Ser Thr Leu Pro Ile Met Ile Asp Ser Thr Glu Pro Glu Val
        435                 440                 445

Ile Arg Thr Gly Leu Glu His Leu Gly Gly Arg Ser Ile Val Asn Ser
    450                 455                 460
```

```
Val Asn Phe Glu Asp Gly Asp Gly Pro Glu Ser Arg Tyr Gln Arg Ile
465                 470                 475                 480

Met Lys Leu Val Lys Gln His Gly Ala Ala Val Val Ala Leu Thr Ile
                485                 490                 495

Asp Glu Glu Gly Gln Ala Arg Thr Ala Glu His Lys Val Arg Ile Ala
            500                 505                 510

Lys Arg Leu Ile Asp Asp Ile Thr Gly Ser Tyr Gly Leu Asp Ile Lys
        515                 520                 525

Asp Ile Val Val Asp Cys Leu Thr Phe Pro Ile Ser Thr Gly Gln Glu
    530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575

Ser Phe Gly Leu Asn Pro Ala Ala Arg Gln Val Leu Asn Ser Val Phe
            580                 585                 590

Leu Asn Glu Cys Ile Glu Ala Gly Leu Asp Ser Ala Ile Ala His Ser
        595                 600                 605

Ser Lys Ile Leu Pro Met Asn Arg Ile Asp Asp Arg Gln Arg Glu Val
    610                 615                 620

Ala Leu Asp Met Val Tyr Asp Arg Arg Thr Glu Asp Tyr Asp Pro Leu
625                 630                 635                 640

Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Glu Ala Glu Ala Thr Gly
            740                 745                 750

Ser Ala Gln Ala Glu Gly Lys Gly Lys Ile Val Val Ala Thr Val Lys
        755                 760                 765

Gly Asp Val His Asp Ile Gly Lys Asn Leu Val Asp Ile Ile Leu Ser
    770                 775                 780

Asn Asn Gly Tyr Asp Val Val Asn Leu Gly Ile Lys Gln Pro Leu Ser
785                 790                 795                 800

Ala Met Leu Glu Ala Ala Glu Glu His Lys Ala Asp Val Ile Gly Met
                805                 810                 815

Ser Gly Leu Leu Val Lys Ser Thr Val Val Met Lys Glu Asn Leu Glu
            820                 825                 830

Glu Met Asn Asn Ala Gly Ala Ser Asn Tyr Pro Val Ile Leu Gly Gly
        835                 840                 845

Ala Ala Leu Thr Arg Thr Tyr Val Glu Asn Asp Leu Asn Glu Val Tyr
    850                 855                 860

Thr Gly Glu Val Tyr Tyr Ala Arg Asp Ala Phe Glu Gly Leu Arg Leu
865                 870                 875                 880

Met Asp Glu Val Met Ala Glu Lys Arg Gly Glu Gly Leu Asp Pro Asn
```

```
                885                 890                 895

Ser Pro Glu Ala Ile Glu Gln Ala Lys Lys Lys Ala Glu Arg Lys Ala
            900                 905                 910

Arg Asn Glu Arg Ser Arg Lys Ile Ala Ala Glu Arg Lys Ala Asn Ala
        915                 920                 925

Ala Pro Val Ile Val Pro Glu Arg Ser Asp Val Ser Thr Asp Thr Pro
    930                 935                 940

Thr Ala Ala Pro Pro Phe Trp Gly Thr Arg Ile Val Lys Gly Leu Pro
945                 950                 955                 960

Leu Ala Glu Phe Leu Gly Asn Leu Asp Glu Arg Ala Leu Phe Met Gly
                965                 970                 975

Gln Trp Gly Leu Lys Ser Thr Arg Gly Asn Glu Gly Pro Ser Tyr Glu
            980                 985                 990

Asp Leu Val Glu Thr Glu Gly Arg  Pro Arg Leu Arg Tyr  Trp Leu Asp
        995                 1000                1005

Arg Leu  Lys Ser Glu Gly Ile  Leu Asp His Val Ala  Leu Val Tyr
    1010                 1015                 1020

Gly Tyr  Phe Pro Ala Val Ala  Glu Gly Asp Asp Val  Val Ile Leu
    1025                 1030                 1035

Glu Ser  Pro Asp Pro His Ala  Ala Glu Arg Met Arg  Phe Ser Phe
    1040                 1045                 1050

Pro Arg  Gln Gln Arg Gly Arg  Phe Leu Cys Ile Ala  Asp Phe Ile
    1055                 1060                 1065

Arg Pro  Arg Glu Gln Ala Val  Lys Asp Gly Gln Val  Asp Val Met
    1070                 1075                 1080

Pro Phe  Gln Leu Val Thr Met  Gly Asn Pro Ile Ala  Asp Phe Ala
    1085                 1090                 1095

Asn Glu  Leu Phe Ala Ala Asn  Glu Tyr Arg Glu Tyr  Leu Glu Val
    1100                 1105                 1110

His Gly  Ile Gly Val Gln Leu  Thr Glu Ala Leu Ala  Glu Tyr Trp
    1115                 1120                 1125

His Ser  Arg Val Arg Ser Glu  Leu Lys Leu Asn Asp  Gly Gly Ser
    1130                 1135                 1140

Val Ala  Asp Phe Asp Pro Glu  Asp Lys Thr Lys Phe  Phe Asp Leu
    1145                 1150                 1155

Asp Tyr  Arg Gly Ala Arg Phe  Ser Phe Gly Tyr Gly  Ser Cys Pro
    1160                 1165                 1170

Asp Leu  Glu Asp Arg Ala Lys  Leu Val Glu Leu Leu  Glu Pro Gly
    1175                 1180                 1185

Arg Ile  Gly Val Glu Leu Ser  Glu Glu Leu Gln Leu  His Pro Glu
    1190                 1195                 1200

Gln Ser  Thr Asp Ala Phe Val  Leu Tyr His Pro Glu  Ala Lys Tyr
    1205                 1210                 1215

Phe Asn  Val
    1220


<210> SEQ ID NO 23
<211> LENGTH: 3666
<212> TYPE: DNA
<213> ORGANISM: Corynebacterium glutamicum
<220> FEATURE:
<221> NAME/KEY: misc_feature
<223> OTHER INFORMATION: methionine synthase metH

<400> SEQUENCE: 23

atgtctactt cagttacttc accagcccac aacaacgcac attcctccga atttttggat     60
```

```
gcgttggcaa accatgtgtt gatcggcgac ggcgccatgg gcacccagct ccaaggcttt    120
gacctggacg tggaaaagga tttccttgat ctggaggggt gtaatgagat tctcaacgac    180
acccgccctg atgtgttgag gcagattcac cgcgcctact ttgaggcggg agctgacttg    240
gttgagacca atacttttgg ttgcaacctg ccgaacttgg cggattatga catcgctgat    300
cgttgccgtg agcttgccta caagggcact gcagtggcta gggaagtggc tgatgagatg    360
gggccgggcc gaaacggcat gcggcgtttc gtggttggtt ccctgggacc tggaacgaag    420
cttccatcgc tgggccatgc accgtatgca gatttgcgtg ggcactacaa ggaagcagcg    480
cttggcatca tcgacggtgg tggcgatgcc tttttgattg agactgctca ggacttgctt    540
caggtcaagg ctgcggttca cggcgttcaa gatgccatgg ctgaacttga tacattcttg    600
cccattattt gccacgtcac cgtagagacc accggcacca tgctcatggg ttctgagatc    660
ggtgccgcgt tgacagcgct gcagccactg ggtatcgaca tgattggtct gaactgcgcc    720
accggcccag atgagatgag cgagcacctg cgttacctgt ccaagcacgc cgatattcct    780
gtgtcggtga tgcctaacgc aggtcttcct gtcctgggta aaaacggtgc agaataccca    840
cttgaggctg aggatttggc gcaggcgctg gctggattcg tctccgaata tggcctgtcc    900
atggtgggtg gttgttgtgg caccacacct gagcacatcc gtgcggtccg cgatgcggtg    960
gttggtgttc cagagcagga aacctccaca ctgaccaaga tccctgcagg ccctgttgag   1020
caggcctccc gcgaggtgga gaaagaggac tccgtcgcgt cgctgtacac ctcggtgcca   1080
ttgtcccagg aaaccggcat ttccatgatc ggtgagcgca ccaactccaa cggttccaag   1140
gcattccgtg aggcaatgct gtctggcgat tgggaaaagt gtgtggatat tgccaagcag   1200
caaacccgcg atggtgcaca catgctggat ctttgtgtgg attacgtggg acgagacggc   1260
accgccgata tggcgacctt ggcagcactt cttgctacca gctccacttt gccaatcatg   1320
attgactcca ccgagccaga ggttattcgc acaggccttg agcacttggg tggacgaagc   1380
atcgttaact ccgtcaactt tgaagacggc gatggccctg agtcccgcta ccagcgcatc   1440
atgaaactgg taaagcagca cggtgcggcc gtggttgcgc tgaccattga tgaggaaggc   1500
caggcacgta ccgctgagca caaggtgcgc attgctaaac gactgattga cgatatcacc   1560
ggcagctacg gcctggatat caaagacatc gttgtggact gcctgacctt cccgatctct   1620
actggccagg aagaaaccag gcgagatggc attgaaacca tcgaagccat ccgcgagctg   1680
aagaagctct acccagaaat ccacaccacc ctgggtctgt ccaatatttc cttcggcctg   1740
aaccctgctg cacgccaggt tcttaactct gtgttcctca atgagtgcat tgaggctggt   1800
ctggactctg cgattgcgca cagctccaag attttgccga tgaaccgcat tgatgatcgc   1860
cagcgcgaag tggcgttgga tatggtctat gatcgccgca ccgaggatta cgatccgctg   1920
caggaattca tgcagctgtt tgagggcgtt tctgctgccg atgccaagga tgctcgcgct   1980
gaacagctgg ccgctatgcc tttgtttgag cgtttggcac agcgcatcat cgacggcgat   2040
aagaatggcc ttgaggatga tctggaagca ggcatgaagg agaagtctcc tattgcgatc   2100
atcaacgagg accttctcaa cggcatgaag accgtgggtg agctgtttgg ttccggacag   2160
atgcagctgc cattcgtgct gcaatcggca gaaaccatga aaactgcggt ggcctatttg   2220
gaaccgttca tggaagagga agcagaagct accggatctg cgcaggcaga gggcaagggc   2280
aaaatcgtcg tggccaccgt caagggtgac gtgcacgata tcggcaagaa cttggtggac   2340
atcattttgt ccaacaacgg ttacgacgtg gtgaacttgg gcatcaagca gccactgtcc   2400
gccatgttgg aagcagcgga agaacacaaa gcagacgtca tcggcatgtc gggacttctt   2460
```

```
gtgaagtcca ccgtggtgat gaaggaaaac cttgaggaga tgaacaacgc cggcgcatcc   2520

aattacccag tcattttggg tggcgctgcg ctgacgcgta cctacgtgga aaacgatctc   2580

aacgaggtgt acaccggtga ggtgtactac gcccgtgatg ctttcgaggg cctgcgcctg   2640

atggatgagg tgatggcaga aaagcgtggt gaaggacttg atcccaactc accagaagct   2700

attgagcagg cgaagaagaa ggcggaacgt aaggctcgta atgagcgttc ccgcaagatt   2760

gccgcggagc gtaaagctaa tgcggctccc gtgattgttc cggagcgttc tgatgtctcc   2820

accgatactc caaccgcggc accaccgttc tggggaaccc gcattgtcaa gggtctgccc   2880

ttggcggagt tcttgggcaa ccttgatgag cgcgccttgt tcatggggca gtggggtctg   2940

aaatccaccc gcggcaacga gggtccaagc tatgaggatt tggtggaaac tgaaggccga   3000

ccacgcctgc gctactggct ggatcgcctg aagtctgagg gcattttgga ccacgtggcc   3060

ttggtgtatg gctacttccc agcggtcgcg gaaggcgatg acgtggtgat cttggaatcc   3120

ccggatccac acgcagccga acgcatgcgc tttagcttcc cacgccagca gcgcggcagg   3180

ttcttgtgca tcgcggattt cattcgccca cgcgagcaag ctgtcaagga cggccaagtg   3240

gacgtcatgc cattccagct ggtcaccatg ggtaatccta ttgctgattt cgccaacgag   3300

ttgttcgcag ccaatgaata ccgcgagtac ttggaagttc acggcatcgg cgtgcagctc   3360

accgaagcat tggccgagta ctggcactcc cgagtgcgca gcgaactcaa gctgaacgac   3420

ggtggatctg tcgctgattt tgatccagaa gacaagacca agttcttcga cctggattac   3480

cgcggcgccc gcttctcctt tggttacggt tcttgccctg atctggaaga ccgcgcaaag   3540

ctggtggaat tgctcgagcc aggccgtatc ggcgtggagt tgtccgagga actccagctg   3600

cacccagagc agtccacaga cgcgtttgtg ctctaccacc cagaggcaaa gtactttaac   3660

gtctaa                                                              3666
```

<210> SEQ ID NO 24
<211> LENGTH: 735
<212> TYPE: DNA
<213> ORGANISM: Corynebacterium glutamicum
<220> FEATURE:
<221> NAME/KEY: misc_feature
<223> OTHER INFORMATION: homocysteine binding domain of methionine synthase metH

<400> SEQUENCE: 24

```
atgtctactt cagttacttc accagcccac aacaacgcac attcctccga atttttggat     60

gcgttggcaa accatgtgtt gatcggcgac ggcgccatgg gcacccagct ccaaggcttt    120

gacctggacg tggaaaagga tttccttgat ctggaggggt gtaatgagat tctcaacgac    180

acccgccctg atgtgttgag gcagattcac cgcgcctact ttgaggcggg agctgacttg    240

gttgagacca atacttttgg ttgcaacctg ccgaacttgg cggattatga catcgctgat    300

cgttgccgtg agcttgccta caagggcact gcagtggcta gggaagtggc tgatgagatg    360

gggccgggcc gaaacggcat gcggcgtttc gtggttggtt ccctgggacc tggaacgaag    420

cttccatcgc tgggccatgc accgtatgca gatttgcgtg ggcactacaa ggaagcagcg    480

cttggcatca tcgacggtgg tggcgatgcc tttttgattg agactgctca ggacttgctt    540

caggtcaagg ctgcggttca cggcgttcaa gatgccatgg ctgaacttga tacattcttg    600

cccattattt gccacgtcac cgtagagacc accggcacca tgctcatggg ttctgagatc    660

ggtgccgcgt tgacagcgct gcagccactg ggtatcgaca tgattggtct gaactgcgcc    720

accggcccag atgag                                                     735
```

<210> SEQ ID NO 25
<211> LENGTH: 3666
<212> TYPE: DNA
<213> ORGANISM: Corynebacterium glutamicum
<220> FEATURE:
<221> NAME/KEY: misc_feature
<223> OTHER INFORMATION: coding sequence of methionine synthase MetH
      carrying mutation M33A

<400> SEQUENCE: 25

```
atgtctactt cagttacttc accagcccac aacaacgcac attcctccga atttttggat      60
gcgttggcaa accatgtgtt gatcggcgac ggcgccatgg gcacccagct ccaaggcttt     120
gacctggacg tggaaaagga tttccttgat ctggaggggt gtaatgagat tctcaacgac     180
acccgccctg atgtgttgag gcagattcac cgcgcctact ttgaggcggg agctgacttg     240
gttgagacca atacttttgg ttgcaacctg ccgaacttgg cggattatga catcgctgat     300
cgttgccgtg agcttgccta caagggcact gcagtggcta gggaagtggc tgatgagatg     360
gggccgggcc gaaacggcat gcggcgtttc gtggttggtt ccctgggacc tggaacgaag     420
cttccatcgc tgggccatgc accgtatgca gatttgcgtg ggcactacaa ggaagcagcg     480
cttggcatca tcgacggtgg tggcgatgcc tttttgattg agactgctca ggacttgctt     540
caggtcaagg ctgcggttca cggcgttcaa gatgccatgg ctgaacttga tacattcttg     600
cccattattt gccacgtcac cgtagagacc accggcacca tgctcatggg ttctgagatc     660
ggtgccgcgt tgacagcgct gcagccactg ggtatcgaca tgattggtct gaactgcgcc     720
accggcccag atgagatgag cgagcacctg cgttacctgt ccaagcacgc cgatattcct     780
gtgtcggtga tgcctaacgc aggtcttcct gtcctgggta aaaacggtgc agaataccca     840
cttgaggctg aggatttggc gcaggcgctg gctggattcg tctccgaata tggcctgtcc     900
atggtgggtg gttgttgtgg caccacacct gagcacatcc gtgcggtccg cgatgcggtg     960
gttggtgttc cagagcagga aacctccaca ctgaccaaga tccctgcagg ccctgttgag    1020
caggcctccc gcgaggtgga gaaagaggac tccgtcgcgt cgctgtacac ctcggtgcca    1080
ttgtcccagg aaaccggcat ttccatgatc ggtgagcgca ccaactccaa cggttccaag    1140
gcattccgtg aggcaatgct gtctggcgat tgggaaaagt gtgtggatat tgccaagcag    1200
caaacccgcg atggtgcaca catgctggat ctttgtgtgg attacgtggg acgagacggc    1260
accgccgata tggcgacctt ggcagcactt cttgctacca gctccacttt gccaatcatg    1320
attgactcca ccgagccaga ggttattcgc acaggccttg agcacttggg tggacgaagc    1380
atcgttaact ccgtcaactt tgaagacggc gatggccctg agtcccgcta ccagcgcatc    1440
atgaaactgg taaagcagca cggtgcggcc gtggttgcgc tgaccattga tgaggaaggc    1500
caggcacgta ccgctgagca caaggtgcgc attgctaaac gactgattga cgatatcacc    1560
ggcagctacg gcctggatat caaagacatc gttgtggact gcctgacctt cccgatctct    1620
actggccagg aagaaaccag gcgagatggc attgaaacca tcgaagccat ccgcgagctg    1680
aagaagctct acccagaaat ccacaccacc ctgggtctgt ccaatatttc cttcggcctg    1740
aaccctgctg cacgccaggt tcttaactct gtgttcctca atgagtgcat tgaggctggt    1800
ctggactctg cgattgcgca cagctccaag attttgccga tgaaccgcat tgatgatcgc    1860
cagcgcgaag tggcgttgga tatggtctat gatcgccgca ccgaggatta cgatccgctg    1920
caggaattca tgcagctgtt tgagggcgtt tctgctgccg atgccaagga tgctcgcgct    1980
gaacagctgg ccgctatgcc tttgtttgag cgtttggcac agcgcatcat cgacggcgat    2040
```

```
aagaatggcc ttgaggatga tctggaagca ggcatgaagg agaagtctcc tattgcgatc   2100

atcaacgagg accttctcaa cggcatgaag accgtgggtg agctgtttgg ttccggacag   2160

atgcagctgc cattcgtgct gcaatcggca gaaaccatga aaactgcggt ggcctatttg   2220

gaaccgttca tggaagagga agcagaagct accggatctg cgcaggcaga gggcaagggc   2280

aaaatcgtcg tggccaccgt caagggtgac gtgcacgata tcggcaagaa cttggtggac   2340

atcattttgt ccaacaacgg ttacgacgtg gtgaacttgg gcatcaagca gccactgtcc   2400

gccatgttgg aagcagcgga agaacacaaa gcagacgtca tcggcatgtc gggacttctt   2460

gtgaagtcca ccgtggtgat gaaggaaaac cttgaggaga tgaacaacgc cggcgcatcc   2520

aattacccag tcattttggg tggcgctgcg ctgacgcgta cctacgtgga aaacgatctc   2580

aacgaggtgt acaccggtga ggtgtactac gcccgtgatg ctttcgaggg cctgcgcctg   2640

atggatgagg tgatggcaga aaagcgtggt gaaggacttg atcccaactc accagaagct   2700

attgagcagg cgaagaagaa ggcggaacgt aaggctcgta atgagcgttc ccgcaagatt   2760

gccgcggagc gtaaagctaa tgcggctccc gtgattgttc cggagcgttc tgatgtctcc   2820

accgatactc caaccgcggc accaccgttc tggggaaccc gcattgtcaa gggtctgccc   2880

ttggcggagt tcttgggcaa ccttgatgag cgcgccttgt tcatggggca gtggggtctg   2940

aaatccaccc gcggcaacga gggtccaagc tatgaggatt tggtggaaac tgaaggccga   3000

ccacgcctgc gctactggct ggatcgcctg aagtctgagg gcattttgga ccacgtggcc   3060

ttggtgtatg gctacttccc agcggtcgcg gaaggcgatg acgtggtgat cttggaatcc   3120

ccggatccac acgcagccga acgcatgcgc tttagcttcc cacgccagca gcgcggcagg   3180

ttcttgtgca tcgcggattt cattcgccca cgcgagcaag ctgtcaagga cggccaagtg   3240

gacgtcatgc cattccagct ggtcaccatg ggtaatccta ttgctgattt cgccaacgag   3300

ttgttcgcag ccaatgaata ccgcgagtac ttggaagttc acggcatcgg cgtgcagctc   3360

accgaagcat tggccgagta ctggcactcc cgagtgcgca gcgaactcaa gctgaacgac   3420

ggtggatctg tcgctgattt tgatccagaa gacaagacca agttcttcga cctggattac   3480

cgcggcgccc gcttctcctt tggttacggt tcttgccctg atctggaaga ccgcgcaaag   3540

ctggtggaat tgctcgagcc aggccgtatc ggcgtggagt tgtccgagga actccagctg   3600

cacccagagc agtccacaga cgcgtttgtg ctctaccacc cagaggcaaa gtactttaac   3660

gtctaa                                                              3666
```

<210> SEQ ID NO 26
<211> LENGTH: 3666
<212> TYPE: DNA
<213> ORGANISM: Corynebacterium glutamicum
<220> FEATURE:
<221> NAME/KEY: misc_feature
<223> OTHER INFORMATION: coding sequence of methionine synthase MetH carrying mutation M33L

<400> SEQUENCE: 26

```
atgtctactt cagttacttc accagcccac aacaacgcac attcctccga atttttggat     60

gcgttggcaa accatgtgtt gatcggcgac ggcgccatgg gcacccagct ccaaggcttt    120

gacctggacg tggaaaagga tttccttgat ctggaggggt gtaatgagat tctcaacgac    180

acccgccctg atgtgttgag gcagattcac cgcgcctact ttgaggcggg agctgacttg    240

gttgagacca atacttttgg ttgcaacctg ccgaacttgg cggattatga catcgctgat    300

cgttgccgtg agcttgccta caagggcact gcagtggcta gggaagtggc tgatgagatg    360
```

```
gggccgggcc gaaacggcat gcggcgtttc gtggttggtt ccctgggacc tggaacgaag    420
cttccatcgc tgggccatgc accgtatgca gatttgcgtg ggcactacaa ggaagcagcg    480
cttggcatca tcgacggtgg tggcgatgcc tttttgattg agactgctca ggacttgctt    540
caggtcaagg ctgcggttca cggcgttcaa gatgccatgg ctgaacttga tacattcttg    600
cccattattt gccacgtcac cgtagagacc accggcacca tgctcatggg ttctgagatc    660
ggtgccgcgt tgacagcgct gcagccactg ggtatcgaca tgattggtct gaactgcgcc    720
accggcccag atgagatgag cgagcacctg cgttacctgt ccaagcacgc cgatattcct    780
gtgtcggtga tgcctaacgc aggtcttcct gtcctgggta aaaacggtgc agaataccca    840
cttgaggctg aggatttggc gcaggcgctg gctggattcg tctccgaata tggcctgtcc    900
atggtgggtg gttgttgtgg caccacacct gagcacatcc gtgcggtccg cgatgcggtg    960
gttggtgttc cagagcagga aacctccaca ctgaccaaga tccctgcagg ccctgttgag   1020
caggcctccc gcgaggtgga gaaagaggac tccgtcgcgt cgctgtacac ctcggtgcca   1080
ttgtcccagg aaaccggcat ttccatgatc ggtgagcgca ccaactccaa cggttccaag   1140
gcattccgtg aggcaatgct gtctggcgat tgggaaaagt gtgtggatat tgccaagcag   1200
caaacccgcg atggtgcaca catgctggat ctttgtgtgg attacgtggg acgagacggc   1260
accgccgata tggcgacctt ggcagcactt cttgctacca gctccacttt gccaatcatg   1320
attgactcca ccgagccaga ggttattcgc acaggccttg agcacttggg tggacgaagc   1380
atcgttaact ccgtcaactt tgaagacggc gatggccctg agtcccgcta ccagcgcatc   1440
atgaaactgg taaagcagca cggtgcggcc gtggttgcgc tgaccattga tgaggaaggc   1500
caggcacgta ccgctgagca caaggtgcgc attgctaaac gactgattga cgatatcacc   1560
ggcagctacg gcctggatat caaagacatc gttgtggact gcctgacctt cccgatctct   1620
actggccagg aagaaaccag gcgagatggc attgaaacca tcgaagccat ccgcgagctg   1680
aagaagctct acccagaaat ccacaccacc ctgggtctgt ccaatatttc cttcggcctg   1740
aaccctgctg cacgccaggt tcttaactct gtgttcctca atgagtgcat tgaggctggt   1800
ctggactctg cgattgcgca cagctccaag attttgccga tgaaccgcat tgatgatcgc   1860
cagcgcgaag tggcgttgga tatggtctat gatcgccgca ccgaggatta cgatccgctg   1920
caggaattca tgcagctgtt tgagggcgtt tctgctgccg atgccaagga tgctcgcgct   1980
gaacagctgg ccgctatgcc tttgtttgag cgtttggcac agcgcatcat cgacggcgat   2040
aagaatggcc ttgaggatga tctggaagca ggcatgaagg agaagtctcc tattgcgatc   2100
atcaacgagg accttctcaa cggcatgaag accgtgggtg agctgtttgg ttccggacag   2160
atgcagctgc cattcgtgct gcaatcggca gaaaccatga aaactgcggt ggcctatttg   2220
gaaccgttca tggaagagga agcagaagct accggatctg cgcaggcaga gggcaagggc   2280
aaaatcgtcg tggccaccgt caagggtgac gtgcacgata tcggcaagaa cttggtggac   2340
atcattttgt ccaacaacgg ttacgacgtg gtgaacttgg gcatcaagca gccactgtcc   2400
gccatgttgg aagcagcgga agaacacaaa gcagacgtca tcggcatgtc gggacttctt   2460
gtgaagtcca ccgtggtgat gaaggaaaac cttgaggaga tgaacaacgc cggcgcatcc   2520
aattacccag tcattttggg tggcgctgcg ctgacgcgta cctacgtgga aaacgatctc   2580
aacgaggtgt acaccggtga ggtgtactac gcccgtgatg ctttcgaggg cctgcgcctg   2640
atggatgagg tgatggcaga aaagcgtggt gaaggacttg atcccaactc accagaagct   2700
attgagcagg cgaagaagaa ggcggaacgt aaggctcgta atgagcgttc ccgcaagatt   2760
```

```
gccgcggagc gtaaagctaa tgcggctccc gtgattgttc cggagcgttc tgatgtctcc   2820

accgatactc caaccgcggc accaccgttc tggggaaccc gcattgtcaa gggtctgccc   2880

ttggcggagt tcttgggcaa ccttgatgag cgcgccttgt tcatggggca gtggggtctg   2940

aaatccaccc gcggcaacga gggtccaagc tatgaggatt tggtggaaac tgaaggccga   3000

ccacgcctgc gctactggct ggatcgcctg aagtctgagg gcattttgga ccacgtggcc   3060

ttggtgtatg gctacttccc agcggtcgcg gaaggcgatg acgtggtgat cttggaatcc   3120

ccggatccac acgcagccga acgcatgcgc tttagcttcc cacgccagca gcgcggcagg   3180

ttcttgtgca tcgcggattt cattcgccca cgcgagcaag ctgtcaagga cggccaagtg   3240

gacgtcatgc cattccagct ggtcaccatg ggtaatccta ttgctgattt cgccaacgag   3300

ttgttcgcag ccaatgaata ccgcgagtac ttggaagttc acggcatcgg cgtgcagctc   3360

accgaagcat tggccgagta ctggcactcc cgagtgcgca gcgaactcaa gctgaacgac   3420

ggtggatctg tcgctgattt tgatccagaa gacaagacca agttcttcga cctggattac   3480

cgcggcgccc gcttctcctt tggttacggt tcttgccctg atctggaaga ccgcgcaaag   3540

ctggtggaat tgctcgagcc aggccgtatc ggcgtggagt tgtccgagga actccagctg   3600

cacccagagc agtccacaga cgcgtttgtg ctctaccacc cagaggcaaa gtactttaac   3660

gtctaa                                                              3666
```

```
<210> SEQ ID NO 27
<211> LENGTH: 3666
<212> TYPE: DNA
<213> ORGANISM: Corynebacterium glutamicum
<220> FEATURE:
<221> NAME/KEY: misc_feature
<223> OTHER INFORMATION: coding sequence of methionine synthase MetH
      carrying mutation F86L

<400> SEQUENCE: 27

atgtctactt cagttacttc accagcccac aacaacgcac attcctccga atttttggat     60

gcgttggcaa accatgtgtt gatcggcgac ggcgccatgg gcacccagct ccaaggcttt    120

gacctggacg tggaaaagga tttccttgat ctggaggggt gtaatgagat tctcaacgac    180

acccgccctg atgtgttgag gcagattcac cgcgcctact ttgaggcggg agctgacttg    240

gttgagacca atacttttgg ttgcaacctg ccgaacttgg cggattatga catcgctgat    300

cgttgccgtg agcttgccta caagggcact gcagtggcta gggaagtggc tgatgagatg    360

gggccgggcc gaaacggcat gcggcgtttc gtggttggtt ccctgggacc tggaacgaag    420

cttccatcgc tgggccatgc accgtatgca gatttgcgtg ggcactacaa ggaagcagcg    480

cttggcatca tcgacggtgg tggcgatgcc tttttgattg agactgctca ggacttgctt    540

caggtcaagg ctgcggttca cggcgttcaa gatgccatgg ctgaacttga tacattcttg    600

cccattattt gccacgtcac cgtagagacc accggcacca tgctcatggg ttctgagatc    660

ggtgccgcgt tgacagcgct gcagccactg ggtatcgaca tgattggtct gaactgcgcc    720

accggcccag atgagatgag cgagcacctg cgttacctgt ccaagcacgc cgatattcct    780

gtgtcggtga tgcctaacgc aggtcttcct gtcctgggta aaaacggtgc agaataccca    840

cttgaggctg aggatttggc gcaggcgctg gctggattcg tctccgaata tggcctgtcc    900

atggtgggtg gttgttgtgg caccacacct gagcacatcc gtgcggtccg cgatgcggtg    960

gttggtgttc cagagcagga aacctccaca ctgaccaaga tccctgcagg ccctgttgag   1020

caggcctccc gcgaggtgga gaaagaggac tccgtcgcgt cgctgtacac ctcggtgcca   1080
```

```
ttgtcccagg aaaccggcat ttccatgatc ggtgagcgca ccaactccaa cggttccaag   1140
gcattccgtg aggcaatgct gtctggcgat tgggaaaagt gtgtggatat tgccaagcag   1200
caaacccgcg atggtgcaca catgctggat ctttgtgtgg attacgtggg acgagacggc   1260
accgccgata tggcgacctt ggcagcactt cttgctacca gctccacttt gccaatcatg   1320
attgactcca ccgagccaga ggttattcgc acaggccttg agcacttggg tggacgaagc   1380
atcgttaact ccgtcaactt tgaagacggc gatggccctg agtcccgcta ccagcgcatc   1440
atgaaactgg taaagcagca cggtgcggcc gtggttgcgc tgaccattga tgaggaaggc   1500
caggcacgta ccgctgagca caaggtgcgc attgctaaac gactgattga cgatatcacc   1560
ggcagctacg gcctggatat caaagacatc gttgtggact gcctgacctt cccgatctct   1620
actggccagg aagaaaccag gcgagatggc attgaaacca tcgaagccat ccgcgagctg   1680
aagaagctct acccagaaat ccacaccacc ctgggtctgt ccaatatttc cttcggcctg   1740
aaccctgctg cacgccaggt tcttaactct gtgttcctca atgagtgcat tgaggctggt   1800
ctggactctg cgattgcgca cagctccaag attttgccga tgaaccgcat tgatgatcgc   1860
cagcgcgaag tggcgttgga tatggtctat gatcgccgca ccgaggatta cgatccgctg   1920
caggaattca tgcagctgtt tgagggcgtt tctgctgccg atgccaagga tgctcgcgct   1980
gaacagctgg ccgctatgcc tttgtttgag cgtttggcac agcgcatcat cgacggcgat   2040
aagaatggcc ttgaggatga tctggaagca ggcatgaagg agaagtctcc tattgcgatc   2100
atcaacgagg accttctcaa cggcatgaag accgtgggtg agctgtttgg ttccggacag   2160
atgcagctgc cattcgtgct gcaatcggca gaaaccatga aactgcggt ggcctatttg   2220
gaaccgttca tggaagagga agcagaagct accggatctg cgcaggcaga gggcaagggc   2280
aaaatcgtcg tggccaccgt caagggtgac gtgcacgata tcggcaagaa cttggtggac   2340
atcattttgt ccaacaacgg ttacgacgtg gtgaacttgg gcatcaagca gccactgtcc   2400
gccatgttgg aagcagcgga agaacacaaa gcagacgtca tcggcatgtc gggacttctt   2460
gtgaagtcca ccgtggtgat gaaggaaaac cttgaggaga tgaacaacgc cggcgcatcc   2520
aattacccag tcattttggg tggcgctgcg ctgacgcgta cctacgtgga aaacgatctc   2580
aacgaggtgt acaccggtga ggtgtactac gcccgtgatg ctttcgaggg cctgcgcctg   2640
atggatgagg tgatggcaga aaagcgtggt gaaggacttg atcccaactc accagaagct   2700
attgagcagg cgaagaagaa ggcggaacgt aaggctcgta atgagcgttc ccgcaagatt   2760
gccgcggagc gtaaagctaa tgcggctccc gtgattgttc cggagcgttc tgatgtctcc   2820
accgatactc caaccgcggc accaccgttc tggggaaccc gcattgtcaa gggtctgccc   2880
ttggcggagt tcttgggcaa ccttgatgag cgcgccttgt tcatggggca gtggggtctg   2940
aaatccaccc gcggcaacga gggtccaagc tatgaggatt tggtggaaac tgaaggccga   3000
ccacgcctgc gctactggct ggatcgcctg aagtctgagg gcattttgga ccacgtggcc   3060
ttggtgtatg gctacttccc agcggtcgcg gaaggcgatg acgtggtgat cttggaatcc   3120
ccggatccac acgcagccga acgcatgcgc tttagcttcc cacgccagca gcgcggcagg   3180
ttcttgtgca tcgcggattt cattcgccca cgcgagcaag ctgtcaagga cggccaagtg   3240
gacgtcatgc cattccagct ggtcaccatg ggtaatccta ttgctgattt cgccaacgag   3300
ttgttcgcag ccaatgaata ccgcgagtac ttggaagttc acggcatcgg cgtgcagctc   3360
accgaagcat tggccgagta ctggcactcc cgagtgcgca gcgaactcaa gctgaacgac   3420
ggtggatctg tcgctgattt tgatccagaa gacaagacca agttcttcga cctggattac   3480
```

```
cgcggcgccc gcttctcctt tggttacggt tcttgccctg atctggaaga ccgcgcaaag   3540

ctggtggaat tgctcgagcc aggccgtatc ggcgtggagt tgtccgagga actccagctg   3600

cacccagagc agtccacaga cgcgtttgtg ctctaccacc cagaggcaaa gtactttaac   3660

gtctaa                                                              3666
```

<210> SEQ ID NO 28
<211> LENGTH: 3666
<212> TYPE: DNA
<213> ORGANISM: Corynebacterium glutamicum
<220> FEATURE:
<221> NAME/KEY: misc_feature
<223> OTHER INFORMATION: coding sequence of methionine synthase MetH carrying mutation S134N

<400> SEQUENCE: 28

```
atgtctactt cagttacttc accagcccac aacaacgcac attcctccga atttttggat     60

gcgttggcaa accatgtgtt gatcggcgac ggcgccatgg gcacccagct ccaaggcttt    120

gacctggacg tggaaaagga tttccttgat ctggaggggt gtaatgagat tctcaacgac    180

acccgccctg atgtgttgag gcagattcac cgcgcctact ttgaggcggg agctgacttg    240

gttgagacca atacttttgg ttgcaacctg ccgaacttgg cggattatga catcgctgat    300

cgttgccgtg agcttgccta caagggcact gcagtggcta gggaagtggc tgatgagatg    360

gggccgggcc gaaacggcat gcggcgtttc gtggttggtt ccctgggacc tggaacgaag    420

cttccatcgc tgggccatgc accgtatgca gatttgcgtg ggcactacaa ggaagcagcg    480

cttggcatca tcgacggtgg tggcgatgcc tttttgattg agactgctca ggacttgctt    540

caggtcaagg ctgcggttca cggcgttcaa gatgccatgg ctgaacttga tacattcttg    600

cccattattt gccacgtcac cgtagagacc accggcacca tgctcatggg ttctgagatc    660

ggtgccgcgt tgacagcgct gcagccactg ggtatcgaca tgattggtct gaactgcgcc    720

accggcccag atgagatgag cgagcacctg cgttacctgt ccaagcacgc cgatattcct    780

gtgtcggtga tgcctaacgc aggtcttcct gtcctgggta aaaacggtgc agaataccca    840

cttgaggctg aggatttggc gcaggcgctg gctggattcg tctccgaata tggcctgtcc    900

atggtgggtg gttgttgtgg caccacacct gagcacatcc gtgcggtccg cgatgcggtg    960

gttggtgttc cagagcagga aacctccaca ctgaccaaga tccctgcagg ccctgttgag   1020

caggcctccc gcgaggtgga gaaagaggac tccgtcgcgt cgctgtacac ctcggtgcca   1080

ttgtcccagg aaaccggcat ttccatgatc ggtgagcgca ccaactccaa cggttccaag   1140

gcattccgtg aggcaatgct gtctggcgat tgggaaaagt gtgtggatat tgccaagcag   1200

caaacccgcg atggtgcaca catgctggat ctttgtgtgg attacgtggg acgagacggc   1260

accgccgata tggcgacctt ggcagcactt cttgctacca gctccacttt gccaatcatg   1320

attgactcca ccgagccaga ggttattcgc acaggccttg agcacttggg tggacgaagc   1380

atcgttaact ccgtcaactt tgaagacggc gatggccctg agtcccgcta ccagcgcatc   1440

atgaaactgg taaagcagca cggtgcggcc gtggttgcgc tgaccattga tgaggaaggc   1500

caggcacgta ccgctgagca caaggtgcgc attgctaaac gactgattga cgatatcacc   1560

ggcagctacg gcctggatat caaagacatc gttgtggact gcctgacctt cccgatctct   1620

actggccagg aagaaaccag gcgagatggc attgaaacca tcgaagccat ccgcgagctg   1680

aagaagctct acccagaaat ccacaccacc ctgggtctgt ccaatatttc cttcggcctg   1740

aaccctgctg cacgccaggt tcttaactct gtgttcctca atgagtgcat tgaggctggt   1800
```

```
ctggactctg cgattgcgca cagctccaag attttgccga tgaaccgcat tgatgatcgc   1860

cagcgcgaag tggcgttgga tatggtctat gatcgccgca ccgaggatta cgatccgctg   1920

caggaattca tgcagctgtt tgagggcgtt tctgctgccg atgccaagga tgctcgcgct   1980

gaacagctgg ccgctatgcc tttgtttgag cgtttggcac agcgcatcat cgacggcgat   2040

aagaatggcc ttgaggatga tctggaagca ggcatgaagg agaagtctcc tattgcgatc   2100

atcaacgagg accttctcaa cggcatgaag accgtgggtg agctgtttgg ttccggacag   2160

atgcagctgc cattcgtgct gcaatcggca gaaaccatga aaactgcggt ggcctatttg   2220

gaaccgttca tggaagagga agcagaagct accggatctg cgcaggcaga gggcaagggc   2280

aaaatcgtcg tggccaccgt caagggtgac gtgcacgata tcggcaagaa cttggtggac   2340

atcattttgt ccaacaacgg ttacgacgtg gtgaacttgg gcatcaagca gccactgtcc   2400

gccatgttgg aagcagcgga agaacacaaa gcagacgtca tcggcatgtc gggacttctt   2460

gtgaagtcca ccgtggtgat gaaggaaaac cttgaggaga tgaacaacgc cggcgcatcc   2520

aattacccag tcattttggg tggcgctgcg ctgacgcgta cctacgtgga aaacgatctc   2580

aacgaggtgt acaccggtga ggtgtactac gcccgtgatg ctttcgaggg cctgcgcctg   2640

atggatgagg tgatggcaga aaagcgtggt gaaggacttg atcccaactc accagaagct   2700

attgagcagg cgaagaagaa ggcggaacgt aaggctcgta atgagcgttc ccgcaagatt   2760

gccgcggagc gtaaagctaa tgcggctccc gtgattgttc cggagcgttc tgatgtctcc   2820

accgatactc caaccgcggc accaccgttc tggggaaccc gcattgtcaa gggtctgccc   2880

ttggcggagt tcttgggcaa ccttgatgag cgcgccttgt tcatggggca gtggggtctg   2940

aaatccaccc gcggcaacga gggtccaagc tatgaggatt tggtggaaac tgaaggccga   3000

ccacgcctgc gctactggct ggatcgcctg aagtctgagg gcattttgga ccacgtggcc   3060

ttggtgtatg gctacttccc agcggtcgcg gaaggcgatg acgtggtgat cttggaatcc   3120

ccggatccac acgcagccga acgcatgcgc tttagcttcc cacgccagca gcgcggcagg   3180

ttcttgtgca tcgcggattt cattcgccca cgcgagcaag ctgtcaagga cggccaagtg   3240

gacgtcatgc cattccagct ggtcaccatg ggtaatccta ttgctgattt cgccaacgag   3300

ttgttcgcag ccaatgaata ccgcgagtac ttggaagttc acggcatcgg cgtgcagctc   3360

accgaagcat tggccgagta ctggcactcc cgagtgcgca gcgaactcaa gctgaacgac   3420

ggtggatctg tcgctgattt tgatccagaa gacaagacca agttcttcga cctggattac   3480

cgcggcgccc gcttctcctt tggttacggt tcttgccctg atctggaaga ccgcgcaaag   3540

ctggtggaat tgctcgagcc aggccgtatc ggcgtggagt tgtccgagga actccagctg   3600

cacccagagc agtccacaga cgcgtttgtg ctctaccacc cagaggcaaa gtactttaac   3660

gtctaa                                                              3666
```

<210> SEQ ID NO 29
<211> LENGTH: 1170
<212> TYPE: PRT
<213> ORGANISM: Streptomyces coelicolor
<220> FEATURE:
<221> NAME/KEY: misc_feature
<223> OTHER INFORMATION: methionine synthase metH

<400> SEQUENCE: 29

```
Met Ala Ser Ser Pro Ser Thr Pro Pro Ala Asp Thr Arg Thr Arg Val
1               5                   10                  15

Ser Ala Leu Arg Glu Ala Leu Ala Thr Arg Val Val Val Ala Asp Gly
```

```
            20                  25                  30

Ala Met Gly Thr Met Leu Gln Ala Gln Asn Pro Thr Leu Asp Asp Phe
        35                  40                  45

Gln Gln Leu Glu Gly Cys Asn Glu Val Leu Asn Leu Thr Arg Pro Asp
    50                  55                  60

Ile Val Arg Ser Val His Glu Glu Tyr Phe Ala Ala Gly Val Asp Cys
65                  70                  75                  80

Val Glu Thr Asn Thr Phe Gly Ala Asn His Ser Ala Leu Gly Glu Tyr
                85                  90                  95

Asp Ile Pro Glu Arg Val His Glu Leu Ser Glu Ala Gly Ala Arg Val
            100                 105                 110

Ala Arg Glu Val Ala Asp Glu Phe Gly Ala Arg Asp Gly Arg Gln Arg
        115                 120                 125

Trp Val Leu Gly Ser Met Gly Pro Gly Thr Lys Leu Pro Thr Leu Gly
    130                 135                 140

His Ala Pro Tyr Thr Val Leu Arg Asp Ala Tyr Gln Arg Asn Ala Glu
145                 150                 155                 160

Gly Leu Val Ala Gly Gly Ala Asp Ala Leu Leu Val Glu Thr Thr Gln
                165                 170                 175

Asp Leu Leu Gln Thr Lys Ala Ser Val Leu Gly Ala Arg Arg Ala Leu
            180                 185                 190

Asp Val Leu Gly Leu Asp Leu Pro Leu Ile Val Ser Val Thr Val Glu
        195                 200                 205

Thr Thr Gly Thr Met Leu Leu Gly Ser Glu Ile Gly Ala Ala Leu Thr
    210                 215                 220

Ala Leu Glu Pro Leu Gly Ile Asp Met Ile Gly Leu Asn Cys Ala Thr
225                 230                 235                 240

Gly Pro Ala Glu Met Ser Glu His Leu Arg Tyr Leu Ala Arg His Ser
                245                 250                 255

Arg Ile Pro Leu Thr Cys Met Pro Asn Ala Gly Leu Pro Val Leu Gly
            260                 265                 270

Lys Asp Gly Ala His Tyr Pro Leu Thr Ala Pro Glu Leu Ala Asp Ala
        275                 280                 285

His Glu Thr Phe Val Arg Glu Tyr Gly Leu Ser Leu Val Gly Gly Cys
    290                 295                 300

Cys Gly Thr Thr Pro Glu His Leu Arg Gln Val Val Glu Arg Val Arg
305                 310                 315                 320

Asp Thr Ala Pro Thr Ala Arg Asp Pro Arg Pro Glu Pro Gly Ala Ala
                325                 330                 335

Ser Leu Tyr Gln Thr Val Pro Phe Arg Gln Asp Thr Ser Tyr Leu Ala
            340                 345                 350

Ile Gly Glu Arg Thr Asn Ala Asn Gly Ser Lys Lys Phe Arg Glu Ala
        355                 360                 365

Met Leu Asp Gly Arg Trp Asp Asp Cys Val Glu Met Ala Arg Asp Gln
    370                 375                 380

Ile Arg Glu Gly Ala His Met Leu Asp Leu Cys Val Asp Tyr Val Gly
385                 390                 395                 400

Arg Asp Gly Val Ala Asp Met Glu Glu Leu Ala Gly Arg Phe Ala Thr
                405                 410                 415

Ala Ser Thr Leu Pro Ile Val Leu Asp Ser Thr Glu Val Asp Val Ile
            420                 425                 430

Arg Ala Gly Leu Glu Lys Leu Gly Gly Arg Ala Val Ile Asn Ser Val
        435                 440                 445
```

```
Asn Tyr Glu Asp Gly Ala Gly Pro Glu Ser Arg Phe Ala Arg Val Thr
    450                 455                 460

Lys Leu Ala Arg Glu His Gly Ala Ala Leu Ile Ala Leu Thr Ile Asp
465                 470                 475                 480

Glu Val Gly Gln Ala Arg Thr Ala Glu Lys Lys Val Glu Ile Ala Glu
                485                 490                 495

Arg Leu Ile Asp Asp Leu Thr Gly Asn Trp Gly Ile His Glu Ser Asp
            500                 505                 510

Ile Leu Val Asp Cys Leu Thr Phe Thr Ile Cys Thr Gly Gln Glu Glu
        515                 520                 525

Ser Arg Lys Asp Gly Leu Ala Thr Ile Glu Gly Ile Arg Glu Leu Lys
    530                 535                 540

Arg Arg His Pro Asp Val Gln Thr Thr Leu Gly Leu Ser Asn Ile Ser
545                 550                 555                 560

Phe Gly Leu Asn Pro Ala Ala Arg Ile Leu Leu Asn Ser Val Phe Leu
                565                 570                 575

Asp Glu Cys Val Lys Ala Gly Leu Asp Ser Ala Ile Val His Ala Ser
            580                 585                 590

Lys Ile Leu Pro Ile Ala Arg Phe Asp Glu Glu Gln Val Thr Thr Ala
        595                 600                 605

Leu Asp Leu Ile Tyr Asp Arg Arg Arg Glu Gly Tyr Asp Pro Leu Gln
    610                 615                 620

Lys Leu Met Gln Leu Phe Glu Gly Ala Thr Ala Lys Ser Leu Lys Ala
625                 630                 635                 640

Ser Lys Ala Glu Glu Leu Ala Ala Leu Pro Leu Glu Glu Arg Leu Lys
                645                 650                 655

Arg Arg Ile Ile Asp Gly Glu Lys Asn Gly Leu Glu Gln Asp Leu Asp
            660                 665                 670

Glu Ala Leu Arg Glu Arg Pro Ala Leu Glu Ile Val Asn Asp Thr Leu
        675                 680                 685

Leu Asp Gly Met Lys Val Val Gly Glu Leu Phe Gly Ser Gly Gln Met
    690                 695                 700

Gln Leu Pro Phe Val Leu Gln Ser Ala Glu Val Met Lys Thr Ala Val
705                 710                 715                 720

Ala His Leu Glu Pro His Met Glu Lys Thr Asp Asp Asp Gly Lys Gly
                725                 730                 735

Thr Ile Val Leu Ala Thr Val Arg Gly Asp Val His Asp Ile Gly Lys
            740                 745                 750

Asn Leu Val Asp Ile Ile Leu Ser Asn Asn Gly Tyr Asn Val Val Asn
        755                 760                 765

Leu Gly Ile Lys Gln Pro Val Ser Ala Ile Leu Glu Ala Ala Asp Glu
    770                 775                 780

His Arg Ala Asp Val Ile Gly Met Ser Gly Leu Leu Val Lys Ser Thr
785                 790                 795                 800

Val Ile Met Lys Glu Asn Leu Glu Glu Leu Asn Gln Arg Lys Leu Ala
                805                 810                 815

Ala Asp Tyr Pro Val Ile Leu Gly Gly Ala Ala Leu Thr Arg Ala Tyr
            820                 825                 830

Val Glu Gln Asp Leu His Glu Ile Tyr Asp Gly Glu Val Arg Tyr Ala
        835                 840                 845

Arg Asp Ala Phe Glu Gly Leu Arg Leu Met Asp Ala Leu Ile Gly Ile
    850                 855                 860

Lys Arg Gly Val Pro Gly Ala Lys Leu Pro Glu Leu Lys Gln Arg Arg
865                 870                 875                 880
```

```
Val Arg Ala Ala Thr Val Glu Ile Asp Glu Arg Pro Glu Glu Gly His
                885                 890                 895

Val Arg Ser Asp Val Ala Thr Asp Asn Pro Val Pro Thr Pro Pro Phe
            900                 905                 910

Arg Gly Thr Arg Val Val Lys Gly Ile Gln Leu Lys Glu Tyr Ala Ser
        915                 920                 925

Trp Leu Asp Glu Gly Ala Leu Phe Lys Gly Gln Trp Gly Leu Lys Gln
    930                 935                 940

Ala Arg Thr Gly Glu Gly Pro Ser Tyr Glu Glu Leu Val Glu Ser Glu
945                 950                 955                 960

Gly Arg Pro Arg Leu Arg Gly Leu Leu Asp Arg Leu Gln Thr Asp Asn
                965                 970                 975

Leu Leu Glu Ala Ala Val Val Tyr Gly Tyr Phe Pro Cys Val Ser Lys
            980                 985                 990

Asp Asp Asp Leu Ile Val Leu Asp  Asp Asp Gly Asn Glu  Arg Thr Arg
        995                 1000                1005

Phe Thr  Phe Pro Arg Gln Arg  Arg Gly Arg Arg Leu  Cys Leu Ala
    1010                1015                1020

Asp Phe  Phe Arg Pro Glu Glu  Ser Gly Glu Thr Asp  Val Val Gly
    1025                1030                1035

Phe Gln  Val Val Thr Val Gly  Ser Arg Ile Gly Glu  Glu Thr Ala
    1040                1045                1050

Arg Met  Phe Glu Ala Asn Ala  Tyr Arg Asp Tyr Leu  Glu Leu His
    1055                1060                1065

Gly Leu  Ser Val Gln Leu Ala  Glu Ala Leu Ala Glu  Tyr Trp His
    1070                1075                1080

Ala Arg  Val Arg Ser Glu Leu  Gly Phe Ala Gly Glu  Asp Pro Ala
    1085                1090                1095

Glu Met  Glu Asp Met Phe Ala  Leu Lys Tyr Arg Gly  Ala Arg Phe
    1100                1105                1110

Ser Leu  Gly Tyr Gly Ala Cys  Pro Asp Leu Glu Asp  Arg Ala Lys
    1115                1120                1125

Ile Ala  Ala Leu Leu Glu Pro  Glu Arg Ile Gly Val  His Leu Ser
    1130                1135                1140

Glu Glu  Phe Gln Leu His Pro  Glu Gln Ser Thr Asp  Ala Ile Val
    1145                1150                1155

Ile His  His Pro Glu Ala Lys  Tyr Phe Asn Ala Arg
    1160                1165                1170


<210> SEQ ID NO 30
<211> LENGTH: 1226
<212> TYPE: PRT
<213> ORGANISM: Escherichia coli
<220> FEATURE:
<221> NAME/KEY: misc_feature
<223> OTHER INFORMATION: cobalamin-dependent methionine synthase MetH

<400> SEQUENCE: 30

Ser Ser Lys Val Glu Gln Leu Arg Ala Gln Leu Asn Glu Arg Ile Leu
1               5                   10                  15

Val Leu Asp Gly Gly Met Gly Thr Met Ile Gln Ser Tyr Arg Leu Asn
            20                  25                  30

Glu Ala Asp Phe Arg Gly Glu Arg Phe Ala Asp Trp Pro Cys Asp Leu
        35                  40                  45

Lys Gly Asn Asn Asp Leu Leu Val Leu Ser Lys Pro Glu Val Ile Ala
    50                  55                  60
```

```
Ala Ile His Asn Ala Tyr Phe Glu Ala Gly Ala Asp Ile Ile Glu Thr
65                  70                  75                  80

Asn Thr Phe Asn Ser Thr Thr Ile Ala Met Ala Asp Tyr Gln Met Glu
                85                  90                  95

Ser Leu Ser Ala Glu Ile Asn Phe Ala Ala Ala Lys Leu Ala Arg Ala
            100                 105                 110

Cys Ala Asp Glu Trp Thr Ala Arg Thr Pro Glu Lys Pro Arg Tyr Val
        115                 120                 125

Ala Gly Val Leu Gly Pro Thr Asn Arg Thr Ala Ser Ile Ser Pro Asp
    130                 135                 140

Val Asn Asp Pro Ala Phe Arg Asn Ile Thr Phe Asp Gly Leu Val Ala
145                 150                 155                 160

Ala Tyr Arg Glu Ser Thr Lys Ala Leu Val Glu Gly Gly Ala Asp Leu
                165                 170                 175

Ile Leu Ile Glu Thr Val Phe Asp Thr Leu Asn Ala Lys Ala Ala Val
            180                 185                 190

Phe Ala Val Lys Thr Glu Phe Glu Ala Leu Gly Val Glu Leu Pro Ile
        195                 200                 205

Met Ile Ser Gly Thr Ile Thr Asp Ala Ser Gly Arg Thr Leu Ser Gly
    210                 215                 220

Gln Thr Thr Glu Ala Phe Tyr Asn Ser Leu Arg His Ala Glu Ala Leu
225                 230                 235                 240

Thr Phe Gly Leu Asn Cys Ala Leu Gly Pro Asp Glu Leu Arg Gln Tyr
                245                 250                 255

Val Gln Glu Leu Ser Arg Ile Ala Glu Cys Tyr Val Thr Ala His Pro
            260                 265                 270

Asn Ala Gly Leu Pro Asn Ala Phe Gly Glu Tyr Asp Leu Asp Ala Asp
        275                 280                 285

Thr Met Ala Lys Gln Ile Arg Glu Trp Ala Gln Ala Gly Phe Leu Asn
    290                 295                 300

Ile Val Gly Gly Cys Cys Gly Thr Thr Pro Gln His Ile Ala Ala Met
305                 310                 315                 320

Ser Arg Ala Val Glu Gly Leu Ala Pro Arg Lys Leu Pro Glu Ile Pro
                325                 330                 335

Val Ala Cys Arg Leu Ser Gly Leu Glu Pro Leu Asn Ile Gly Glu Asp
            340                 345                 350

Ser Leu Phe Val Asn Val Gly Glu Arg Thr Asn Val Thr Gly Ser Ala
        355                 360                 365

Lys Phe Lys Arg Leu Ile Lys Glu Glu Lys Tyr Ser Glu Ala Leu Asp
    370                 375                 380

Val Ala Arg Gln Gln Val Glu Asn Gly Ala Gln Ile Ile Asp Ile Asn
385                 390                 395                 400

Met Asp Glu Gly Met Leu Asp Ala Glu Ala Ala Met Val Arg Phe Leu
                405                 410                 415

Asn Leu Ile Ala Gly Glu Pro Asp Ile Ala Arg Val Pro Ile Met Ile
            420                 425                 430

Asp Ser Ser Lys Trp Asp Val Ile Glu Lys Gly Leu Lys Cys Ile Gln
        435                 440                 445

Gly Lys Gly Ile Val Asn Ser Ile Ser Met Lys Glu Gly Val Asp Ala
    450                 455                 460

Phe Ile His His Ala Lys Leu Leu Arg Arg Tyr Gly Ala Ala Val Val
465                 470                 475                 480

Val Met Ala Phe Asp Glu Gln Gly Gln Ala Asp Thr Arg Ala Arg Lys
```

```
                485                 490                 495

Ile Glu Ile Cys Arg Arg Ala Tyr Lys Ile Leu Thr Glu Glu Val Gly
            500                 505                 510

Phe Pro Pro Glu Asp Ile Ile Phe Asp Pro Asn Ile Phe Ala Val Ala
        515                 520                 525

Thr Gly Ile Glu Glu His Asn Asn Tyr Ala Gln Asp Phe Ile Gly Ala
    530                 535                 540

Cys Glu Asp Ile Lys Arg Glu Leu Pro His Ala Leu Ile Ser Gly Gly
545                 550                 555                 560

Val Ser Asn Val Ser Phe Ser Phe Arg Gly Asn Asp Pro Val Arg Glu
                565                 570                 575

Ala Ile His Ala Val Phe Leu Tyr Tyr Ala Ile Arg Asn Gly Met Asp
            580                 585                 590

Met Gly Ile Val Asn Ala Gly Gln Leu Ala Ile Tyr Asp Asp Leu Pro
        595                 600                 605

Ala Glu Leu Arg Asp Ala Val Glu Asp Val Ile Leu Asn Arg Arg Asp
    610                 615                 620

Asp Gly Thr Glu Arg Leu Leu Glu Leu Ala Glu Lys Tyr Arg Gly Ser
625                 630                 635                 640

Lys Thr Asp Asp Thr Ala Asn Ala Gln Gln Ala Glu Trp Arg Ser Trp
                645                 650                 655

Glu Val Asn Lys Arg Leu Glu Tyr Ser Leu Val Lys Gly Ile Thr Glu
            660                 665                 670

Phe Ile Glu Gln Asp Thr Glu Glu Ala Arg Gln Gln Ala Thr Arg Pro
        675                 680                 685

Ile Glu Val Ile Glu Gly Pro Leu Met Asp Gly Met Asn Val Val Gly
    690                 695                 700

Asp Leu Phe Gly Glu Gly Lys Met Phe Leu Pro Gln Val Val Lys Ser
705                 710                 715                 720

Ala Arg Val Met Lys Gln Ala Val Ala Tyr Leu Glu Pro Phe Ile Glu
                725                 730                 735

Ala Ser Lys Glu Gln Gly Lys Thr Asn Gly Lys Met Val Ile Ala Thr
            740                 745                 750

Val Lys Gly Asp Val His Asp Ile Gly Lys Asn Ile Val Gly Val Val
        755                 760                 765

Leu Gln Cys Asn Asn Tyr Glu Ile Val Asp Leu Gly Val Met Val Pro
    770                 775                 780

Ala Glu Lys Ile Leu Arg Thr Ala Lys Glu Val Asn Ala Asp Leu Ile
785                 790                 795                 800

Gly Leu Ser Gly Leu Ile Thr Pro Ser Leu Asp Glu Met Val Asn Val
                805                 810                 815

Ala Lys Glu Met Glu Arg Gln Gly Phe Thr Ile Pro Leu Leu Ile Gly
            820                 825                 830

Gly Ala Thr Thr Ser Lys Ala His Thr Ala Val Lys Ile Glu Gln Asn
        835                 840                 845

Tyr Ser Gly Pro Thr Val Tyr Val Gln Asn Ala Ser Arg Thr Val Gly
    850                 855                 860

Val Val Ala Ala Leu Leu Ser Asp Thr Gln Arg Asp Asp Phe Val Ala
865                 870                 875                 880

Arg Thr Arg Lys Glu Tyr Glu Thr Val Arg Ile Gln His Gly Arg Lys
                885                 890                 895

Lys Pro Arg Thr Pro Pro Val Thr Leu Glu Ala Ala Arg Asp Asn Asp
            900                 905                 910
```

```
Phe Ala Phe Asp Trp Gln Ala Tyr Thr Pro Pro Val Ala His Arg Leu
        915                 920                 925

Gly Val Gln Glu Val Glu Ala Ser Ile Glu Thr Leu Arg Asn Tyr Ile
    930                 935                 940

Asp Trp Thr Pro Phe Phe Met Thr Trp Ser Leu Ala Gly Lys Tyr Pro
945                 950                 955                 960

Arg Ile Leu Glu Asp Glu Val Val Gly Val Glu Ala Gln Arg Leu Phe
                965                 970                 975

Lys Asp Ala Asn Asp Met Leu Asp Lys Leu Ser Ala Glu Lys Thr Leu
            980                 985                 990

Asn Pro Arg Gly Val Val Gly Leu  Phe Pro Ala Asn Arg  Val Gly Asp
        995                 1000                1005

Asp Ile  Glu Ile Tyr Arg Asp  Glu Thr Arg Thr His  Val Ile Asn
    1010                 1015                1020

Val Ser  His His Leu Arg Gln  Gln Thr Glu Lys Thr  Gly Phe Ala
    1025                 1030                1035

Asn Tyr  Cys Leu Ala Asp Phe  Val Ala Pro Lys Leu  Ser Gly Lys
    1040                 1045                1050

Ala Asp  Tyr Ile Gly Ala Phe  Ala Val Thr Gly Gly  Leu Glu Glu
    1055                 1060                1065

Asp Ala  Leu Ala Asp Ala Phe  Glu Ala Gln His Asp  Asp Tyr Asn
    1070                 1075                1080

Lys Ile  Met Val Lys Ala Leu  Ala Asp Arg Leu Ala  Glu Ala Phe
    1085                 1090                1095

Ala Glu  Tyr Leu His Glu Arg  Val Arg Lys Val Tyr  Trp Gly Tyr
    1100                 1105                1110

Ala Pro  Asn Glu Asn Leu Ser  Asn Glu Glu Leu Ile  Arg Glu Asn
    1115                 1120                1125

Tyr Gln  Gly Ile Arg Pro Ala  Pro Gly Tyr Pro Ala  Cys Pro Glu
    1130                 1135                1140

His Thr  Glu Lys Ala Thr Ile  Trp Glu Leu Leu Glu  Val Glu Lys
    1145                 1150                1155

His Thr  Gly Met Lys Leu Thr  Glu Ser Phe Ala Met  Trp Pro Gly
    1160                 1165                1170

Ala Ser  Val Ser Gly Trp Tyr  Phe Ser His Pro Asp  Ser Lys Tyr
    1175                 1180                1185

Tyr Ala  Val Ala Gln Ile Gln  Arg Asp Gln Val Glu  Asp Tyr Ala
    1190                 1195                1200

Arg Arg  Lys Gly Met Ser Val  Thr Glu Val Glu Arg  Trp Leu Ala
    1205                 1210                1215

Pro Asn  Leu Gly Tyr Asp Ala  Asp
    1220                 1225
```

```
<210> SEQ ID NO 31
<211> LENGTH: 768
<212> TYPE: PRT
<213> ORGANISM: Thermotoga maritima

<400> SEQUENCE: 31

Met Arg Asn Arg Arg Glu Val Ser Lys Leu Leu Ser Glu Arg Val Leu
1               5                   10                  15

Leu Leu Asp Gly Ala Tyr Gly Thr Glu Phe Met Lys Tyr Gly Tyr Asp
            20                  25                  30

Asp Leu Pro Glu Glu Leu Asn Ile Lys Ala Pro Asp Val Val Leu Lys
        35                  40                  45
```

```
Val His Arg Ser Tyr Ile Glu Ser Gly Ser Asp Val Ile Leu Thr Asn
    50                  55                  60

Thr Phe Gly Ala Thr Arg Met Lys Leu Arg Lys His Gly Leu Glu Asp
65                  70                  75                  80

Lys Leu Asp Pro Ile Val Arg Asn Ala Val Arg Ile Ala Arg Arg Ala
                85                  90                  95

Ala Gly Glu Lys Leu Val Phe Gly Asp Ile Gly Pro Thr Gly Glu Leu
            100                 105                 110

Pro Tyr Pro Leu Gly Ser Thr Leu Phe Glu Glu Phe Tyr Glu Asn Phe
        115                 120                 125

Arg Glu Thr Val Glu Ile Met Val Glu Glu Gly Val Asp Gly Ile Ile
    130                 135                 140

Phe Glu Thr Phe Ser Asp Ile Leu Glu Leu Lys Ala Ala Val Leu Ala
145                 150                 155                 160

Ala Arg Glu Val Ser Arg Asp Val Phe Leu Ile Ala His Met Thr Phe
                165                 170                 175

Asp Glu Lys Gly Arg Ser Leu Thr Gly Thr Asp Pro Ala Asn Phe Ala
            180                 185                 190

Ile Thr Phe Asp Glu Leu Asp Ile Asp Ala Leu Gly Ile Asn Cys Ser
        195                 200                 205

Leu Gly Pro Glu Glu Ile Leu Pro Ile Phe Gln Glu Leu Ser Gln Tyr
    210                 215                 220

Thr Asp Lys Phe Leu Val Val Glu Pro Asn Ala Gly Lys Pro Ile Val
225                 230                 235                 240

Glu Asn Gly Lys Thr Val Tyr Pro Leu Lys Pro His Asp Phe Ala Val
                245                 250                 255

His Ile Asp Ser Tyr Tyr Glu Leu Gly Val Asn Ile Phe Gly Gly Cys
            260                 265                 270

Cys Gly Thr Thr Pro Glu His Val Lys Leu Phe Arg Lys Val Leu Gly
        275                 280                 285

Asn Arg Lys Pro Leu Gln Arg Lys Lys Lys Arg Ile Phe Ala Val Ser
    290                 295                 300

Ser Pro Ser Lys Leu Val Thr Phe Asp His Phe Val Val Ile Gly Glu
305                 310                 315                 320

Arg Ile Asn Pro Ala Gly Arg Lys Lys Leu Trp Ala Glu Met Gln Lys
                325                 330                 335

Gly Asn Glu Glu Ile Val Ile Lys Glu Ala Lys Thr Gln Val Glu Lys
            340                 345                 350

Gly Ala Glu Val Leu Asp Val Asn Phe Gly Ile Glu Ser Gln Ile Asp
        355                 360                 365

Val Arg Tyr Val Glu Lys Ile Val Gln Thr Leu Pro Tyr Val Ser Asn
    370                 375                 380

Val Pro Leu Ser Leu Asp Ile Gln Asn Val Asp Leu Thr Glu Arg Ala
385                 390                 395                 400

Leu Arg Ala Tyr Pro Gly Arg Ser Leu Phe Asn Ser Ala Lys Val Asp
                405                 410                 415

Glu Glu Glu Leu Glu Met Lys Ile Asn Leu Leu Lys Lys Tyr Gly Gly
            420                 425                 430

Thr Leu Ile Val Leu Leu Met Gly Lys Asp Val Pro Lys Ser Phe Glu
        435                 440                 445

Glu Arg Lys Glu Tyr Phe Glu Lys Ala Leu Lys Ile Leu Glu Arg His
    450                 455                 460

Asp Phe Ser Asp Arg Val Ile Phe Asp Pro Gly Val Leu Pro Leu Gly
465                 470                 475                 480
```

```
Ala Glu Gly Lys Pro Val Glu Val Leu Lys Thr Ile Glu Phe Ile Ser
                485                 490                 495

Ser Lys Gly Phe Asn Thr Thr Val Gly Leu Ser Asn Leu Ser Phe Gly
            500                 505                 510

Leu Pro Asp Arg Ser Tyr Tyr Asn Thr Ala Phe Leu Val Leu Gly Ile
        515                 520                 525

Ser Lys Gly Leu Ser Ser Ala Ile Met Asn Pro Leu Asp Glu Thr Leu
    530                 535                 540

Met Lys Thr Leu Asn Ala Thr Leu Val Ile Leu Glu Lys Lys Glu Leu
545                 550                 555                 560

Pro Arg Ala Glu Val Lys Glu Glu Lys Leu Val Glu Ile Ile Leu Ser
                565                 570                 575

Gly Asn Arg Ser Glu Leu Glu Lys Leu Val Glu Asp Phe Leu Lys Glu
            580                 585                 590

Lys Asp Pro Leu Ser Val Ile Glu Glu His Leu Arg Pro Ala Met Glu
        595                 600                 605

Arg Ile Gly Glu Leu Tyr Asp Lys Gly Lys Ile Phe Leu Pro Gln Leu
    610                 615                 620

Ile Leu Ala Ala Gln Thr Val Lys Pro Val Phe Asp Lys Leu Thr Ser
625                 630                 635                 640

Met Leu Pro Ser Asp Ser Gln Gly Glu Thr Phe Val Ile Ala Thr Val
                645                 650                 655

Lys Gly Asp Val His Asp Ile Gly Lys Asn Ile Val Ala Ser Val Ile
            660                 665                 670

Arg Ser Ser Gly Tyr Arg Val Val Asp Leu Gly Lys Asp Val Asp Thr
        675                 680                 685

Ser Glu Ile Val Glu Ala Val Glu Lys Glu Arg Pro Val Ala Leu Gly
    690                 695                 700

Leu Ser Ala Met Met Thr Thr Thr Val Gly Arg Ile Lys Glu Val Val
705                 710                 715                 720

Glu Lys Leu Lys Glu Lys Asn Leu Lys Ile Pro Val Ile Val Gly Gly
                725                 730                 735

Ala Ser Leu Asn Glu Lys Leu Ala Lys Glu Leu Gly Ala Asp Tyr Tyr
            740                 745                 750

Ala Lys Asn Ala Ser Glu Ala Val Lys Ile Leu Lys Ser Leu Gly Arg
        755                 760                 765
```

<210> SEQ ID NO 32
<211> LENGTH: 1068
<212> TYPE: PRT
<213> ORGANISM: Artificial
<220> FEATURE:
<223> OTHER INFORMATION: consensus sequence
<220> FEATURE:
<221> NAME/KEY: misc_feature
<223> OTHER INFORMATION: consensus sequence of metH (from Corynebacterium glutamicum, Streptomyces coelicolor, Escherichia coli and Thermotoga maritima)

<400> SEQUENCE: 32

```
Ser Ser Thr Pro Ala Ser Lys Val Ser Glu Leu Arg Asp Ala Leu Ala
1               5                   10                  15

Glu Arg Val Leu Val Leu Asp Gly Ala Met Gly Thr Met Leu Gln Ala
            20                  25                  30

Tyr Leu Asp Leu Asp Asp Phe Asp Leu Glu Gly Cys Asn Glu Ile Leu
        35                  40                  45

Asn Leu Thr Arg Pro Asp Val Val Arg Ala Ile His Arg Ala Tyr Phe
```

```
    50                  55                  60

Glu Ala Gly Ala Asp Ile Ile Glu Thr Asn Thr Phe Gly Ala Thr Ile
65                  70                  75                  80

Ala Leu Ala Asp Tyr Asp Ile Glu Asp Arg Leu Glu Ile Ala Phe Ala
                85                  90                  95

Ala Ala Arg Val Ala Arg Glu Val Ala Asp Glu Phe Gly Ala Arg Gly
            100                 105                 110

Lys Arg Phe Val Leu Gly Ser Leu Gly Pro Thr Thr Lys Leu Pro Ser
        115                 120                 125

Leu Gly His Ala Pro Phe Asp Asp Leu Arg Glu Ala Tyr Arg Glu Ser
    130                 135                 140

Ala Glu Gly Leu Val Glu Gly Gly Ala Asp Ala Ile Leu Ile Glu Thr
145                 150                 155                 160

Gln Asp Leu Leu Gln Leu Lys Ala Ala Val Leu Ala Val Arg Ala Leu
                165                 170                 175

Asp Glu Leu Gly Leu Asp Leu Pro Ile Ile Ile Ser Val Thr Val Glu
            180                 185                 190

Thr Thr Gly Thr Met Leu Ser Gly Ser Glu Ile Gly Ala Phe Leu Thr
        195                 200                 205

Ala Leu Asp Pro Leu Gly Ile Asp Met Ile Gly Leu Asn Cys Ala Thr
    210                 215                 220

Gly Pro Asp Glu Met Ser Glu His Leu Arg Tyr Leu Ser Arg His Ala
225                 230                 235                 240

Asp Ile Pro Leu Thr Val Met Pro Asn Ala Gly Leu Pro Val Leu Gly
                245                 250                 255

Lys Gly Ala Glu Tyr Pro Leu Asp Ala Asp Asp Leu Ala Ala Ile Asp
            260                 265                 270

Ser Phe Val Glu Tyr Gly Leu Ser Ile Val Gly Gly Cys Cys Gly Thr
        275                 280                 285

Thr Pro Glu His Ile Arg Ala Val Arg Lys Ala Val Gly Leu Ala Pro
    290                 295                 300

Ala Arg Asp Lys Pro Glu Ile Ala Ser Leu Tyr Ser Pro Val Pro Leu
305                 310                 315                 320

Gln Asp Thr Phe Val Met Ile Gly Glu Arg Thr Asn Ala Asn Gly Ser
                325                 330                 335

Lys Lys Phe Arg Glu Ala Met Leu Asp Gly Lys Trp Glu Asp Cys Val
            340                 345                 350

Asp Ile Ala Lys Gln Gln Val Arg Asp Gly Ala His Met Leu Asp Leu
        355                 360                 365

Asn Val Asp Tyr Val Gly Arg Asp Gly Val Ala Asp Met Glu Lys Leu
    370                 375                 380

Ala Asn Leu Leu Ala Thr Ala Ser Thr Leu Pro Ile Met Ile Asp Ser
385                 390                 395                 400

Thr Glu Val Asp Val Ile Arg Lys Gly Leu Glu Leu Gly Gly Arg Ser
                405                 410                 415

Ile Val Asn Ser Val Asn Val Glu Asp Gly Asp Gly Pro Glu Ser Arg
            420                 425                 430

Phe Arg Ile Ile Lys Leu Leu Lys Lys His Gly Ala Ala Leu Ile Val
        435                 440                 445

Leu Thr Ile Asp Glu Gly Gln Ala Arg Thr Ala Glu Lys Lys Val Glu
    450                 455                 460

Ile Ala Glu Arg Leu Ile Lys Ile Leu Thr Gly Trp Gly Ile Asp Asp
465                 470                 475                 480
```

```
Ile Ile Val Asp Pro Leu Thr Phe Pro Ile Ala Thr Gly Gln Glu Glu
                485                 490                 495

Ser Arg Lys Asp Gly Ile Glu Thr Ile Glu Ala Ile Arg Glu Ile Lys
            500                 505                 510

Arg Lys His Pro Asp Ile Asn Thr Thr Leu Gly Leu Ser Asn Ile Ser
        515                 520                 525

Phe Gly Leu Asn Pro Ala Ala Arg Leu Leu Asn Ser Val Phe Leu Glu
    530                 535                 540

Cys Ile Lys Ala Gly Leu Asp Ser Ala Ile Val Asn Ala Ser Lys Ile
545                 550                 555                 560

Leu Pro Met Arg Leu Asp Ala Glu Gln Arg Asp Ala Leu Asp Leu Ile
                565                 570                 575

Tyr Asp Arg Arg Glu Gly Tyr Asp Pro Leu Gln Glu Leu Met Gln Leu
            580                 585                 590

Phe Glu Gly Ala Ser Ala Asp Lys Ala Lys Ala Glu Glu Leu Arg Ala
        595                 600                 605

Leu Pro Leu Glu Glu Arg Leu Arg Ile Ile Asp Gly Asp Lys Asn Gly
    610                 615                 620

Leu Glu Gln Asp Leu Glu Glu Ala Leu Lys Glu Lys Ser Pro Ile Glu
625                 630                 635                 640

Ile Ile Asn Glu Leu Leu Asp Gly Met Lys Val Val Gly Glu Leu Phe
                645                 650                 655

Gly Ser Gly Gln Met Gln Leu Pro Gln Val Leu Gln Ser Ala Glu Val
            660                 665                 670

Met Lys Thr Ala Val Ala Tyr Leu Glu Pro Phe Met Glu Ala Ser Ala
        675                 680                 685

Glu Ala Gly Lys Gly Thr Ile Val Ile Ala Thr Val Lys Gly Asp Val
    690                 695                 700

His Asp Ile Gly Lys Asn Ile Val Asp Ile Ile Leu Ser Asn Asn Gly
705                 710                 715                 720

Tyr Asp Val Val Asn Leu Gly Ile Lys Val Pro Leu Ser Ala Ile Leu
                725                 730                 735

Glu Ala Ala Glu Glu His Arg Ala Asp Val Ile Gly Leu Ser Gly Leu
            740                 745                 750

Leu Val Lys Ser Thr Val Ile Met Lys Glu Val Leu Glu Glu Leu Asn
        755                 760                 765

Asn Ala Ala Tyr Pro Val Ile Leu Gly Gly Ala Ala Leu Thr Arg Ala
    770                 775                 780

Tyr Val Glu Asn Asp Leu Glu Ile Tyr Ser Gly Glu Val Tyr Tyr Ala
785                 790                 795                 800

Arg Asn Ala Ser Glu Gly Leu Arg Leu Met Asp Ala Leu Ile Ala Asp
                805                 810                 815

Lys Arg Gly Asp Ser Pro Glu Ala Lys Lys Glu Arg Lys Arg Arg Ala
            820                 825                 830

Ala Thr Leu Glu Ala Pro Asp Arg Ser Asp Val Ala Thr Asp Asn Pro
        835                 840                 845

Pro Pro Phe Gly Thr Arg Val Val Lys Gly Ile Leu Glu Phe Leu Asn
    850                 855                 860

Leu Asp Glu Ala Leu Phe Gly Gln Trp Gly Leu Lys Arg Glu Gly Pro
865                 870                 875                 880

Ser Tyr Glu Asp Leu Val Glu Ser Glu Gly Arg Pro Arg Leu Arg Leu
                885                 890                 895

Asp Arg Leu Ser Asp Leu Leu Ala Leu Val Tyr Gly Tyr Phe Pro Ala
            900                 905                 910
```

```
Val Ala Gly Asp Asp Ile Ile Ile Leu Asp Asp Asp Glu Arg Met Arg
        915                 920                 925

Phe Ser Phe Pro Arg Gln Arg Gly Arg Leu Cys Leu Ala Asp Phe Ile
    930                 935                 940

Arg Pro Lys Glu Gly Asp Val Ile Gly Phe Gln Leu Val Thr Met Gly
945                 950                 955                 960

Ile Ala Asp Ala Leu Phe Ala Ala Asn Asp Tyr Arg Asp Tyr Leu Glu
                965                 970                 975

Val His Gly Leu Ala Val Gln Leu Ala Glu Ala Leu Ala Glu Tyr Trp
            980                 985                 990

His Ala Arg Val Arg Ser Glu Leu  Ala Asp Pro Asp Glu  Asp Leu Phe
        995                 1000                1005

Leu Tyr  Arg Gly Ala Arg Phe  Ser Gly Tyr Gly Ala  Cys Pro Asp
    1010                1015                1020

Leu Glu  Asp Arg Ala Lys Ile  Glu Leu Leu Glu Pro  Glu Arg Ile
    1025                1030                1035

Gly Val  Leu Ser Glu Glu Phe  Gln Leu His Pro Glu  Gln Ser Thr
    1040                1045                1050

Asp Ala  Phe Val Ile His His  Pro Glu Ala Lys Tyr  Phe Asn Val
    1055                1060                1065
```

NUCLEIC ACID ENCODING A COBALAMIN-DEPENDENT METHIONINE SYNTHASE POLYPEPTIDE

This application is a 371 National Phase entry of PCT/EP2007/064471, filed 21 Dec. 2007, and claims the benefit of European Patent Application Serial No. 06127363.7, filed 29 Dec. 2006.

FIELD OF THE INVENTION

The present invention relates to nucleotide sequences encoding enzymatically active cobalamin-methionine synthase and functional fragments thereof being modified in comparison to the respective wild-type enzyme such that said enzymes show a reduced product inhibition by methionine. The present invention also relates to polypeptides being encoded by such nucleotide sequences and host cells comprising such nucleotide sequences. Furthermore, the present invention relates to methods for producing methionine in host organisms by making use of such nucleotide and amino acid sequences.

TECHNOLOGICAL BACKGROUND

Currently, worldwide annual production of methionine is about 500,000 tons. Methionine is the first limiting amino acid in livestock of poultry feed and due to this, mainly applied as feed supplement. In contrast to other industrial amino acids, methionine is almost exclusively applied as a racemate produced by chemical synthesis. Since animals can metabolise both stereoisomers of methionine, direct feed of the chemically produced racemic mixture is possible (D'Mello and Lewis, Effect of Nutrition Deficiencies in Animals: Amino Acids, Rechgigl (Ed.), CRC Handbook Series in Nutrition and Food, 441-490, 1978).

However, there is still a great interest in replacing the existing chemical production by a biotechnological process. This is due to the fact that at lower levels of supplementation L-methionine is a better source of sulfur amino acids than D-methionine (Katz et al., (1975) *Poult. Sci.,* 545: 1667-74). Moreover, the chemical process uses rather hazardous chemicals and produces substantial waste streams. All these disadvantages of chemical production could be avoided by an efficient biotechnological process.

For other amino acids such as glutamate, fermentation production methods are known. For these purposes, certain microorganisms such as *Escherichia coli* (*E. coli*) and *Corynebacterium glutamicum* (*C. glutamicum*) have proven to be particularly suited. The production of amino acids by fermentation also has the particular advantage that only L-amino acids are produced. Further, environmentally problematic chemicals such as solvents, etc. which are used in chemical synthesis are avoided. However, fermentative production of methionine by microorganisms will only be an alternative to chemical synthesis if it allows for the production of methionine on a commercial scale at a price comparable to that of chemical production.

Hence, the production of L-methionine through large-scale culture of bacteria developed to produce and secrete large quantities of this molecule is a desirable goal. Improvements to the process can relate to fermentation parameters, such as stirring and supply of oxygen, or the composition of the nutrient media, such as the sugar concentration during fermentation, or the working up of the product by, for instance, ion exchange chromatography, or the intrinsic output properties of the microorganism itself.

Methods of mutagenesis and mutant selection are also used to improve the output properties of these methionine-producing microorganisms. High production strains which are resistant to antimetabolites or which are auxotrophic for metabolites of regulatory importance are obtained in this manner.

Recombinant DNA technology has also been employed for some years for improving microorganism strains which produce L-amino acids by amplifying individual amino acid biosynthesis genes and investigating the effect on the amino acid production.

Rückert et al. (*Journal of Biotechnology* (2003), 104: 213-228) provide an analysis of the L-methionine biosynthetic pathway in *Corynebacterium glutamicum*. Known functions of MetZ (also known as MetY) and MetB could be confirmed and MetC (also known as AecD) was proven to be a cystathionine-β-lyase. Further, MetE and MetH, which catalyse the conversion of L-homocysteine to L-methionine, were identified in this study.

WO 02/097096 discloses nucleotide sequences from coryneform bacteria which code for the McbR repressor gene (also known as MetD) and processes for the preparation of amino acids using bacteria in which this McbR repressor gene is attenuated. According to WO 02/097096, the attenuation of the transcriptional regulator McbR improves the production of L-methionine in coryneform bacteria. It is further described in WO 02/097096 that, in addition to the attenuation of the McbR repressor gene, enhancing or overexpressing the MetB gene which codes for cystathionine-γ-synthase is preferred for the preparation of L-methionine.

Selection of strains improved for the production of a particular molecule is a time-consuming and difficult process. Therefore, there is still a great need for microorganisms which efficiently produce L-methionine and/or have significantly increased contents of L-methionine which can be utilized for obtaining methionine.

SUMMARY OF THE INVENTION

It is an object of the present invention to provide nucleotide sequences which encode enzymatically active cobalamin-dependent methionine synthases or functional fragments thereof having the property of reduced product inhibition by methionine. Such nucleotide sequences encode preferably enzymatically active cobalamin-dependent methionine synthases or functional fragments thereof which carry at least one mutation in their amino acid sequence compared to the respective wild-type amino acid sequence such that these enzymes show reduced product inhibition by methionine, i.e. the enzymatic activity is inhibited by methionine to a lesser extent than for the wild-type enzymes and polypeptides. Such nucleotide sequences may e.g. be DNA and/or RNA sequences with DNA sequences being preferred.

It is a further object of the present invention to provide polypeptides and preferably proteins which are encoded by such nucleotide sequences.

Yet another object of the present invention is to provide vectors which comprise such nucleotide sequences and can be used for expression of such nucleotide sequences and polypeptides in host cells.

Another object of the present invention relates to host cells which express the aforementioned nucleotide and polypeptide sequences.

Yet another object of the present invention relates to the use of such nucleotide and polypeptide sequences for producing methionine and/or increasing the efficiency of methionine production in host organisms.

The present invention also relates to methods for producing methionine by expressing said nucleotide and polypeptide sequences in host organisms.

According to one embodiment of the invention, nucleotide and preferably DNA sequences are provided which encode an enzymatically active cobalamin-dependent methionine synthase or functional fragments thereof having the property of reduced product inhibition by methionine. In one embodiment such nucleotide and preferably DNA sequences encode enzymatically active cobalamin-dependent methionine synthases or functional fragments thereof which carry at least one mutation in their amino acid sequence compared to the respective wild-type amino acid sequences, such that the enzymatic activity of said enzymatically active cobalamin-dependent methionine synthases or of said functional fragments shows reduced product inhibition as a consequence of the at least one mutation. This means that the enzymatic activity of the mutated enzymes or functional fragments thereof is inhibited by methionine to a lesser extent compared to the respective wild-type sequences.

Such nucleotide and preferably DNA sequences may also allow the construction of host organisms which product and secrete preferably large quantities of the desired molecule, i.e. L-methionine.

In a further embodiment of the present invention, such nucleotide and preferably DNA sequences encode enzymatically active cobalamin-dependent methionine synthases or functional fragments thereof which carry at least one mutation in SEQ ID NO: 1 such that the encoded polypeptides show reduced product inhibition by methionine compared to the respective wild-type polypeptides.

Yet another embodiment of the present invention relates to nucleotide and preferably DNA sequences that encode enzymatically active cobalamin-dependent methionine synthases or functional fragments thereof which carry at least one mutation in their homocysteine-binding domain such that these polypeptides show reduced product inhibition by methionine. A typical homocysteine-binding domain is that of MetH of *C. glutamicum*. The corresponding DNA sequence is SEQ ID NO: 24 while the amino acid sequence is SEQ ID NO: 2.

In yet another embodiment of the present invention, nucleotide and preferably DNA sequences encode enzymatically active cobalamin-dependent methione synthases or functional fragments thereof which carry at least one mutation in SEQ ID NOs: 3 to 18 such that these polyp eptides show reduced product inhibition by methionine.

One embodiment of the present invention relates to nucleotide and preferably DNA sequences which encode enzymatically active cobalamin-dependent methionine synthases or functional fragments thereof which carry at least one mutation in a position corresponding to M33, F86 or S134 of the cobalamin-dependent methionine synthase MetH of *C. glutamicum*. The DNA sequence of MetH of *C. glutamicum* is that of SEQ ID NO: 23. The amino acid sequence of MetH of *C. glutamicum* is that of SEQ ID NO: 1.

The present invention in one embodiment also relates to nucleotide and preferably DNA sequences which encode polypeptides that are at least 50%, at least 60%, at least 70%, at least 80%, at least 85%, at least 90%, at least 95%, at least 96%, at least 97%, at least 98% or at least 99% identical to the polypeptides being encoded by the afore-mentioned nucleotide sequences which carry at least one mutation in these sequences compared to the wild-type sequences such that the resulting enzymatically active cobalamin-dependent methionine synthases or functional fragments thereof show reduced product inhibition by methionine.

Thus, the present invention on one embodiment relates to nucleotide and preferably DNA sequences which encode polypeptides that are at least 50%, at least 60%, at least 70%, at least 80%, at least 85%, at least 90%, at least 95%, at least 96%, at least 97%, at least 98% or at least 99% identical to the polypeptides being encoded by any of SEQ ID NOs: 1 to 18 with the proviso that these polypeptides carry at least one mutation in these sequences such that the resulting enzymatically active cobalamin-dependent methionine synthases or functional fragments thereof show reduced product inhibition by methionine.

Yet another embodiment of the present invention relates to nucleotide and preferably DNA sequences that are at least 30%, at least 40%, at least 50%, at least 60%, at least 70%, at least 80%, at least 85%, at least 90%, at least 95%, at least 96%, at least 97%, at least 98% or at least 99% identical to the aforementioned nucleotide and preferably DNA sequences.

Thus, in one embodiment the present invention relates to nucleotide and preferably DNA sequences that are at least 30%, at least 40%, at least 50%, at least 60%, at least 70%, at least 80%, at least 85%, at least 90%, at least 95%, at least 96%, at least 97%, at least 98% or at least 99% identical to e.g. SEQ ID NO: 23 or SEQ ID NO: 24 with the proviso that the nucleotide sequences carry additionally at least one mutation such that the resulting enzymatically active cobalamin-dependent methionine synthases or functional fragments thereof show reduced product inhibition by methionine.

In preferred embodiments these nucleotide and preferably DNA sequences are isolated or recombinant nucleotide and preferably DNA sequences.

Another embodiment of the present invention relates to nucleotide and preferably DNA sequences that hybridise under stringent conditions to the aforementioned nucleotide sequences.

Other embodiments of the present invention relate to nucleotide and preferably DNA sequences encoding enzymatically active cobalamin-dependent methionine synthases or functional fragments thereof which carry at least one mutation with respect to the corresponding wild type sequences, the enzymatic activity of which is at least 10%, 20%, 30%, 40%, 50%, 60%, 70%, 80%, 90%, 100% and preferably at least a factor of 2, 3, 4, 5, 10, 20, 50, 100, 200, 500 or 1000 less inhibited in the presence of 20 mM methionine compared to respective wild-type cobalamin-dependent methionine synthases or functional fragments thereof.

The present invention also relates to vectors which comprise the aforementioned nucleotide and preferably DNA sequences in operative linkage to promoter and termination sequences such that these nucleotide sequences can be expressed in host organisms.

Other embodiments of the present invention relate to polypeptides which are encoded by the aforementioned nucleotide and preferably DNA sequences.

Yet another embodiment of the present invention relates to host cells which comprise the aforementioned nucleotide and preferably DNA sequences.

In one embodiment of the present invention, such host cells express the aforementioned nucleotide and preferably DNA sequences, preferably from one of the aforementioned vectors.

According to a further embodiment of the present invention, such host cells are selected from microorganisms and yeasts. In one embodiment, the microorganism is selected from the group consisting of e.g. coryneform bacteria, microbacteria, streptomycetaceae, salmonella, *Escherichia coli, Shigella, Bacillus, Serratia, Pseudomonas, S. coel* or *Thermotoga maritima.*

While any host cell or host organism in accordance with the present invention must comprise the above mentioned nucleotide and preferably DNA sequences which encode for enzymatically active cobalamin-dependent methionine synthases or functional fragments thereof having reduced product inhibition by menthionine, one embodiment of the present invention relates to host cells in which additionally the endogenous gene(s) for cobalamin-dependent methionine synthase(s) is/are deleted or functionally disrupted.

Other embodiments of the invention relate to host cells and host organisms in which at least one of the nucleotide and preferably DNA sequences in accordance with the present invention is expressed and in which the amount and/or activity of at least one polypeptide being encoded by the following nucleotide sequences is increased in comparison to the corresponding initial host organism:

- nucleotide sequence coding for aspartate kinase lysC,
- nucleotide sequence coding for glycerine aldehyde-3-phosphate dehydrogenase gap,
- nucleotide sequence coding for 3-phosphoglycerate kinase pgk,
- nucleotide sequence coding for pyruvatecarboxylase pyc,
- nucleotide sequence coding for triosephosphate isomerase tpi,
- nucleotide sequence coding for homoserin-O-acetyltransferase metA,
- nucleotide sequence coding for cystathione-gamma-synthase metB,
- nucleotide sequence coding for cystathione-gamma-lyase metC,
- nucleotide sequence coding for serine-hydroxymethyl transferase glyA,
- nucleotide sequence coding for O-acetylhomoserine-sulfhydrylase metY,
- nucleotide sequence coding for phosphoserine aminotransferase serC,
- nucleotide sequence coding for phosphoserine-phosphatase serB,
- nucleotide sequence coding for serine acetyltransferase cyse,
- nucleotide sequence coding for homoserine-dehydrogenase hom,
- nucleotide sequence coding for methionine synthase metE,
- nucleotide sequence coding for phosphoadenosine-phosphosulfate-reductase cysH,
- nucleotide sequence coding for sulfate adenylyl transferase-subunit I,
- nucleotide sequence coding for CysN-sulfate adenylyl transferase-subunit 2,
- nucleotide sequence coding for ferredoxine-NADP-reductase,
- nucleotide sequence coding for ferredoxine,
- nucleotide sequence coding for glucose-6-phosphate-dehydrogenase, and/or
- nucleotide sequence coding for fructose-1-6-bisphosphatase.

Another embodiment of the present invention relates to host cells and host organisms in which one of the nucleotide and preferably DNA sequences in accordance with the present invention is expressed and in which additionally the amount and/or activity of at least one polypeptide being encoded by the following nucleotide sequences is decreased with respect to the corresponding initial organism:

- nucleotide sequence coding for homoserine kinase thrB,
- nucleotide sequence coding for threonine dehydratase ilvA,
- nucleotide sequence coding for threonine synthase thrC,
- nucleotide sequence coding for meso-diaminopimelate-D-dehydrogenase ddh,
- nucleotide sequence coding for phosphoenolpyruvate carboxy kinase pck,
- nucleotide sequence coding for glucose-6-phosphate-6-isomerase pgi,
- nucleotide sequence coding for pyruvate-oxidase poxB,
- nucleotide sequence coding for dihydrodipicolinate synthase dapA,
- nucleotide sequence coding for dihydrodipicolinate reductase dapB,
- nucleotide sequence coding for diaminopicolinate-decarboxylase lysA,
- nucleotide sequence coding for glycosyl transferase and/or
- nucleotide sequence coding for lactate hydrogenase.

Another aspect of the invention relates to host cells and organisms in which the efficiency and/or yield and/or amount of methionine production is increased by at least 10%, 20%, 30%, 40%, 50%, 60%, 70%, 80%, 90%, 100% and preferably at least by a factor of 2, 3, 4, 5, 10, 20, 50, 100 or 1000 in comparison to a host cell or host organism in which no nucleotide sequence in accordance with the invention is expressed.

Other embodiments of the present invention relate to methods for producing methionine in a host cell or organism wherein a nucleotide and preferably DNA or polypeptide sequence in accordance with the invention is expressed in the host cell. Other embodiments of the present invention relate to methods for producing methionine wherein one of the aforementioned host cells is used.

One aspect of the present invention relates to a method for producing methionine in which one of the aforementioned host cells is cultivated and methionine is subsequently isolated. The present invention also relates to the use of the aforementioned host cells for producing methionine and to the use of nucleotide and preferably DNA sequences in accordance with the present invention to produce methionine and host cells which are useful in producing methionine.

DESCRIPTION OF THE DRAWINGS

FIG. 2 shows a sequence alignment of the cob(I)alamin-dependent methionine synthases of *C. glutamicum, S. coel, E. coli* and *Thermotoga maritima.*

FIG. 3 depicts the amino acid sequence (SEQ ID NO: 1, a)) and DNA sequence (SEQ ID NO: 23), b)) of cob(I)alamin-dependent methionine synthase MetH of *C. glutamicum.*

FIG. 4 depicts the amino acid sequence (SEQ ID NO: 2, b)) and DNA sequence (SEQ ID NO: 24, b)) of the homocysteine binding domain of cob(I)alamin-dependent methionine synthase MetH of *C. glutamicum* comprising amino acids 1 to 244.

FIG. 5 depicts amino acid sequences (SEQ ID NOs: 3 to 18) of conserved regions within the homocysteine binding domain of cob(I)alamin-dependent methionine synthases of *C. glutamicum, S. coel, E. coli* and *Thermotoga maritima.*

FIG. 7 depicts the amino acid sequence (SEQ ID NO: 20, a)) and DNA sequence (SEQ ID NO: 26, b)) of the cob(I) alamin-dependent methionine synthase MetH of *C. glutamicum* carrying a M33L mutation.

FIG. 8 depicts the amino acid sequence (SEQ ID NO: 21, a)) and DNA sequence (SEQ ID NO: 27, b)) of the cob(I) alamin-dependent methionine synthase MetH of *C. glutamicum* carrying a F86L mutation.

FIG. 9 depicts the amino acid sequence (SEQ ID NO: 22, a)) and DNA sequence (SEQ ID NO: 28, b)) of the cob(I) alamin-dependent methionine synthase MetH of *C. glutamicum* carrying a S134N mutation.

DETAILED DESCRIPTION OF EXEMPLARY EMBODIMENTS

Before describing in detail exemplary embodiments of the present invention, the following definitions are given.

The terms "nucleotide sequences in accordance with the present invention" and "DNA sequences in accordance with the present invention" refer to the corresponding sequences as mentioned above that encode polypeptides being enzymatically active cobalamin-dependent methionine synthases or functional fragments thereof that show a reduced product inhibition by methionine. The term "reduced product inhibition by methionine" will be defined further below. The term "polypeptide" means to encompass proteins and typically relates to polypeptides with more than 20 amino acids.

The term "efficiency of methionine synthesis" describes the carbon yield of methionine. This efficiency is calculated as a percentage of the energy input which enters the system in the form of a carbon substrate. Throughout the invention this value is given in percent values ((mol methionine) (mol carbon substrate)$^{-1}\cdot$100), unless indicated otherwise. Preferred carbon sources according to the present invention are sugars, such as mono-, di-, or polysaccharides. For example, sugars selected from the group consisting of glucose, fructose, manose, galactose, libose, sorbose, lactose, maltose, sucrose, raffinose, starch or cellulose may serve as particularly preferred carbon sources.

The term "increased efficiency of methionine synthesis" relates to the comparison between an organism being a host cell that has been genetically modified to express nucleotide and preferably DNA sequences in accordance with the present invention and which has a higher efficiency of methionine synthesis compared to the initial organism which does not express the nucleotide and preferably the DNA sequences in accordance with the present invention.

The initial organism which does not express nucleotide and preferably DNA sequences in accordance with the present invention may be a wild-type organism. Alternatively, it may be an organism that has already been optimised for methionine production and thus over-expresses certain genes of the methionine synthesis pathway. Alternatively, an initial organism which has already been optimised for methionine production may show a reduced expression for certain enzymes of the methionine pathway.

Figure 1:
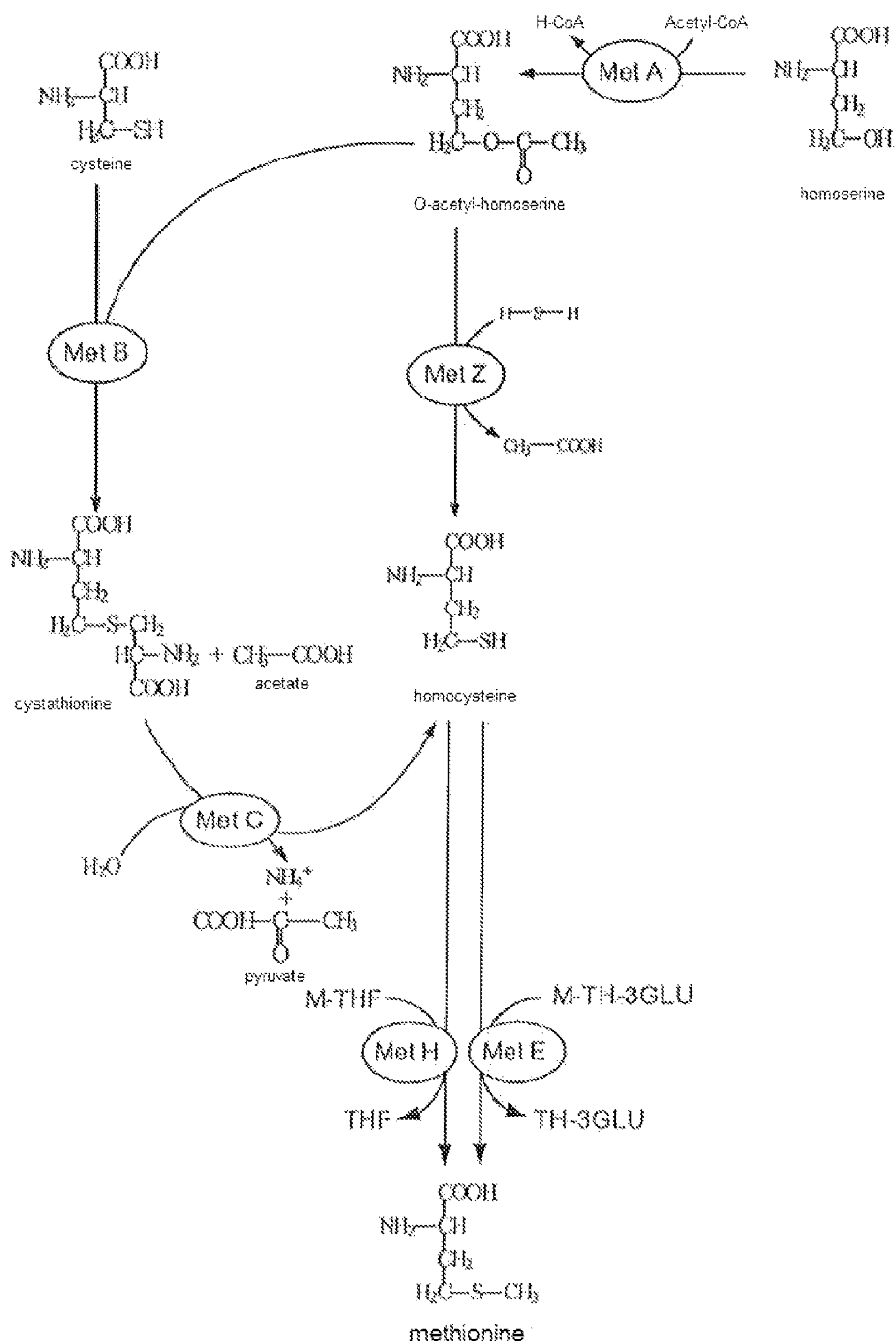
FIG. 1 is a model of the pathway for L-methionine biosynthesis in microorganisms such as *C. glutamicum*. Enzymes involved are MetA (homoserine transacetylase), MetB (cystathione-gamma-synthase), MetZ (O-acetylhomoserine sulfhydrolase), MetC (cystathione-beta-lyase), cob(I)alamin-dependent methionine synthase I (MetH) and cob(I)alamin-independent methionine synthase II (MetE).
Figure 6:
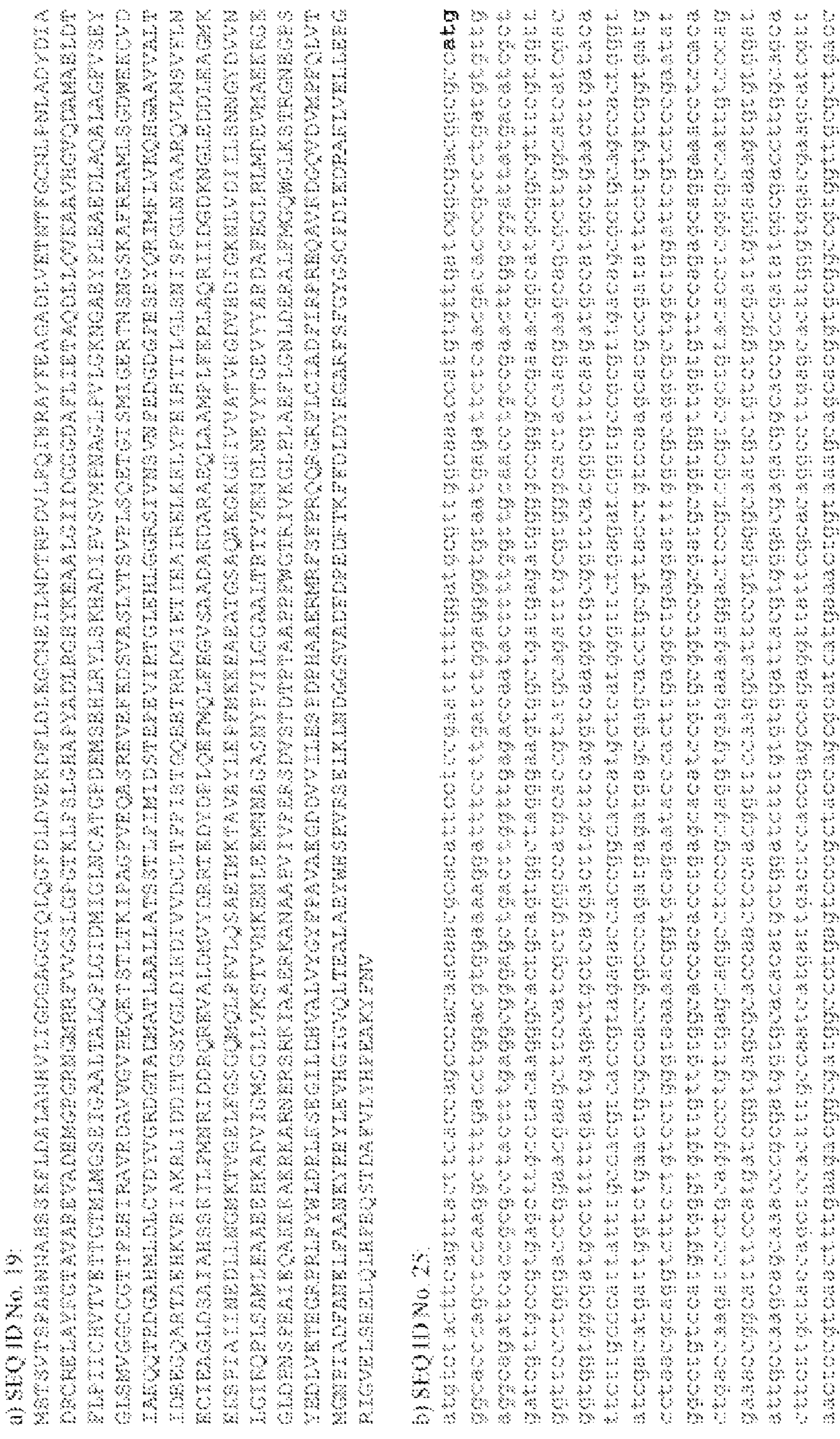
FIG. 6 depicts the amino acid sequence (SEQ ID NO: 19, a)) and DNA sequence (SEQ ID NO: 25, b)) of the cob(I) alamin-dependent methionine synthase MetH of *C. glutamicum* carrying a M33A mutation.

The terms "methionine pathway" and "methionine biosynthesis pathway" are art-recognised and describe a series of reactions which take place in a wild-type organism and lead to the biosynthesis of L-methionine. These pathways may vary from organism to organism. The details of an organism-specific pathway can be taken from textbooks and the scientific literature on the interne website HyperTextTransferProtocol://WorldWideWeb.genome.jp/kegg/metabolism.HyperTextMarkupLanguage, wherein "HyperTextTransferProtocol"= "http", "WorldWideWeb"="www", and "HyperTextMarkupLanguage"="html". In particular, a methionine pathway within the meaning of the present invention is shown in FIG. 1.

The term "yield of methionine" describes the yield of methionine which is calculated as the amount of methionine obtained per weight cell mass.

The terms "organism", "host organism", "host cell" or "microorganism" for the purposes of the present invention refer to any organism that is commonly used for the production of amino acids such as methionine. In particular, these terms relate to procaryots, lower eucaryots and fungi. A preferred group of the above-mentioned organisms comprises actino bacteria, cyano bacteria, proteo bacteria, *Chloroflexus aurantiacus, Pirellula* sp. 1, halo bacteria and/or methanococci, preferably coryneform bacteria, myco bacteria, streptomyces, salmonella, *Escherichia coli, Shigella, Pseudomonas, S. coel* or *Thermotoga maritima.*

Particularly preferred microorganisms are selected from *Corynebacterium glutamicum, Escherichia coli*, microorganisms of the genus *Bacillus*, particularly *Bacillus subtilis*, microorganisms of the genus *Streptomyces*, or of the genus *Thermotoga*, particularly *Thermotoga maritima.*

The organisms of the present invention may, however, also comprise yeasts such as *Schizosaccharomyces pombe* or *S. cerevisiae* and *Pichia pastoris.*

The terms "L-methionine over-producing organism", "methionine over-producing organism" or "methionine-producing organism" for the purposes of the present invention refer to an "organism", "host organism" or "microorganism" in which compared to an initial organism which does not express nucleotide and preferably DNA sequences in accordance with the present invention, the efficiency and/or yield and/or amount of methionine production is increased at least by 10%, 20%, 30%, 40%, 50%, 60%, 70%, 80%, 90%, 100% or at least by a factor of 2, 3, 4, 5, 10, 15, 20, 50, 100, 500 and 1000 or more.

The term "metabolite" refers to chemical compounds that are used in the metabolic pathways of organisms as precursors, intermediates and/or end products. Such metabolites may not only serve as chemical building units, but may also exert a regulatory activity on enzymes and their catalytic activity. It is known from the literature that such metabolites may inhibit or stimulate the activity of enzymes (Stryer, Biochemistry, (1995) W.H. Freeman & Company, New York, N.Y.).

For the purposes of the present invention, the term "external metabolite" comprises substrates such as glucose, sulfate, thiosulfate, sulfite, sulfide, ammonia, oxygen etc.

If, in the context of the present invention, reference is made to the content of a nucleotide sequence or the content of a polypeptide encoded by the nucleotide sequence, this refers to the amount of nucleic acid and polypeptide being encoded by such nucleic sequences as they can be determined for the respective host organism comprising such nucleotide sequences or polypeptides.

If reference is made to the activity of a nucleotide sequence this typically, for the purposes of the present invention, means to encompass the activity of the polypeptide or protein that is encoded by such a nucleotide sequence.

If, in the context of the present invention, it is stated that the amount of nucleotide sequence is increased with respect to a wild-type or initial organism, this means that the amount of this nucleotide sequence and the amount of the polypeptide that is encoded by the nucleic acid are increased in comparison to an organism which is not genetically manipulated with respect to this specific nucleotide sequence or polypeptide.

This may be achieved by introducing a corresponding exogenous nucleotide sequence into a host organism and the comparison then refers to the host organism expressing the nucleotide sequence and the initial organism into which the nucleotide sequence has not been introduced. Alternatively, the amount of nucleotide sequence may be increased by manipulating other regulatory sequences or the endogenous sequences within an organism.

Thus, increasing the amount of a nucleotide sequence may be achieved by introducing exogenous sequences or manipulating endogenous sequences that are responsible for the level of expression of the respective nucleotide sequences.

If, in the context of the present invention, it is stated that the activity of a nucleotide sequence is increased with respect to an initial organism, this refers to a situation where typically the activity of the polypeptide that is encoded by this nucleotide sequence is increased in comparison to the initial organism. Increasing the activity may be achieved by increasing the amount of the nucleotide sequence, and/or by introducing mutations in nucleotide sequences encoding polypeptides with increased activity.

Thus, increasing the activity of a nucleotide sequence and the polypeptide being encoded thereby may be achieved by either introducing exogenous nucleotide sequences and/or introducing mutations into the regulatory and coding sequences of endogenous sequences that are responsible for expressing the sequence of interest.

If, in the context of the present invention, it is stated that the content (amount) and/or activity of a nucleotide sequence, and consequently of the polypeptide being encoded thereby, is decreased in comparison to an initial organism, the above definitions are to be applied mutatis mutandis.

The terms "express," "expressing," "expressed" and "expression" refer to expression of a gene product (e.g., a biosynthetic enzyme of a gene of a pathway or reaction defined and described in this application) or a nucleotide sequence. The expression can be done by genetic alteration of the e.g. microorganism that is used as an initial starting organism. In some embodiments, a microorganism can be genetically altered (e.g., genetically engineered) to express a gene product such as a polypeptide at an increased level relative to that produced by the initial microorganism or in a comparable microorganism which has not been altered. Genetic alteration includes, but is not limited to, altering or modifying regulatory sequences or sites associated with expression of a particular gene (e.g. by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins).

The terms "overexpress", "overexpressing", "overexpressed" and "overexpression" refer to expression of a gene product (e.g. a methionine biosynthetic enzyme or a gene or a pathway or a reaction defined and described in this application) or a nucleotide sequence at a level greater than that present prior to a genetic alteration of the initial microorganism. In some embodiments, a microorganism can be genetically altered (e.g., genetically engineered) to express a gene product or nucleotide sequence at an increased level relative to that produced by the initial microorganism. Genetic alteration includes, but is not limited to, altering or modifying regulatory sequences or sites associated with expression of a particular gene (e.g., by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins). Examples for the overexpression of genes in organisms such as *C. glutamicum* can be found in Eikmanns et al (*Gene*. (1991) 102, 93-8).

In some embodiments, a microorganism can be physically or environmentally altered to express a gene product or nucleotide sequence at an increased or lower level relative to level of expression of the gene product or nucleotide sequence by the initial microorganism. For example, a microorganism can be treated with or cultured in the presence of an agent known or suspected to increase transcription of a particular nucleotide sequence and/or translation of a particular nucleotide sequence such that transcription and/or translation are enhanced or increased. Alternatively, a microorganism can be cultured at a temperature selected to increase transcription of a particular nucleotide sequence or gene and/or translation of a particular nucleotide sequence or gene product such that transcription and/or translation are enhanced or increased.

The terms "disrupt", "disrupted", "disruption", "deregulate," "deregulated" and "deregulation" refer to alteration or modification of at least one gene or nucleotide sequence in e.g. a microorganism, wherein the alteration or modification results in increasing efficiency or yield of methionine production in the microorganism relative to methionine production in absence of the alteration or modification. In some embodiments, a gene or nucleotide sequence that is altered or modified encodes an enzyme in a biosynthetic pathway, such that the level or activity of the biosynthetic enzyme in the microorganism is altered or modified. In some embodiments, at least one gene that encodes an enzyme in a biosynthetic pathway is altered or modified such that the level or activity of the enzyme is enhanced or increased relative to the level in presence of the unaltered or wild type gene. In some embodiments, the biosynthetic pathway is the methionine biosynthetic pathway. Deregulation also includes altering the coding region of one or more genes to yield, for example, an enzyme that is feedback resistant or has a higher or lower specific activity. Also, deregulation further encompasses genetic alteration of genes encoding transcriptional factors (e.g., activators, repressors) which regulate expression of genes in the methionine and/or cysteine biosynthetic pathway.

The phrase "deregulated pathway or reaction" refers to a biosynthetic pathway or reaction in which at least one gene that encodes an enzyme in a biosynthetic pathway or reaction is altered or modified such that the level or activity of at least one biosynthetic enzyme is altered or modified. The phrase "deregulated pathway" includes a biosynthetic pathway in which more than one gene has been altered or modified, thereby altering level and/or activity of the corresponding gene products/enzymes. In some cases the ability to "deregulate" a pathway (e.g., to simultaneously deregulate more than one gene in a given biosynthetic pathway) in a microorganism arises from the particular phenomenon of microorganisms in which more than one enzyme (e.g., two or three biosynthetic enzymes) are encoded by genes occurring adjacent to one another on a contiguous piece of genetic material termed an "operon." In other cases, in order to deregulate a pathway, a number of genes must be deregulated in a series of sequential engineering steps.

The term "operon" refers to a coordinated unit of genetic material that contains a promoter and possibly a regulatory element associated with one or more, preferably at least two, structural genes (e.g., genes encoding enzymes, for example, biosynthetic enzymes). Expression of the structural genes can be coordinately regulated, for example, by regulatory proteins binding to the regulatory element or by anti-termination of transcription. The structural genes can be transcribed to give a single mRNA that encodes all of the structural proteins. Due to the coordinated regulation of genes included in an operon, alteration or modification of the single promoter and/or regulatory element can result in alteration or modification of each gene product encoded by the operon. Alteration or modification of a regulatory element includes, but is not limited to, removing endogenous promoter and/or regulatory element(s), adding strong promoters, inducible promoters or multiple promoters or removing regulatory sequences such that expression of gene products is modified, modifying the chromosomal location of the operon, altering nucleic acid sequences adjacent to the operon or within the operon such as a ribosome binding site, codon usage, increasing copy number of the operon, modifying proteins (e.g., regulatory proteins, suppressors, enhancers, transcriptional activators and the like) involved in transcription of the operon and/or translation of the gene products of the operon, or any other conventional means of deregulating expression of genes routine in the art (including, but not limited to, use of antisense nucleic acid molecules, for example, to block expression of repressor proteins).

In some embodiments, recombinant microorganisms described herein have been genetically engineered to overexpress a bacterially derived gene or gene product. The terms "bacterially-derived" and "derived-from bacteria" refer to a gene which is naturally found in bacteria or a gene product which is encoded by a bacterial gene.

Amino acids comprise the basic structural units of all proteins, and as such are essential for normal cellular functioning in organisms. The term "amino acid" is well known in the art. The proteinogenic amino acids, of which there are 20 species, serve as structural units for proteins, in which they are linked by peptide bonds, while the non-proteinogenic amino acids are not normally found in proteins (see Ullmann's Encyclopaedia of Industrial Chemistry, Vol. A2, pages 57-97, VCH, Weinheim (1985)). Amino acids may be in the D- or L-optical configuration, although L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, 3rd edition, pages 578-590 (1988)).

The essential amino acids, i.e. histidine, isoleucine, leucine, lysine, methionine, phenylalanine, threonine, tryptophan and valine, which are generally a nutritional requirement due to the complexity of their biosynthesis, are readily converted by simple biosynthetic pathways to the remaining 11 non-essential amino acids, i.e. alanine, arginine, asparagine, aspartate, cysteine, glutamate, glutamine, glycine, proline, serine and tyrosine.

Higher animals retain the ability to synthesize some of these amino acids, but the essential amino acids must be supplied from the diet in order for normal protein synthesis to occur. Apart from their function in protein biosynthesis, these amino acids are interesting chemicals in their own right, and many have been found to have various applications in the food, feed, chemical, cosmetic, agricultural and pharmaceutical industries.

Lysine is an important amino acid in the nutrition not only of humans, but also of monogastric animals, such as poultry and swine. Glutamate is most commonly used as a flavour additive, and is widely used throughout the food industry as are aspartate, phenylalanine, glycine and cysteine. Glycine, L-methionine and tryptophan are all utilized in the pharmaceutical industry. Glutamine, valine, leucine, isoleucine, histidine, arginine, proline, serine and alanine are of use in both the pharmaceutical and cosmetic industries. Threonine, tryptophan and D/L-methionine are common feed additives (Leuchtenberger, W. (1996), Amino acids—technical production and use, p. 466-502 in Rehm et al. (editors) Biotechnology, Vol. 6, Chapter 14a, VCH: Weinheim). Additionally, these amino acids have been found to be useful as precursors for the synthetic of synthetic amino acids and proteins such as N-acetyl cysteine, S-carboxymethyl-L-cysteine, (S)-5-hydroxytryptophan and others described in Ullmann's Encyclopaedia of Industrial Chemistry, Vol. A2, p. 57-97, VCH: Weinheim, 1985.

The biosynthesis of these natural amino acids in organisms capable of producing them, such as bacteria, has been well characterized (for review of bacterial amino acid biosynthesis and regulation therefor (see Umbarger H. E. (1978), *Ann. Rev. Biochem.* 47:533-606). Glutamate is synthesized by the reductive amination of α-ketoglutarate, an intermediate in the citric acid cycle. Glutamine, proline and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by transferral of the side-chain β-carbon atom to tetrahydrofolate, in a reaction catalysed by serine transhydroxymethylase. Phenylalanine and tyrosine are synthesized from the glycolytic and pentose phosphate pathway precursors erythrose-4-phosphate and phosphoenolpyruvate in a nine-step biosynthetic pathway that differ only at the final two steps after the synthesis of prephenate. Tryptophan is also produced from these two initial molecules, but its synthesis is an eleven-step pathway. Tyrosine may also be synthesized from phenylalanine in a reaction catalysed by phenylalanine hydroxylase. Alanine, valine and leucine are all biosynthetic products of pyruvate, the final product of glycolysis. Aspartate is formed from oxaloacetate, an intermediate of the citric acid cycle. Asparagine, methionine, threonine and lysine are each produced by the conversion of aspartate. Isoleucine may be formed from threonine. A complex nine-step pathway results in the production of histidine from 5-phosphoribosyl-1-pyrophosphate, an activated sugar.

Amino acids in excess of the protein synthesis needs of the cell cannot be stored and are instead degraded to provide intermediates for the major metabolic pathways of the cell (for review see Stryer, L., Biochemistry, 3rd edition, Chapter 21 "Amino acid degradation and the urea cycle", p. 495-516 (1988)). Although the cell is able to convert unwanted amino acids into useful metabolic intermediates, amino acid production is costly in terms of energy, precursor molecules, and the enzymes necessary to synthesise them.

Amino acid biosynthesis can be regulated by feedback inhibition, in which the presence of a particular amino acid serves to slow or entirely stop its own production (for overview of feedback mechanisms in amino acid biosynthetic pathways, see Stryer, L., Biochemistry, 3rd edition, Chapter 24: "Biosynthesis of amino acids and heme", p. 575-600 (1988)). If this feedback inhibition is mediated by an amino acid forming the product of the regulated reaction or pathway, one typically speaks of "product inhibition". Thus, the output of any particular amino acid is limited by the amount of that amino acid present in the cell.

The Gram-positive soil bacterium *Corynebacterium glutamicum* is widely used for the industrial production of different amino acids. Whereas the biosynthesis of lysine and glutamate, the main industrial products, has been studied for many years, knowledge about the regulation of the methionine biosynthetic pathway is limited.

However, at least the key enzymes of the pathway are known (see FIG. 1). *C. glutamicum* activates homoserine by acetylation with homoserine-O-acetyltransferase (MetA) (EC 2.3.1.31). It was further shown that both transsulfuration and direct sulfhydrylation are used to produce homocysteine (Hwang et al. (2002), *J. Bacteriol.,* 1845: 1277-86). Transsulfuration is catalyzed by cystathionine-γ-synthase (MetB) (EC 2.5.1.48) (Hwang et al. (1999) *Mol Cells,* 93: 300-8). In this reaction, cysteine and O-acetyl-homoserine are combined to cystathionine, which is hydrolyzed by the cystathionine-β-lyase (MetC which is also known as AecD) (EC 4.4.1.8) (Kim et al. (2001), Mol. Cell, 112:220-5, Ruckert et al. (2003), vide supra) converts O-acetylhomoserine and sulfide into homocysteine and acetate. Finally, *C. glutamicum* has two different enzymes for the S-methylation of homocysteine yielding methionine (Lee et al. (2003), *Appl. Microbiol. Biotechnol.* 625-6, 459,67; Ruckert et al. (2003), vide supra), i.e. a cob(I)alamin dependent methionine synthase I (MetH) (EC 2.1.1.13) and a cob(I)alamin independent methionine synthase II (MetE) (EC 2.1.1.14). The former utilizes 5-methyltetrahydrofolate and the latter 5-methyltetrahydropteroyltri-L-glutamate as the methyl donor.

Recently, a putative transcriptional regulator protein of the TetR-family was found (Rey et al. (2003), *Journal of Biotechnology,* 103: 51-65). This regulator was shown to repress the transcription of several genes belonging to methionine and sulfur metabolism. The gene knockout of the regulator protein led to an increased expression of hom encoding homoserine dehydrogenase, metZ encoding O-acetylhomoserine sulfhydrolase, metK encoding S-adenosylmethionine (SAM) synthase (EC 2.5.1.6), cysK encoding cysteine synthase (EC 2.5.1.47), cysI encoding a putative NADPH dependant sulfite reductase, and finally ssuD encoding an putative alkanesulfonate monooxygenase. Rey et al. (*Molecular Microbiology* 2005, 56, 871-887) also found that the metB gene is significantly induced in a mcbR minus strain.

As regards the cob(I)alamin-dependent methionine synthases which, for the purposes of the present invention, are also designated as cobalamin-dependent methionine synthases or MetH, it has been shown that activity of this enzyme is inhibited by its product, i.e. methionine (Banerjee et al. (1990), *Biochemistry,* 29:11101-1109).

This so-called "product inhibition" of methionine probably accounts for the high need of methionine production which has been calculated to require an energy input of 7 mol ATP and 8 mol NADPH per molecule methionine (Neidhardt et al. (1990) *Physiology of the Bacterial Cell: A Molecular Approach*, Sunderland, Mass., USA, Sinauer Associates, Inc.). Thus, methionine is the one amino acid with respect to which a cell has to provide the most energy.

As a consequence thereof, methionine-producing organisms have evolved metabolic pathways that are under strict control with respect to the rate and amount of methionine synthesis (Neidhardt (1996) *E. coli* and *S. typhimurium*, ASM Press Washington). These regulation mechanisms include e.g. feedback control mechanisms such as the above-mentioned product inhibition of the activity of the cobalamin-dependent methionine synthase.

The product inhibition of the cobalamin-dependent methionine synthase creates a particular bottleneck when producing methionine over-producing microorganisms, as this enzyme catalyses the last step in the methionine biosynthesis pathway. Thus, microorganisms which have been optimized with respect to expression of other enzymes involved in the methionine biosynthesis pathway may ultimately prove to be unusable for efficient methionine production, because even though e.g. elevated amounts of homocysteine have accumulated in these microorganisms, homocysteine cannot be efficiently methylated to methionine, as the cells will shut off this enzymatic step once enough methionine has been produced.

As can be taken from FIG. 1, the methylation of homocysteine to methionine is catalysed by two types of enzymes. The cobalamin-independent methionine synthase, which is also designated as MetE in view of its low turnover numbers has a rather limited catalytic capability (Gonzales et al. (1992) *Journal of Biology* 31:6045-6056). Cobalamin-dependent synthase, however, seems to be a rather good candidate for this approach given its turnover number of about 1500 $min^{-1}$ (Gonzales et al. (1992) vide supra).

One of the objectives of the present invention is to resolve the limitations for the non-chemical methionine production in organisms. This and other objectives which will be become apparent from the ensuing description are solved by the independent claims. Preferred embodiments are described in the dependent claims.

The core of the present invention lies at the surprising finding that it is possible to produce mutants of cobalamin-dependent methionine synthases in which the inhibition of the enzymatic activity by the product methionine is significantly reduced.

These mutants, which show reduced product inhibition, thus continue to efficiently catalyze the methylation of homocysteine into methionine in a cobalamin-dependent manner, even when methionine levels are reached for which a microorganism will usually down-regulate the enzymatic activity of this last step. As these mutants decouple the enzymatic activity of cobalamin-dependent methionine synthase from the feedback control mechanism of product inhibition, they allow the construction of host organisms that produce methionine continuously and efficiently.

While such enzymatically active cobalamin-dependent methionine synthase mutants have been specifically isolated for the MetH enzyme of *C. glutamicum*, it is justified to assume that corresponding mutants exist for cobalamin-dependent methionine synthases in other organisms such as *E. coli, S. coel* and *T. maritima*. This is supported by the fact that cobalamin-dependent methionine synthases from *E. coli, S. coel, C. glutamicum, Thermotoga maritima* show a high degree of sequence similarity particularly in the homocysteine-binding domain which is the region that has been identified by the present invention to be most suitable for introducing mutations that reduce the product inhibition of cobalamin-dependent methionine synthases in *C. glutamicum.*

Before specific and preferred cobalamin-dependent methionine synthase mutants are described in more detail, an overview is given for the properties of cobalamin-dependent methionine synthases in general.

Cobalamin-dependent methionine synthase catalyses the transfer of a methyl group from methyltetrahydrofolate to homocysteine generating tetrahydrofolate and methionine (Banerjee (1990) vide supra). The MetH gene from *E. coli* as well as from other organisms including *T. maritima, S. coel* and *C. glutamicum* have been cloned, and in some cases characterized (Banerjee (1990) vide supra; Ludwig et al. (1997) *Annu. Rev. Biochem.*, 66:269-313; Yamada et al. (1999) *Journal of Biological Chemistry,* 274:33571-33576; Evans et al. (2004) *Proc. Natl. Acad. Sci. USA,* 101:3729-3736).

The enzyme contains a non-covalently bound cobalamin prosthetic group that functions as an intermediary in the methyl-transferase reaction. During catalysis, the enzyme shuttles between the E-methyl cobalamin and E-cob(I)alamin states, being alternately demethylated by homocysteine and remethylated by methyltetrahydrofolate.

An assay to measure the activity of methionine synthase is described in the literature (Drummond et al. (1995) *Analytical Biochemistry,* 228:323-329). This latter reference is specifically incorporated by reference, as far as it describes assays for the characterization of cobalamin-dependent methionine synthases. Thus, the passages starting on page 324, right column ("Materials and Methods") to page 326, left column ("Results") of the Drummond et al. reference form part of the disclosure of this application as far as non-radioactive assays for characterization of cobalamin-dependent methionine synthases are concerned. The assay described by Drummond et al. can be used for determining the influence of the product methionine on the enzymatic activity of cobalamin-dependent methionine synthases along the same lines as described by the aforementioned reference of Banerjee et al. (1990) vide supra for radioactive assays on page 11102, left column ("Experimental procedures") to page 11103, left column ("Results") and page 11103, right column ("Product inhibition data") to page 11104, left column ("Pre-steady-state kinetic analysis of catalysis") and Table II of the Banerjee et al. reference. As can be taken from the latter reference cobalamin-dependent methionine synthases are inhibited by methionine in a non-competitive manner.

The cobalamin-dependent methionine synthase of *E. coli* which is representative for other cobalamin-dependent methionine synthases from organisms such as *C. glutamicum*, etc. is a modular protein consisting of various domains.

The first 352 residues of the *E. coli* enzyme comprise a homocysteine binding region. Residues 353 to 649 are involved in the binding of methyltetrahydrofolate, while residues 650 to 896 bind the cobalamin co-factor. The carboxy terminal residues 897 to 1227 are required for reactivation of oxidized cob(II)alamin and bind adenosylsylmethyl. A 71 kDa fragment, which comprises residues 2 to 649, contains the homocysteine and methyltetrahydrofolate binding domains and catalyses methyl transfer to and from exogenous cobalamin. The 98 kDa fragment comprises both the aforementioned substrate binding regions and the cobalamin binding domain and is capable of enzymatic turnover using endogenous cobalamin co-factor.

The present invention at its core relates to enzymatically active cobalamin-dependent methionine synthases or functional fragments thereof with reduced product inhibition by methionine.

As set out above, the present invention in one embodiment relates to enzymatically active cobalamin-dependent methionine synthases or functional fragments thereof which carry at least one mutation in comparison to the respective wild-type sequence with the mutation having the consequence that the mutated enzymatically active cobalamin-dependent methionine synthases or fragments thereof show reduced product inhibition by methionine.

The term "functional fragment" refers to fragments of wild-type full-length versions of enzymatically active cobalamin-dependent methionine synthases which are able to catalyse the methylation of homocysteine to methionine in a cobalamin-dependent manner and which additionally carry at least one mutation in their amino acid sequence which effects reduced product inhibition by methionine.

Cobalamin-dependent methionine synthases or functional fragments thereof in accordance with the invention are thus preferably considered to show reduced impaired product inhibition if the non-competitive inhibition of the methylation of homocysteine with methyltetrahydrofolate by the enzyme is influenced to a lesser extent by methionine than for the respective wild-type cobalamin-dependent methionine synthases or functional fragments thereof.

According to the present invention, an enzymatically active cobalamin-dependent methionine synthases or a functional fragments thereof are particularly considered to show reduced product inhibition by methionine if, as a consequence of the mutation in the amino acid sequence, the inhibition of the activity by methionine, and preferably by approximately 20 mM methionine is reduced by at least 10%, 20%, 30%, 40%, 50%, 60%, 70%, 80%, 90%, 100% and preferably by at least a factor of 3, 4, 5, 6, 7, 8, 9, 10, 15, 20, 50, 100, 200, 500, 1000 or more compared to the enzymatic activity of the respective wild type enzyme or functional fragment.

If the enzymatic activity of a wild-type cobalamin-dependent methionine synthase or a functional fragment thereof is defined as 100%, cobalamin-dependent methionine synthases or functional fragments thereof with reduced product inhibition by methionine in accordance with the invention show an increased activity in the presence of methionine, and preferably of approximately 20 mM methionine of at least 10%, 20%, 30%, 40%, 50%, 60%, 70%, 80%, 90%, 100% and preferably by at least a factor of 3, 4, 5, 6, 7, 8, 9, 10, 15, 20, 50, 100, 200, 500, 1000 or more compared to the enzymatic activity of the respective wild type enzyme or functional fragment.

The influence of methionine, and preferably of approximately 20 mM methionine on the activity of either wild-type enzymatically active cobalamin-dependent methionine synthases or functional fragments thereof and enzymatically active cobalamin-dependent methionine synthases in accordance with the present invention which have reduced product inhibition can be determined by the assay as described by Drummond et al. (vide supra).

By way of example, the cobalamin-dependent methionine synthase may be MetH of *C. glutamicum* and have an amino acid sequence of SEQ ID NO: 1. If a MetH version of SEQ ID NO: 1 which additionally carries at least one mutation shows a reduced influence of methionine, and preferably of approximately 20 mM methionine on the activity of this enzyme under the above test conditions, it will be considered as a cobalamin-dependent methionine synthase with reduced product inhibition in accordance with the present invention. The same would apply for a functional fragment of MetH.

Accordingly, cobalamin-dependent methionine synthases of other organisms such as *E. coli, T. maritima, B. subtilis, S. coel* which show a significant homology to the wild-type MetH enzyme of *C. glutamicum* and which additionally carry mutations that reduce the product inhibition of these enzymes in comparison to their respective wild-type enzymes under the above test conditions, will also be considered as cobalamin-dependent methionine synthases with a reduced product inhibition in accordance with the present invention.

According to the present invention, a significant sequence homology between two nucleic acid molecules or two polypeptides is generally understood to indicate that the nucleotide sequences or the amino acid sequences, respectively, of a e.g. DNA molecules or proteins are at least 30%, at least 40%, preferably at least 50%, at least 60%, at least 70%, also preferably at least 80%, particularly preferably at least 90%, at least 95%, at least 96%, at least 97%, at least 98% and most preferably at least 99% identical. Additionally, the term "significant sequence homology" can require that the e.g. 90% identical nucleotide sequences encode polypeptides with the same function, e.g. a cobalamin-dependent methionine synthase or functional fragment thereof.

Identity of two nucleotides sequences or polypeptides is understood to be the identity of the nucleotides or amino acids over the respective entire length of the nucleotide sequences or the polypeptides respectively. Identity and Homology can be calculated using the laser gene software from DNA Star, Inc., Madison, Wis. (USA) applying the CLUSTAL method (Higgens et al. (1989), *Comput. Appl. Biochi.,* 5(2):151). Homologies and identities for amino acid and nucleic acid sequences may also be calculated using algorithms which are based on algorithms by Niedelmann and Wunsch or Smith and Waterman. Software that may be used for these purposes are the programs Pil Aupa (J. Mol. Evolution (1987), 25, 351-360; Higgins et al. (1989) Cabgos, 5:151) or the programs Gap and Bestfit (Niedelmann und Wunsch (1970), J. Mol. Biol., 48, 443-453 and Smith and Waterman (1981) Adv. Appl. Math., 2, 482-489). For the purposes of determining the identity of two sequences, the default parameters of the above software programs are used.

An example of determining a significant sequence homolgy between cobalamin-dependent methionine synthases of different organisms is provided by the sequence alignment of FIG. 2.

In one embodiment of the present invention, the mutations that lead to reduced product inhibition of the enzymatically active cobalamin-dependent methionine synthases or functional fragments thereof are located in the homocysteine binding region of the proteins. For the *E. coli* cobalamin-dependent methionine synthase, this region has been mapped to amino acids 1 to 251.

It is well within the general knowledge of the person skilled in the art to identify corresponding domains in proteins that are related to the *E. coli* enzyme. In FIG. 2, a sequence alignment is shown for the cobalamin-dependent methionine synthases with wild-type sequences for *C. glutamicum, E. coli, S. coel* and *T. maritima*. From a comparison, it can be seen that amino acids 1 to 251 of the *E. coli* enzyme correspond to amino acids 1 to 244 of the *C. glutamicum* enzyme, amino acids 1 to 212 of the *T. maritima* enzyme and amino acids 1 to 243 of the *S. coel* enzyme.

Accordingly, one embodiment of the present invention relates to cobalamin-dependent methionine synthases which carry mutations in a sequence that is significantly homologous to SEQ ID NO: 1 and which provide reduced product inhibition. In other embodiments of the present invention, the cobalamin-dependent methionine synthases with reduced product inhibition in accordance with the present invention have at least one mutation in at least one of the following sequences:

SEQ ID NO 3:
$X_1X_2X_3X_4X_5X_6X_7LX_8X_9X_{10}$ wherein $X_1$=S, V, R; $X_2$=S, E, R; $X_3$=E, A, Q; $X_4$=F, L, V; $X_5$=L, R, S; $X_6$=D, E, A, K; $X_7$=A, Q, L; $X_8$=A, N, S; $X_9$=N, T, E; $X_{10}$=H, R

SEQ ID NO 4:

$X_1X_2X_3X_4DGX_5X_6GTX_7X_8X_9X_{10}X_{11}$ wherein $X_1$=V, I; $X_2$=V, L; $X_3$=I, V, L; $X_4$=g, A, L; $X_5$=A, G; $X_6$=M, Y; $X_7$=Q, M, E; $X_8$=L, I, F; $X_9$=Q, M; $X_{10}$=G, A, S, K; $X_{11}$=F, Q, Y

SEQ ID NO 5:

$X_1X_2X_3X_4X_5X_6X_7X_8X_9X_{10}X_{11}X_{12}X_{13}X_{14}X_{15}$ wherein $X_1$=L, P, Y; $X_2$=D, T, N; $X_3$=V, L, D, E; $X_4$=E, D, A, L; $X_5$=K, D, P; $X_6$=F except in *T. marina, C. glutamicum, S. coel.*; $X_7$=R except in *T. marina, C. glutamicum, S. coel.*; $X_8$=G except in *T. marina, C. glutamicum, S. coel.*; $X_9$=E except in *T. marina, C. glutamicum, S. coel.*; $X_{10}$=R except in *T. marina, C. glutamicum, S. coel.*; $X_{11}$=F except in *T. marina, C. glutamicum, S. coel.*; $X_{12}$=A except in *T. marina, C. glutamicum, S. coel.*; $X_{13}$=D except in *T. marina, C. glutamicum, S. coel.*; $X_{14}$=D, W except in *T. marina*; $X_{15}$=F, P except in *T. marina*

SEQ ID NO 6:
$LX_1X_2X_3X_4PX_5X_6X_7X_8X_9X_{10}HX_{11}X_{12}YX_{13}$ wherein $X_1$=N, V; $X_2$=D, L, I; $X_3$=T, S, K; $X_4$=R, K, A; $X_5$=D, E; $X_6$=V, I; $X_7$=L, V, I; $X_8$=R, A, L; $X_9$=Q, S, A, K; $X_{10}$=I, V; $X_{11}$=R, E, N; $X_{12}$=A, E, S; $X_{13}$=F, I;

SEQ ID NO 7:
$X_1X_2GX_3DX_4X_5X_6TNTFX_7X_8X_9$ wherein $X_1$=E, A; $X_2$=A, S; $X_3$=A, V, S; $X_4$=L, C, I, V; $X_5$=V, I; $X_6$=E, L; $X_7$=G, N; $X_8$=C, A, S; $X_9$=N, T;

SEQ ID NO 8:
$X_1X_2X_3X_4X_5X_5X_6X_7X_8X_9$ wherein $X_1$=L, H, T, R; $X_2$=P, S, I, M; $X_3$=N, A, K; $X_4$=L. M; $X_5$=A, G, R; $X_6$=D, E, K; $X_7$=Y, H; $X_8$=D, Q, G; $X_9$=I, M, L;

SEQ ID NO 9:
$X_1X_2X_3X_4X_5X_6X_7X_8X_9X_{10}X_{11}X_{12}X_{13}X_{14}ARX_{15}X_{16}AX_{17}EX_{18}$ wherein $X_1$=A, P, E; $X_2$=D, E, S; $X_3$=R, L, K; $X_4$=C, V, S, L; $X_5$=R, H, A, D; $X_6$=E, P; $X_7$=L, I; $X_8$=A, S, N, V; $X_9$=Y, E, f, R; $X_{10}$=K, A, N; $X_{11}$=G, A; $X_{12}$=T, A, V; $X_{13}$=A, R, K; $X_{14}$=V, L, I; $X_{15}$=E, A, R; $X_{16}$=V, C, A; $X_{17}$=D, E; $X_{18}$=F, M, W, K

SEQ ID NO 10:
$X_1X_2X_3X_4X_5X_6RX_7$ wherein $X_1$=G except in *T. marina*, A, R except in *T. marina*; $X_2$=R, T except in *T. marina*; $X_3$=N, D, P except in *T. marina*; $X_4$=G, G, E except in *T. marina*; $X_5$=M, R, K except in *T. marina*; $X_6$=R, Q, P except in *T. marina*; $X_7$=F, W, Y except in *T. marina*;

SEQ ID NO 11:
$VX_1GX_2X_3GPX_4X_5X_6X_7X_8X_9$ wherein $X_1$=V, L, A, F; $X_2$=S, V, D; $X_3$=L, M, I; $X_4$=G, T; $X_5$=T, N, G; $X_6$=K, R, E; $X_7$=L, T; $X_8$=P, A; $X_9$=S, T, Y;

SEQ ID NO 12:
$X_1X_2X_3X_4X_5X_6X_7X_8X_9X_{10}X_{11}X_{12}X_{13}X_{14}X_{15}X_{16}X_{17}X_{18}GX_{19}$ wherein $X_1$=F, Y; $X_2$=>, T, D, E; $X_3$=D, V, G, E; $X_4$=L, F; $X_5$=R, V, Y; $X_6$=G, D, A, E; $X_7$=H, A, N; $X_8$=Y, E; $X_9$=K, Q, R; $X_{10}$=E, R; $X_{11}$=A, N, S, T; $X_{12}$=A, T, V; $X_{13}$=L, E, K; $X_{14}$=G, A, I; $X_{15}$=I, L, M; $X_{16}$=I, V; $X_{17}$=E, A, E; $X_{18}$=G, E; $X_{19}$=G, A, V

SEQ ID NO 13:
$DX_1X_2X_3X_4ET$ wherein $X_1$=A, L, G; $X_2$=F, L, I; $X_3$=L, I; $X_4$=I, V, F

SEQ ID NO 14:
$X_1DX_2LX_3X_4KAX_5VX_6X_7X_8X_9$ wherein $X_1$=Q, F, S; $X_2$=L, T, I; $X_3$=Q, N, E; $X_4$=V, T, A, L; $X_5$=A, S; $X_6$=H, L, F; $X_7$=G, A; $X_8$=V, A; $X_9$=Q, R, K

SEQ ID NO 15:
$X_1X_2X_3X_4X_5X_6X_7X_8X_9X_{10}X_{11}T$ wherein $X_1$=L, V; $X_2$=D, G, S; $X_3$=T, L, V, R; $X_4$=F, D, E; $X_5$=L, V; $X_6$=P, F; $X_7$=I, L; $X_8$=I, M; $X_9$=C, V, I, A; $X_{10}$=H, S; $X_{11}$=V, G, M

SEQ ID NO 16:
$X_1X_2X_3X_4X_5X_6X_7X_8LX_9GX_{10}X_{11}$ wherein $X_1$=V, I, F; $X_2$=E, T, D; $X_3$=T, D, E; $X_4$=T, A, K; $X_5$=G, S; $X_6$=G except in *T. marina, C. glutamicum, S. coel.*; $X_7$=T, R; $X_8$=M, T, S; $X_9$=M, L, S, T; $X_{10}$=S, Q, T; $X_{11}$=E, T, D

SEQ ID NO 17:
$X_1X_2X_3X_4X_5X_6X_7$ wherein $X_1$=G, E, A; $X_2$=A, N; $X_3$=A, F; $X_4$=L, Y, A; $X_5$=T, N, I; $X_6$=A, S, T; $X_7$=L, F

SEQ ID NO 18:
$X_1X_2X_3X_4X_5X_6X_7GX_8NCX_9X_{10}GPX_{11}E$ wherein $X_1$=P, H, E; $X_2$=L, A; $X_3$=G, E, D; $X_4$=I, A; $X_5$=D, L; $X_6$=M, T, A; $X_7$=I, F, L; $X_8$=L, I; $X_9$=A, S; $X_{10}$=T, L; $X_{11}$=D, A, E In the context of the present invention the term "mutation" as regards an amino acid sequence relates to an amino acid substitution, insertion or deletion in the wild type sequence of cobalamin-dependent methionine synthases or functional fragments thereof with the requirement that the mutation changes the enzymatic activity such that the resulting polypeptide is still capable of catalyzing transfer of a methyl group from methyltetrahydrofolate to homocysteine in a cobalamin-dependent manner, with the mutated enzyme or functional fragment thereof having reduced product inhibition by methionine as defined above.

The person skilled in the art will be able to introduce mutations e.g. in the aforementioned amino acid sequences SEQ ID NOs: 1 to 18 and, e.g. relying on the assay described above, will be able to determine whether the resulting polypeptides are enzymatically active and show reduced product inhibition in the presence by methionine.

For such mutations, the person skilled in the art will consider in particular non-conservative amino acid substitutions, meaning that the wild-type amino acid is replaced with an amino acid of different physical-chemical properties. For example, if the wild-type sequence comprises a charged amino acid such as aspartate, a non-conservative substitution will include a substitution of the aspartate for a positively charged amino acid such as lysine. Alternatively, a negatively charged amino acid such as aspartic acid or glutamic acid may be replaced by a neutral amino acid such as glutamine, arginine or methionine. The person skilled in the art will, of course, also consider conservative amino acid substitutions, i.e. replacement by amino acids with comparable physico-chemical properties. An example is a replacement of Valine by Leucine.

An enzymatically active cobalamin-dependent methionine synthase or functional fragment thereof which carries a mutation in comparison to the respective wild type sequences is not considered to be polypeptide in accordance with the invention if it does not show a reduced product inhibition by methionine as it can be determined by the above mentioned test. Mutated polypeptides are also not considered to form part of the invention if they are not enzymatically active. This also applies for the nucleotide sequence encoding such polypeptides.

The nomenclature used throughout this specification for amino acids is the common one letter code.

As regards SEQ ID NOs: 3 to 18, "mutation" in the case of amino acid substitution means that the amino acid of a specified position can be replaced with any amino acid which is not specified for this particular position. For example, for SEQ ID NO: 3, $X_1$ is specified to be S, V or R. A mutation may therefore comprise any amino acid substitution which is not S, V, R. Similarly, residue $X_4$ of SEQ ID NO: 4, which is G, A, L, may be replaced by any amino acid which is not G, A, L.

The person skilled in the art is well aware that for any type of amino acid substitution, deletion or insertion, it will be necessary to determine whether the resulting polypeptide is (i) enzymatically active and (ii) shows a reduced product inhibition of the enzymatic activity in the presence of methionine.

The above explanations of the term "mutation" as given for amino acid sequences correspondingly apply for nucleotide and preferably DNA sequences encoding such polypeptides.

Specific embodiments of the present invention in case of the cobalamin-dependent methionine synthase MetH of *C. glutamicum* include mutations in positions 33, 86 and 134, wherein the wild-type sequence residues are methionine, phenylalanine and serine, respectively.

In the case of position 33, the methionine may be changed to glycine or alanine. In case of the phenylalanine 86 position, phenylalanine may be changed into leucine. In case of the serine residue at position 134, the residue may be changed into asparagine. The corresponding amino acid sequences are depicted in SEQ ID NOs: 19 to 22 respectively, while the corresponding DNA sequences are depicted in SEQ ID NOs: 25 to 28.

The person skilled in the art will realise that corresponding mutations may be introduced in e.g. the methionine residue 34 of the *S. coel* enzyme, the methionine residue 22 of the *E. coli* enzyme and the tyrosine residue in position 22 of the *Thermotoga* enzyme. As regards the phenylalanine 86 position of the *C. glutamicum* enzyme, corresponding mutations in the *E. coli* system would be located at the phenyl alanine residue 91, in the *S. coel* enzyme at the phenylalanine residue 86 and in the *Thermotoga maritimum* enzyme at the phenylalanine residue 76.

As regards the serine 134 residue in the *C. glutamicum* enzyme, corresponding mutations in the *S. coel* enzyme would be located at serine 134, in the *E. coli* enzyme at the valine residue 131 and in the *Thermotoga* enzyme at the aspartate residue 124.

In these cases, the corresponding residues may be mutated into glycine and alanine for the methione/tyrosine residues, into leucine for the phenylalanine residue and into asparagine for the serine, valine or aspartate residue.

Correspondingly, instead of amino acid substitution, cobalamin-dependent methionine synthases with reduced product inhibition in accordance with the present invention may have deletions at the aforementioned positions, or additional insertions.

Other embodiments of the present invention are nucleotide sequences and particularly DNA sequences which encode the aforementioned polypeptides and proteins. Some embodiments of the present invention relate to such DNA sequences in an isolated form.

Other embodiments of the present invention relate to vectors which comprise in 5'-3' direction:

a) a promoter sequence being functional for expression of nucleotide sequences in a host cell b) operatively linked thereto a nucleotide and preferably a DNA sequence in accordance with the present invention, and c) operatively linked thereto a termination sequence.

According to the present invention, operative linkage of a promoter, a nucleotide sequence in accordance with the present invention and a termination sequence means that nucleotide sequences in accordance with the present invention can be expressed in a host cell such that the host cell expresses an enzymatically active cobalamin-dependent methionine synthase or a functional fragment thereof that shows the reduced product inhibition by methionine as defined above.

In a preferred embodiment, these vectors comprise certain promoters and optionally enhancer elements to allow for over-expression of e.g. DNA sequences encoding the aforementioned polypeptides and proteins. Specific embodiments for expression and over-expression of DNA sequences are explained below.

Accordingly, another embodiment of the present invention relates to host cells which comprise nucleotide and preferably DNA sequences or vectors, as have been described above.

By genetically amending organisms in accordance with the present invention, the efficiency and/or yield and/or amount of methionine synthesis may be increased such that these methionine-overproducing organisms are characterized in that methionine is produced with an increased efficiency and/or increased yield and/or increased amount of preferably at least 10%, at least 20%, at least 30%, at least 40%, at least 50%, at least 60%, at least 65%, at least 70%, at least 75%, at least 80%, at least 90% or at least 100% compared to an initial organism that does not express the nucleotide sequences in accordance with the present invention.

Compared to such an initial host organism, the efficiency and/or yield and/or amount of methionine production in the methionine-producing host organism according to the present invention can increased preferably by at least by a factor of 2, 3, 4, 5, 6, 7, 8, 9, 10, 30, 50, 70, 100, 200, 500 or at least by a factor of 1000.

The host organism according to the present invention may be selected from the group consisting of coryneform bacteria, mycobacteria, streptomycetes, *Salmonella, Escherichia coli, Shigella, Bacillus, Serratia, Pseudomonas, S. coel* or *T. maritima.*

The organisms of the present invention may preferably comprise a microorganism of the genus *Corynebacterium*, particularly *Corynebacterium acetoacidophilum, C. acetoglutamicum, C. acetophilum, C. ammoniagenes, C. glutamicum, C. lilium, C. nitrilophilus* or *C. spec.*

The organisms in accordance with the present invention also comprise members of the genus *Brevibacterium*, such as *Brevibacterium harmoniagenes, Brevibacterium botanicum, B. divaraticum, B. flavam, B. healil, B. ketoglutamicum, B. ketosoreductum, B. lactofermentum, B. linens, B. paraphinolyticum* and *B. spec.*

The organisms in accordance with the present invention also comprise *S. coel.*

The organisms in accordance with the present invention also comprise members of the genus *Thermotoga*, such as *T. maritime.*

In particular, *Corynebacterium* microorganisms may be selected from the group consisting of *Corynebacterium glutamicum* (ATCC 13032), *Corynebacterium acetoglutamicum* (ATCC 15806), *Corynebacterium acetoacidophilum* (ATCC 13870), *Corynebacterium thermoaminogenes* (FERM BP-1539), *Corynebacterium melassecola* (ATCC 17965), *Corynebacterium glutamicum* (KFCC 10065), *Corynebacterium glutamicum* (DSM 17322), *Corynebacterium efficiens* (YS 314) and *Corynebacterium glutamicum* (ATCC21608).

Particularly preferred is the strain *Corynebacterium glutamicum* ATCC13032 and all its derivatives. The strains ATCC 13286, ATCC 13287, ATCC 21086, ATCC 21127, ATCC 21128, ATCC 21129, ATCC 21253, ATCC 21299, ATCC 21300, ATCC 21474, ATCC 21475, ATCC 21488, ATCC 21492, ATCC 21513, ATCC 21514, ATCC 21515, ATCC 21516, ATCC 21517, ATCC 21518, ATCC 21528, ATCC 21543, ATCC 21544, ATCC 21649, ATCC 21650, ATCC 21792, ATCC 21793, ATCC 21798, ATCC 21799, ATCC 21800, ATCC 21801, ATCC 700239, ATCC 21529, ATCC 21527, ATCC 31269 and ATCC 21526 which are known to produce lysine can also preferably be used. The other aforementioned strains can also be used.

The abbreviation KFCC means Korean Federation of Culture Collection, while the abbreviation ATCC means the American Type Strain Culture Collection Collection. The abbreviation DSM means the German Resource Centre for Biological Material.

Microorganisms of the genus *Escherichia* may be selected from the group comprising *Escherichia coli*. Microorganisms of the genus *Salmonella* may be selected from the group comprising *Salmonella typhimurium.*

Such host organisms may be engineered by introducing exogenous nucleotide sequences in accordance with the present invention, e.g. in the form of vectors.

In addition, or alternatively, mutations such as those described above which effect a reduced product inhibition may be introduced into the endogenous coding sequences for cobalamin-dependent methionine synthases.

A further embodiment of the present invention relates to host cells in which nucleotide and preferably DNA sequences in accordance with the present invention which encode for enzymatically active cobalamin-dependent methionine synthases or functional fragments thereof having a reduced product inhibition in the presence of methionine are expressed and in which additionally the endogenous gene(s) for cobalamin-dependent methionine synthase(s) is/are deleted or functionally disrupted.

The term "deleted" or "functional disruption" are, for the purposes of the present invention, equivalent to the statement that the content and/or activity of the cobalamin-dependent methionine synthases as they are encoded by the endogenous genes of the host organism are reduced.

How a reduction of the content and/or the activity and correspondingly a deletion and/or functional disruption of these endogenous genes for cobalamin-dependent methionine synthases may be achieved is described below.

Other embodiments of the present invention relate to host cells in which DNA sequences in accordance with the present invention, i.e. encoding cobalamin-dependent methionine synthases or fragments thereof with a reduced product inhibition in the presence of methionine are expressed and in which the content and/or activity of at least one of the following nucleotide sequences of group I is increased in comparison to the respective initial organism:

nucleotide sequence coding for aspartate kinase lysC (EP 1 108 790 A2;

DNA SEQ ID NO: 281), nucleotide sequence coding for aspartate semialdehyde dehydrogenase asd (EP 1 108 790 A2; DNA SEQ ID NO: 282), nucleotide sequence coding for glycerine aldehyde-3-phosphat dehydrogenase gap (Eikmanns (1992), *Journal of Bacteriology,* 174: 6076-6086), nucleotide sequence coding for 3-phosphoglycerate kinase pgk (Eikmanns (1992), *Journal of Bacteriology,* 174: 6076-6086), nucleotide sequence coding for pyruvate carboxylase pyc (Eikmanns (1992), *Journal of Bacteriology,* 174: 6076-6086), nucleotide sequence coding for triosephosphate isomerase tpi (Eikmanns (1992), *Journal of Bacteriology,* 174: 6076-6086), nucleotide sequence coding for homoserine-O-acetyl transferase metA (EP 1 108 790; DNA SEQ ID NO: 725), nucleotide sequence coding for cystahionine gamma synthase metB (EP 1 108 790; DNA SEQ ID NO: 3491), nucleotide sequence coding for cystahionine gamma lyase metC (EP 1 108 790; DNA SEQ ID NO: 3061), nucleotide sequence coding for serine hydroxymethyl transferase glyA (EP 1 108 790; DNA SEQ ID NO: 1110), nucleotide sequence coding for O-acetylhomoserine sulfhydrylase metY (EP 1 108 790; DNA SEQ ID NO: 726), nucleotide sequence coding for methylenetetrahydrofolate reductase metF (EP 1 108 790; DNA SEQ ID NO: 2379), nucleotide sequence coding for phosphoserine amino transferase serC (EP 1 108 790; DNA SEQ ID NO: 928), nucleotide sequence coding for phosphoserine phosphatase serB (EP 1 108 790; DNA SEQ ID NO: 334, DNA SEQ ID NO: 467, DNA SEQ ID NO: 2767), nucleotide sequence coding for serine acetyl transferase cyse (EP 1 108 790; DNA SEQ ID NO: 2818), nucleotide sequence coding for homoserine dehydrogenase hom (EP 1 108 790; DNA SEQ ID NO: 1306), nucleotide sequence coding for methionine synthase mete (gene bank accession number NCgl1094), nucleotide sequence coding for cysteine synthase (gene bank accession number NP_601760, NP_601337, NCg12473, NCgl2055), nucleotide sequence coding for sulfite reductase (gene bank accession numbers NP_602008, NCgl2718)

nucleotide sequence coding for phosphoadenosine phosphosulfate reductase (gene bank accession number NP_602007, NCgl2717), nucleotide sequence coding for sulfate adenylyl transferase subunit 1 (gene bank accession number NP_602005, NCgl2715), nucleotide sequence coding for CysN-sulfate adenylyl transferase subunit 2 (gene bank accession number NP_602006, NCgl2716), nucleotide sequence coding for ferredoxin NADP reductase (gene bank accession number NP_602009, NCgl2719), nucleotide sequence coding for ferredoxine (gene bank accession number NP_602010, NCgl2720), nucleotide sequence coding for glucose-6-phosphate dehydrogenase (gene bank accession number NP_600790, NCgl1514), and/or nucleotide sequence coding for fructose-1-6-bisphosphatase (gene bank accession number NP_601294, NCgl2014).

Of course, such host organisms may show an increased content and/or activity of nucleotide sequences which show a significant homology as defined above for any of the aforementioned nucleotide sequences. Again, the term "significant sequence homology" requires that these nucleotide sequences encode polypeptides that have the respective enzymatic activity.

In other embodiments of the present invention, the host organism may comprise nucleotide and preferably DNA sequences in accordance with the invention which encode cobalamin-dependent methionine synthases or active fragments thereof with reduced product inhibition in the presence of methionine and additionally provides a reduced content and/or activity of at least one of the following nucleotide sequences of group II:

nucleotide sequence coding for homoserine kinase thrB (EP 1 108 790; DNA SEQ ID NO: 3453), nucleotide sequence coding for threonine dehydratase ilvA (EP 1 108 790; DNA SEQ ID NO: 2328), nucleotide sequence coding for threonin synthase thrC (EP 108 790; DNA SEQ ID NO: 3486), nucleotide sequence coding for meso diaminopimelat-D-dehydrogenase ddh (EP 1 108 790; DNA SEQ ID NO: 3494), nucleotide sequence coding for phosphoenol pyruvate carboxykinase pck (EP 1 108 790; DNA SEQ ID NO: 3157), nucleotide sequence coding for glucose-6-phosphatr-6-isomerase pgi (EP 1 108 790; DNA SEQ ID NO: 950), nucleotide sequence coding for pyruvate oxidase poxB (EP 1 108 790; DNA SEQ ID NO: 2873), nucleotide sequence coding for dihydrodipicolinate synthase dapA (EP 1 108 790; DNA SEQ ID NO: 3476), nucleotide sequence coding for dihydrodipicolinate reductase dapB (EP 1 108 790; DNA SEQ ID NO: 3477), nucleotide sequence coding for diaminopicolinate-decarboxylase lysA (EP 1 108 790 A2; DNA SEQ ID NO: 3451), nucleotide sequence coding for glycosyl transferase (gene bank accession numbers NP_600345 and NCgl1072) and/or nucleotide sequence coding for lactate dehydrogenase (gene bank accession number NP_602107, NCgl2817).

The increase and/or decrease in the content and/or activity of the aforementioned nucleotide sequences of group I and II in comparison to the respective wild-type or initial organism may amount to at least 10%, at least 20%, at least 30%, at least 40%, at least 50%, at least 60%, at least 65%, at least 70%, at least 75%, at least 80%, at least 90% or at least 100%. Compared to such initial host organisms, the increase and/or decrease in the content and/or activity of the aforementioned nucleotide sequences of group I and II according to the present invention can amount also preferably to at least at factor of 2, 3, 4, 5, 6, 7, 8, 9, 10, 30, 50, 70, 100, 200, 500 or at least a factor of 1000.

Thus, all host cells and organisms in accordance with the present invention are characterized in that they comprise and preferably over-express at least one nucleotide and preferably DNA sequence in accordance with the present invention which encodes a protein or polypeptide that is an enzymatically active cobalamin-dependent methionine synthase or functional fragment thereof showing a reduced product inhibition in the presence of methionine as defined above. These polypeptides or proteins will usually carry at least one mutation in their amino acid sequence in comparison with the respective wild-type amino acid sequence which is responsible for the reduced product inhibition by methionine. In addition, these host cells may show an increase and/or decrease in the content and/or activity of any of the nucleotide sequences as specified above for group I and group II.

Alternatively, or in addition, these host cells may show a deletion or functional disruption of the endogenous genes encoding for wild-type cobalamin-dependent methionine synthases. Such host cells may be selected from the organisms specified above and produced in accordance with the methods described below.

Other embodiments of the present invention relate to methods for producing methionine in a host cell, wherein at least one nucleotide and preferably DNA sequence in accordance with the present invention, i.e. a sequence that encodes a polypeptide or protein which is an enzymatically active cobalamin-dependent methionine synthase or functional fragment thereof with reduced product inhibition in the presence of methionine as a consequence of a mutation in the amino acid sequence, is expressed in a host organism. Such host cells may be cultivated under appropriate conditions and the produced methionine be recovered. Such methods may also provide an increased efficiency and/or yield of methionine in comparison to the respective starting organism.

Other embodiments of the present invention relate to the use of nucleotide and preferably DNA sequences in accordance with the present invention and host cells in accordance with the present invention for producing methionine and/or increasing the efficiency and/or yield of methionine production.

With respect to increasing or decreasing the amount and/or activity of nucleotide sequences and the polypeptides being encoded thereby, all methods that are known in the art for increasing or decreasing the amount and/or activity of nucleotide sequence and/or a polypeptide in a host such as the above-mentioned organisms may be used. These methods are described in further detail below. These methods may also be used to express a DNA sequence in accordance with the present invention, i.e. a DNA sequence encoding a cobalamin-dependent methionine synthase with reduced product inhibition in the presence of methionine as a consequence of a mutation in the amino acid sequence.

Increasing or Introducing the Amount and/or Activity of Nucleotide Sequences and/or Polypeptides in Accordance with the Invention and of Group I With respect to increasing the amount, two basic scenarios can be differentiated. In the first scenario, the amount of the polypeptide is increased by expression of an exogenous version of the respective nucleotide sequence. In the other scenario, expression of the endogenous polypeptide is increased by influencing the activity of promoter and/or enhancer elements and/or other regulatory activities such as phosphorylation, sumoylation, ubiquitylation, etc. that regulate the activities of the respective polypeptides either on a transcriptional, translational or post-translational level.

Besides simply increasing the amount of e.g. nucleotide sequences mentioned above, the activity of the polypeptides of e.g. group I may be increased by using enzymes carrying specific mutations that allow for an increased activity of the enzyme. Such mutations may, e.g. inactivate the regions of an enzyme that are responsible for feedback inhibition. By mutating these by e.g. introducing non-conservative mutations, the enzyme would not provide for feedback regulation anymore and thus activity of the enzyme would not be down regulated if more product was produced. The mutations may be either introduced into the endogenous copy of the enzyme, or may be provided by over-expressing a corresponding mutant form of the exogenous enzyme. Such mutations may comprise point mutations, deletions or insertions. Point mutations may be conservative or non-conservative. Furthermore, deletions may comprise only two or three amino acids up to complete domains of the respective protein. Of course, polypeptides in accordance with the invention, i.e. cobalamin-dependent methionine synthases or functional fragments thereof with reduced product inhibition can be expressed by expression of corresponding exogenous nucleotide sequences or by introducing the mutation(s) that leads to the reduced product inhibition in the endogenous genes.

Thus, the increase of the activity and the amount of a polypeptide may be achieved via different routes, e.g. by switching off inhibitory regulatory mechanisms at the transcription, translation, and protein level or by increase of gene expression of a nucleic acid coding for these proteins in comparison with the starting organism, e.g. by manipulating the endogenous gene or by introducing nucleic acids coding for the polypeptide.

In one embodiment, the increase of the activity and amount of a polypeptide, respectively, in comparison with the initial organism is achieved by an increase in the expression of a nucleic acid encoding such polypeptides. Sequences may be obtained from the respective database, e.g. at NCBI (HyperTextTransferProtocol://WorldWideWeb.ncbi.nlm.nihDOTgov/), EMBL (HyperTextTransferProtocol://WorldWideWeb.emblDOTorg), or Expasy (HyperTextTransferProtocol://WorldWideWeb.expasyDOTorg/), wherein "HyperTextTransferProtocol"="http", "WorldWideWeb"="www", and "DOT"=".".

In a further embodiment, the increase of the amount and/or activity of the above mentioned polypeptides is achieved by introducing the corresponding nucleic acids into the organism, preferably *C. glutamicum, E. coli, S. coel* or *T. maritima.*

In principle, every protein of different organisms with an enzymatic activity of the polypeptides mentioned above can be used. With genomic nucleic acid sequences of such enzymes from eukaryotic sources containing introns, already processed nucleic acid sequences like the corresponding cDNAs are to be used in the case that the host organism is not capable or cannot be made capable of splicing the corresponding mRNAs. All nucleic acids mentioned in the description can be, e.g., an RNA, DNA or cDNA sequence.

In one method according to the present invention for producing methionine, a nucleic acid sequence coding for one of the above-defined cobalamin-dependent methionine synthases or functional fragments thereof with reduced product inhibition by methionine is transferred to a microorganism such as *C. glutamicum, E. coli, S. coel* or *T. maritima*, respectively. This transfer leads to an increase in the expression of the mutated enzyme, and correspondingly to increased methionine synthesis.

According to the present invention, increasing and/or introducing the amount and/or the activity of a polypeptide typically comprises the following steps:

a) production of a vector comprising the following nucleic acid sequences, preferably DNA sequences, in 5'-3'-orientation:

- a promoter sequence functional in the organisms of the invention
- operatively linked thereto a DNA sequence in accordance with the invention
- a termination sequence functional in the organisms of the invention b) transfer of the vector from step a) to the organisms of the invention such as *C. glutamicum, E. coli, S. coel* or *T. maritima* and, optionally, integration into the respective genomes.

The use of such vectors comprising regulatory sequences, like promoter and termination sequences are, is known to the person skilled in the art. Furthermore, the person skilled in the art knows how a vector from step a) can be transferred to organisms such as *C. glutamicum, E. coli, S. coel* or *T. maritima* and which properties a vector must have to be able to be integrated into their genomes.

If the enzyme content in an organism such as *C. glutamicum* is increased by transferring a nucleic acid coding for a polypeptide from another organism, like e.g. *E. coli*, it is advisable to transfer the amino acid sequence encoded by the nucleic acid sequence e.g. from *E. coli* by back-translation of the polypeptide sequence according to the genetic code into a nucleic acid sequence comprising mainly those codons, which are used more often due to the organism-specific codon usage. The codon usage can be determined by means of computer evaluations of other known genes of the relevant organisms.

According to the present invention, an increase of the gene expression and of the activity, respectively, of a nucleotide sequence in accordance with the present invention is also understood to be the manipulation of the expression of the endogenous respective endogenous enzymes of an organism, in particular of *C. glutamicum, E. coli, S. coel* or *T. martima*. This can be achieved, e.g., by altering the promoter DNA sequence for genes encoding, e.g. cobalamin-dependent methionine synthases with reduced product inhibition. Such an alteration, which causes an altered, preferably increased, expression rate of these mutated enzymes can be achieved by deletion or insertion of DNA sequences. Of course, this requires that mutations which are responsible for the reduced product inhibition have been introduced into the endogenous genes.

An alteration of the promoter sequence of such mutated endogenous genes usually causes an alteration of the expressed amount of the gene and therefore also an alteration of the activity detectable in the cell or in the organism.

Furthermore, an altered and increased expression, respectively, of an endogenous gene can be achieved by a regulatory protein, which does not occur in the transformed organism, and which interacts with the promoter of these genes. Such a regulator can be a chimeric protein consisting of a DNA binding domain and a transcription activator domain, as e.g. described in WO 96/06166.

A further possibility for increasing the activity and the content of endogenous genes is to up-regulate transcription factors involved in the transcription of the endogenous genes, e.g. by means of overexpression. The measures for overexpression of transcription factors are known to the person skilled in the art.

Furthermore, an alteration of the activity of endogenous genes can be achieved by targeted mutagenesis of the endogenous gene copies.

An alteration of endogenous genes coding for the enzymes of e.g. group I can also be achieved by influencing the post-translational modifications of the enzymes. This can happen e.g. by regulating the activity of enzymes like kinases or phosphatases involved in the post-translational modification of the enzymes by means of corresponding measures like overexpression or gene silencing.

In another embodiment, polypeptides of e.g. group I may be improved in efficiency, or its allosteric control region destroyed such that feedback inhibition of production of the compound is prevented. Similarly, a degradative enzyme may be deleted or modified by substitution, deletion, or addition such that its degradative activity is lessened for the desired polypeptides or the polypeptides being encoded by the nucleotide sequences of the present invention without impairing the viability of the cell. In each case, the overall yield or rate of production of methionine may be increased.

It is also possible that such alterations in the polypeptides and nucleotide molecules may improve the production of other fine chemicals such as other sulfur containing compounds like cysteine or glutathione, other amino acids, vitamins, cofactors, nutraceuticals, nucleotides, nucleosides, and trehalose. Metabolism of any one compound can be intertwined with other biosynthetic and degradative pathways within the cell, and necessary cofactors, intermediates, or substrates in one pathway are likely supplied or limited by another such pathway. Therefore, by modulating the activity of polypeptides of the present invention and/or those of e.g. group I, the production and/or efficiency of another fine chemical biosynthetic or degradative pathway besides those leading to methionine may be impacted.

Enzyme expression and function may also be regulated based on the cellular levels of a compound from a different metabolic process, and the cellular levels of molecules necessary for basic growth, such as amino acids and nucleotides, may critically affect the viability of the microorganism in large-scale culture. Thus, modulation of an amino acid biosynthesis enzyme of e.g. the lysine biosynthetic pathways such that they are no longer responsive to feedback inhibition or such that they are improved in efficiency or turnover may result in better methionine production. The aforementioned strategies for increasing or introducing the amount and/or activity of the polypeptide and nucleotide sequences are not meant to be limiting; variations on these strategies will be readily apparent to one of ordinary skill in the art.

Reducing the Amount and/or Activity of Nucleotides Sequences and/or Polypeptides Encoding Endogenous Cobalamin Dependent Methionine Synthases and of Group II For reducing the amount and/or activity of nucleotide sequence and polypeptides being encoded thereby, various strategies are also available.

The expression of the endogenous enzymes of e.g. group II can e.g. be regulated via the expression of aptamers specifically binding to the promoter sequences of the genes. Depending on the aptamers binding to stimulating or repressing promoter regions, the amount and thus, in this case, the activity of such enzymes is increased or reduced.

Aptamers can also be designed in a way as to specifically bind to the enzymes themselves and to reduce the activity of the enzymes by e.g. binding to the catalytic center of the respective enzymes. The expression of aptamers is usually achieved by vector-based overexpression (see above) and is, as well as the design and the selection of aptamers, well known to the person skilled in the art (Famulok et al., (1999) *Curr Top Microbiol Immunol.,* 243, 123-36).

Furthermore, a decrease of the amount and the activity of e.g. the endogenous genes of MetH or of the endogenous enzymes of Group II can be achieved by means of various experimental measures, which are well known to the person skilled in the art. These measures are usually summarized under the term "gene silencing". For example, the expression of an endogenous gene can be silenced by transferring an above-mentioned vector, which has a DNA sequence coding for the enzyme or parts thereof in antisense order, to the organisms such as *C. glutamicum* and *E. coli*. This is based on the fact that the transcription of such a vector in the cell leads to an RNA, which can hybridize with the mRNA transcribed by the endogenous gene and therefore prevents its translation.

Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Trends in Genetics*, Vol. 1 (1) 1986.

In principle, the antisense strategy can be coupled with a ribozyme method. Ribozymes are catalytically active RNA sequences, which, if coupled to the antisense sequences, cleave the target sequences catalytically (Tanner et al., (1999) *FEMS Microbiol Rev.* 23 (3), 257-75). This can enhance the efficiency of an antisense strategy.

Further methods are the introduction of nonsense mutations into the endogenous gene by means of introducing RNA/DNA oligonucleotides into the organism (Zhu et al., (2000) *Nat. Biotechnol.* 18 (5), 555-558) or generating knockout mutants with the aid of homologous recombination (Hohn et al., (1999) *Proc. Natl. Acad. Sci. USA.* 96, 8321-8323.).

To create a homologous recombinant microorganism, a vector is prepared which contains at least a portion of gene coding for e.g. an enzyme of group II or the endogenous MetH gene into which a deletion, addition or substitution has been introduced to thereby alter, e.g., functionally disrupt, the endogenous gene.

Preferably, this endogenous gene is a *C. glutamicum* or *E. coli* gene, but it can be a homologue from a related bacterium or even from a yeast or plant source. In one embodiment, the vector is designed such that, upon homologous recombination, the endogenous gene is functionally disrupted (i. e. no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous enzyme of e.g. group 2). In the homologous recombination vector, the altered portion of the endogenous gene is flanked at its 5' and 3' ends by additional nucleic acid of the endogenous gene to allow for homologous recombination to occur between the exogenous gene carried by the vector and an endogenous gene in the (micro)organism. The additional flanking endogenous nucleic acid is of sufficient length for successful homologous recombination with the endogenous gene. Typically, several kilobases of flanking DNA (both at the 5' and 3'ends) are included in the vector (see e.g., Thomas, K. R., and Capecchi, M. R. (1987) *Cell* 51: 503 for a description of homologous recombination vectors).

The vector is introduced into a microorganism (e.g., by electroporation) and cells in which the introduced endogenous gene has homologously recombined with the endogenous enzymes are selected, using art-known techniques.

In another embodiment, an endogenous gene in a host cell is disrupted (e.g., by homologous recombination or other genetic means known in the art) such that expression of its protein product does not occur. In another embodiment, an endogenous or introduced gene in a host cell has been altered by one or more point mutations, deletions, or inversions, but still encodes a functional enzyme. In still another embodiment, one or more of the regulatory regions (e.g., a promoter, repressor, or inducer) of an endogenous gene in a (micro) organism has been altered (e.g., by deletion, truncation, inversion, or point mutation) such that the expression of the endogenous gene is modulated. One of ordinary skill in the art will appreciate that host cells containing more than one of the genes coding e.g. for the enzymes of group II and protein modifications may be readily produced using the methods of the invention, and are meant to be included in the present invention.

Furthermore, a gene repression (but also gene overexpression) is also possible by means of specific DNA-binding factors, e.g. factors of the zinc finger transcription factor type. Furthermore, factors inhibiting the target protein itself can be introduced into a cell. The protein-binding factors may e.g. be the above-mentioned aptamers (Famulok et al., (1999) *Curr Top Microbiol Immunol.* 243, 123-36).

As further protein-binding factors, whose expression in organisms cause a reduction of the amount and/or the activity of the enzymes of e.g. group II, enzyme-specific antibodies may be considered. The production of monoclonal, polyclonal, or recombinant enzyme-specific antibodies follows standard protocols (Guide to Protein Purification, Meth. Enzymol. 182, pp. 663-679 (1990), M. P. Deutscher, ed.). The expression of antibodies is also known from the literature (Fiedler et al., (1997) *Immunotechnology* 3, 205-216; Maynard and Georgiou (2000) *Annu. Rev. Biomed*. Eng. 2, 339-76).

The mentioned techniques are well known to the person skilled in the art. Therefore, he also knows which sizes the nucleic acid constructs used for e.g. antisense methods must have and which complementarity, homology or identity, the respective nucleic acid sequences must have. The terms complementarity, homology, and identity are known to the person skilled in the art.

The term complementarity describes the capability of a nucleic acid molecule of hybridizing with another nucleic acid molecule due to hydrogen bonds between two complementary bases. The person skilled in the art knows that two nucleic acid molecules do not have to have a complementarity of 100% in order to be able to hybridize with each other. A nucleic acid sequence, which is to hybridize with another nucleic acid sequence, is preferred being at least 30%, at least 40%, at least 50%, at least 60%, preferably at least 70%, particularly preferred at least 80%, also particularly preferred at least 90%, in particular preferred at least 95% and most preferably at least 98 or 100%, respectively, complementary with said other nucleic acid sequence.

Nucleic acid molecules are identical, if they have identical nucleotides in identical 5'-3'-order.

The hybridization of an antisense sequence with an endogenous mRNA sequence typically occurs in vivo under cellular conditions or in vitro. According to the present invention, hybridization is carried out in vivo or in vitro under conditions that are stringent enough to ensure a specific hybridization.

Stringent in vitro hybridization conditions are known to the person skilled in the art and can be taken from the literature (see e.g. Sambrook et al., Molecular Cloning, Cold Spring Harbor Press). The term "specific hybridization" refers to the case wherein a molecule preferentially binds to a certain nucleic acid sequence under stringent conditions, if this nucleic acid sequence is part of a complex mixture of e.g. DNA or RNA molecules.

The term "stringent conditions" therefore refers to conditions, under which a nucleic acid sequence preferentially binds to a target sequence, but not, or at least to a significantly reduced extent, to other sequences.

Stringent conditions are dependent on the circumstances. Longer sequences specifically hybridize at higher temperatures. In general, stringent conditions are chosen in such a way that the hybridization temperature lies about 5° C. below the melting point (Tm) of the specific sequence with a defined ionic strength and a defined pH value. Tm is the temperature (with a defined pH value, a defined ionic strength and a defined nucleic acid concentration), at which 50% of the molecules, which are complementary to a target sequence, hybridize with said target sequence. Typically, stringent conditions comprise salt concentrations between 0.01 and 1.0 M sodium ions (or ions of another salt) and a pH value between 7.0 and 8.3. The temperature is at least 30° C. for short molecules (e.g. for such molecules comprising between 10 and 50 nucleotides). In addition, stringent conditions can comprise the addition of destabilizing agents like e.g. form amide. Typical hybridization and washing buffers are of the following composition.

| | |
|---|---|
| Pre-hybridization solution: | 0.5% SDS |
| | 5x SSC |
| | 50 mM $NaPO_4$, pH 6.8 |
| | 0.1% Na-pyrophosphate |
| | 5x Denhardt's reagent |
| | 100 µg/salmon sperm |
| Hybridization solution: | Pre-hybridization solution |
| | 1 × $10^6$ cpm/ml probe (5-10 min 95° C.) |
| 20x SSC: | 3 M NaCl |
| | 0.3 M sodium citrate |
| | ad pH 7 with HCl |

-continued

| | |
|---|---|
| 50x Denhardt's reagent: | 5 g Ficoll |
| | 5 g polyvinylpyrrolidone |
| | 5 g Bovine Serum Albumin |
| | ad 500 ml A. dest. |

A typical procedure for the hybridization is as follows:

| | | | |
|---|---|---|---|
| Optional: | wash Blot 30 min in 1x SSC/0.1% SDS at 65° C. | | |
| Pre-hybridization: | at least 2 h at 50-55° C. | | |
| Hybridization: | over night at 55-60° C. | | |
| Washing: | 05 min | 2x SSC/0.1% SDS | |
| | Hybridization temperature | | |
| | 30 min | 2x SSC/0.1% SDS | |
| | Hybridization temperature | | |
| | 30 min | 1x SSC/0.1% SDS | |
| | Hybridization temperature | | |
| | 45 min | 0.2x SSC/0.1% SDS | 65° C. |
| | 5 min | 0.1x SSC | room temperature |

These stringent conditions also apply as far as the claims relate to DNA sequences that hybridise under stringent conditions.

The terms "sense" and "antisense" as well as "antisense orientation" are known to the person skilled in the art. Furthermore, the person skilled in the art knows, how long nucleic acid molecules, which are to be used for antisense methods, must be and which homology or complementarity they must have concerning their target sequences.

Accordingly, the person skilled in the art also knows, how long nucleic acid molecules, which are used for gene silencing methods, must be. For antisense purposes complementarity over sequence lengths of 100 nucleotides, 80 nucleotides, 60 nucleotides, 40 nucleotides and 20 nucleotides may suffice. Longer nucleotide lengths will certainly also suffice. A combined application of the above-mentioned methods is also conceivable.

If, according to the present invention, DNA sequences are used, which are operatively linked in 5'-3'-orientation to a promoter active in the organism, vectors can, in general, be constructed, which, after the transfer to the organism's cells, allow the overexpression of the coding sequence or cause the suppression or competition and blockage of endogenous nucleic acid sequences and the proteins expressed there from, respectively.

The activity of a particular enzyme may also be reduced by over-expressing a non-functional mutant thereof in the organism. Thus, a non-functional mutant which is not able to catalyze the reaction in question, but that is able to bind e.g. the substrate or co-factor, can, by way of over-expression outcompete the endogenous enzyme and therefore inhibit the reaction. Further methods in order to reduce the amount and/ or activity of an enzyme in a host cell are well known to the person skilled in the art.

Vectors and Host Cells

Another aspect of the invention pertains to vectors, preferably expression vectors, containing a nucleotide sequence in accordance with the invention (or portions thereof) or combinations thereof. As used herein, the term "vector" refers to a nucleic acid molecule capable of transporting another nucleic acid to which it has been linked.

One type of vector is a "plasmid", which refers to a circular double stranded DNA loop into which additional DNA segments can be ligated. Another type of vector is a viral vector, wherein additional DNA segments can be ligated into the viral genome.

Certain vectors are capable of autonomous replication in a host cell into which they are introduced (e.g., bacterial vectors having a bacterial origin of replication and episomal mammalian vectors). Other vectors are integrated into the genome of a host cell upon introduction into the host cell, and thereby are replicated along with the host genome. Moreover, certain vectors are capable of directing the expression of genes to which they are operatively linked.

Such vectors are referred to herein as "expression vectors".

In general, expression vectors of utility in recombinant DNA techniques are often in the form of plasmids. In the present specification, "plasmid" and "vector" can be used interchangeably as the plasmid is the most commonly used form of vector.

The recombinant expression vectors of the invention may comprise a nucleic acid in accordance with the present invention and/or coding for the enzymes of group I in a form suitable for expression of the respective nucleic acid in a host cell, which means that the recombinant expression vectors include one or more regulatory sequences, selected on the basis of the host cells to be used for expression, which is operatively linked to the nucleic acid sequence to be expressed.

Within a recombinant expression vector, "operably linked" is intended to mean that the nucleotide sequence of interest is linked to the regulatory sequence (s) in a manner which allows for expression of the nucleotide sequence (e.g., in an in vitro transcription/translation system or in a host cell when the vector is introduced into the host cell). The term "regulatory sequence" is intended to include promoters, repressor binding sites, activator binding sites, enhancers and other expression control elements (e.g., terminators, polyadenylation signals, or other elements of mRNA secondary structure). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-, tet-, lpp-, lac-, lpp lac-, lacIq-, T7-, T5-, T3-, gal-, trc-, ara-, SP6-, arny, SP02, e-Pp-ore PL, which are used preferably in bacteria. Additional regulatory sequences are, for example, promoters from yeasts and fungi, such as ADC1, MFa, AC, P-60, CYC1, GAPDH, TEF, rp28, ADH, promoters from plants such asCaMV/35S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids in accordance with the invention.

The recombinant expression vectors of the invention can be designed for expression of the polypeptides in accordance with the invention in prokaryotic or eukaryotic cells. For example, the genes for the enzymes of Group I can be expressed in bacterial cells such as *C. glutamicum* and *E. coli*, insect cells (using baculovirus expression vectors), yeast and other fungal cells (see Romanos, M. A. et al. (1992), *Yeast* 8: 423-488; van den Hondel, C. A. M. J. J. et al. (1991) in: More Gene Manipulations in Fungi, J. W. Bennet & L. L. Lasure, eds., p. 396-428: Academic Press: San Diego; and van den Hondel, C. A. M. J. J. & Punt, P. J. (1991) in: Applied Molecular Genetics of Fungi, Peberdy, J. F. et al., eds., p. 1-28, Cambridge University Press: Cambridge), algae and multicellular plant cells (see Schmidt, R. and Willmitzer, L. (1988) *Plant Cell Rep.*: 583-586). Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins.

Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) Gene 67: 31-40), pMAL (New England Biolabs, Beverly, Mass.) and pRIT5 (Pharmacia, Piscataway, N.J.) which fuse glutathione S-transferase (GST), maltose E binding protein, or protein A, respectively.

Examples of suitable inducible non-fusion *E. coli* expression vectors include pTrc (Amann et al., (1988) Gene 69: 301-315), pLG338, pACYC184, pBR322, pUC18, pUC19, pKC30, pRep4, pHS1, pHS2, pPLc236, pMBL24, pLG200, pUR290, pIN-III113-Bl, egtll, pBdC1, and pET lld (Studier et al., Gene Expression Technology: Methods in Enzymology 185, Academic Press, San Diego, Calif. (1990) 60-89; and Pouwels et al., eds. (1985) Cloning Vectors. Elsevier: N.Y. IBSN 0 444 904018). Target gene expression from the pTrc vector relies on host RNA polymerase transcription from a hybrid trp-lac fusion promoter. Target gene expression from the pET lld vector relies on transcription from a T7 gnlO-lac fusion promoter mediated by a coexpressed viral RNA polymerase (T7gnl). This viral polymerase is supplied by host strains BL21 (DE3) or HMS174 (DE3) from a resident X prophage harboring a T7gnl gene under the transcriptional control of the lacUV 5 promoter. For transformation of other varieties of bacteria, appropriate vectors may be selected. For example, the plasmidspIJ101, pIJ364, pIJ702 and pIJ361 are known to be useful in transforming *Streptomyces*, while plasmids pUB110, pC194, or pBD214 are suited for transformation of *Bacillus* species. Several plasmids of use in the transfer of genetic information into *Corynebacterium* include pHM1519, pBL1, pSA77, or pAJ667 (Pouwels et al., eds. (1985) Cloning Vectors. Elsevier: N.Y. IBSN 0 444 904018).

One strategy to maximize recombinant protein expression is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992) *Nucleic Acids Res.* 20: 2111-2118). Such alteration of nucleic acid sequences of the invention can be carried out by standard DNA synthesis techniques.

Examples of suitable *C. glutamicum* and *E coli* shuttle vectors can be found in Eikmanns et al (*Gene*. (1991) 102, 93-8).

In another embodiment, the protein expression vector is a yeast expression vector. Examples of vectors for expression in yeast *S. cerevisiae* include pYepSec1 (Baldari, et al., (1987) *Embo J.* 6: 229-234), 2i, pAG-1, Yep6, Yepl3, pEM-BLYe23, pMFa (Kurjan and Herskowitz, (1982) *Cell* 30: 933-943), pJRY88 (Schultz et al., (1987) *Gene* 54: 113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) in: Applied Molecular Genetics of Fungi, J. F. Peberdy, et al., eds., p. 1-28, Cambridge University Press: Cambridge, and Pouwels et al., eds. (1985) Cloning Vectors. Elsevier: N.Y. (IBSN 0 444 904018).

For the purposes of the present invention, an operative link is understood to be the sequential arrangement of promoter, coding sequence, terminator and, optionally, further regulatory elements in such a way that each of the regulatory elements can fulfill its function, according to its determination, when expressing the coding sequence.

For other suitable expression systems for both prokaryotic and eukaryotic cells see chapters 16 and 17 of Sambrook, J. et al. Molecular Cloning: A Laboratory Manual. 3rd ed., Cold Spring Harbor Laboratory, Cold Spring Harbor Laboratory Press, Cold Spring Harbor, N.Y., 2003.

Another aspect of the invention pertains to organisms or host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e. g., linear DNA or RNA (e. g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (Molecular Cloning: A Laboratory Manual. 3rd ed., Cold Spring Harbor Laboratory, Cold Spring Harbor Laboratory Press, Cold Spring Harbor, N.Y., 2003), and other laboratory manuals.

In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding polypeptides of the present invention or can be introduced on a separate vector. Cells stably transfected with the introduced nucleic acid can be identified by drug selection (e. g., cells that have incorporated the selectable marker gene will survive, while the other cells die).

In another embodiment, recombinant microorganisms can be produced which contain selected systems which allow for regulated expression of the introduced gene. For example, inclusion of a nucleotide sequence of the present invention on a vector placing it under control of the lac operon permits expression of the gene only in the presence of IPTG. Such regulatory systems are well known in the art.

In one embodiment, the method comprises culturing the organisms of invention (into which a recombinant expression vector encoding e.g. a polypeptide of the present invention has been introduced, or into which genome has been introduced a gene encoding a wild-type or altered enzyme) in a suitable medium for methionine production. In another embodiment, the method further comprises isolating methionine from the medium or the host cell.

Growth of *Escherichia Coli* and *Corynebacterium Glutamicum*-Media and Culture Conditions The person skilled in the art is familiar with the cultivation of common microorganisms such as *C. glutamicum* and *E. coli*. Thus, a general teaching will be given below as to the cultivation of *C. glutamicum*. Corresponding information may be retrieved from standard textbooks for cultivation of *E. coli*.

*E. coli* strains are routinely grown in MB and LB broth, respectively (Follettie, M. T., Peoples, 0., Agoropoulou, C., and Sinskey, A J. (1993) *J. Bacteriol.* 175, 4096-4103). Minimal media for *E. coli* is M9 and modified MCGC (Yoshihama, M., Higashiro, K., Rao, E. A., Akedo, M., Shanabruch, W G., Follettie, M. T., Walker, G. C., and Sinskey, A. J. (1985) *J. Bacteriol.* 162, 591-507), respectively. Glucose may be added at a final concentration of 1%. Antibiotics may be added in the following amounts (micrograms per milliliter): ampicillin, 50; kanamycin, 25; nalidixic acid, 25. Amino acids, vitamins, and other supplements may be added in the following amounts: methionine, 9.3 mM; arginine, 9.3 mM; histidine, 9.3 mM; thiamine, 0.05 mM. *E. coli* cells are routinely grown at37 C, respectively.

Genetically modified *Corynebacteria* are typically cultured in synthetic or natural growth media. A number of different growth media for *Corynebacteria* are both well-known and readily available (Lieb et al. (1989) *Appl. Microbiol. Biotechnol.,* 32: 205-210; von der Osten et al. (1998) *Biotechnology Letters,* 11: 11-16; Patent DE 4,120,867; Liebl (1992) "The Genus *Corynebacterium*, in: The Procaryotes, Volume II, Balows, A. et al., eds. Springer-Verlag).

These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, ribose, lactose, maltose, sucrose, raffinose, starch or cellulose serve as very good carbon sources.

It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

The overproduction of methionine is possible using different sulfur sources. Sulfates, thiosulfates, sulfites and also more reduced sulfur sources like $H_2S$ and sulfides and derivatives can be used. Also organic sulfur sources like methyl mercaptan, thioglycolates, thiocyanates, and thiourea, sulfur containing amino acids like cysteine and other sulfur containing compounds can be used to achieve efficient methionine production. Formate may also be possible as a supplement as are other C1 sources such as methanol or formaldehyde. Particularly suited are methanethiol and its dimer dimethyldisulfide.

Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamine, folic acid, nicotinic acid, pantothenate and pyridoxine. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (Eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

All medium components should be sterilized, either by heat (20 minutes at 1.5 bar and 121 C) or by sterile filtration. The components can either be sterilized together or, if necessary, separately.

All media components may be present at the beginning of growth, or they can optionally be added continuously or batch wise. Culture conditions are defined separately for each experiment.

The temperature should be in a range between 15° C. and 45° C. The temperature can be kept constant or can be altered during the experiment. The pH of the medium may be in the range of 5 to 8.5, preferably around 7.0, and can be maintained by the addition of buffers to the media. An exemplary buffer for this purpose is a potassium phosphate buffer. Synthetic buffers such as MOPS, HEPES, ACES and others can alternatively or simultaneously be used. It is also possible to maintain a constant culture pH through the addition of NaOH or $NH_4OH$ during growth. If complex medium components such as yeast extract are utilized, the necessity for additional buffers may be reduced, due to the fact that many complex compounds have high buffer capacities. If a fermentor is utilized for culturing the microorganisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml shake flasks are used, filled with 10% (by volume) of the required growth medium. The flasks should be shaken on a rotary shaker (amplitude 25 mm) using a speed-range of 100-300'rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an OD600 of 0.5-1.5 using cells grown on agar plates, such as CM plates (10 g/1 glucose, 2.5 g/1 NaCl, 2 g/1 urea, 10 g/1 polypeptone, 5 g/1 yeast extract, 5 g/1 meat extract, 22 g/1 NaCl, 2 g/1 urea, 10 g/1 polypeptone, 5 g/1 yeast extract, 5 g/1 meat extract, 22 g/1 agar, pH 6.8 with 2M NaOH) that had been incubated at 30 C.

Inoculation of the media is accomplished by either introduction of a saline suspension of *C. glutamicum* cells from CM plates or addition of a liquid preculture of this bacterium.

The above culture and media conditions may also be applied for other host organisms such as *S. coel* and *T. maritima.*

What is claimed is:

1. An isolated polynucleotide which encodes a polypeptide comprising SEQ ID NO:2 with a mutation at position 33 wherein the polypeptide exhibits cobalamin-dependent methionine synthase activity.

2. The isolated polynucleotide of claim 1, wherein the polypeptide is SEQ ID NO:1 with a mutation at position 33.

3. The isolated polynucleotide of claim 1, wherein the polypeptide has a mutation in its homocysteine-binding domain.

4. The isolated polynucleotide of claim 1, wherein the polypeptide exhibits reduced product inhibition by methionine.

5. The isolated polynucleotide of claim 1, wherein the mutation is Methionine at position 33 is replaced by Glycine or Alanine.

6. The isolated polynucleotide of claim 1, wherein the polypeptide is SEQ ID NO: 19.

7. An expression vector comprising the polynucleotide of claim 1.

8. A host cell which comprises the polynucleotide of claim 1.

9. The host cell of claim 8, wherein the host cell is a microorganism selected from the group consisting of: *Corynebacterium glutamicum, Escherichia coli, Streptomyces coelicolor* and *Thermotoga maritima.*

10. The host cell of claim 8, wherein one or more endogenous genes of the host cell which encode cobalamin-dependent methionine synthetase is deleted or functionally disrupted.

11. The host cell of claim 8, wherein the amount and/or activity of at least one of the following nucleotide sequences selected from the group consisting of:

nucleotide sequence coding for aspartate kinase lysC,
nucleotide sequence coding for glycerine aldehyde-3-phosphate dehydrogenase gap,
nucleotide sequence coding for 3-phosphoglycerate kinase pgk,
nucleotide sequence coding for pyruvatecarboxylase pyc,
nucleotide sequence coding for triosephosphate isomerase tpi,
nucleotide sequence coding for homoserin-O-acetyltransferase metA,
nucleotide sequence coding for cystathione-gamma-synthase metB,
nucleotide sequence coding for cystathione-gamma-lyase metC,
nucleotide sequence coding for serin-hydroxymethyl transferase glyA,
nucleotide sequence coding for O-acetylhomoserine-sulfhydrylase metY,
nucleotide sequence coding for phosphoserine aminotransferase serC,
nucleotide sequence coding for phosphoserine-phosphatase serB,
nucleotide sequence coding for serine acetyltransferase cysE,
nucleotide sequence coding for homoserine-dehydrogenase hom,
nucleotide sequence coding for methionine synthase metE,
nucleotide sequence coding for phosphoadenosine-phosphosulfate-reductase cysH,
nucleotide sequence coding for sulfate adenylyl transferase-subunit I,
nucleotide sequence coding for CysN-sulfate adenylyl transferase-subunit 2,
nucleotide sequence coding for ferredoxin-NADP-reductase,
nucleotide sequence coding for ferredoxin,
nucleotide sequence coding for glucose-6-phosphate-dehydrogenase, and
nucleotide sequence coding for fructose-1-6-bisphosphatase is increased in comparison to the corresponding parent strain.

12. The host cell of claim 8, wherein the amount and/or activity of at least one of the following nucleotide sequences selected from the group consisting of:

nucleotide sequence coding for homoserine kinase thrB,
nucleotide sequence coding for threonine dehydratase ilvA,
nucleotide sequence coding for threonine synthase thrC,
nucleotide sequence coding for meso-diaminopimelate-D-dehydrogenase ddh,
nucleotide sequence coding for phosphoenolpyruvate carboxy kinase pck,
nucleotide sequence coding for glucose-6-phosphate-6-isomerase pgi,
nucleotide sequence coding for pyruvate-oxidase poxB,
nucleotide sequence coding for dihydrodipicolinate synthase dapA,
nucleotide sequence coding for dihydrodipicolinate reductase dapB,
nucleotide sequence coding for diaminopicolinate-decarboxylase lysA,
nucleotide sequence coding for glycosyl transferase and
nucleotide sequence coding for lactate hydrogenase is reduced in comparison to the corresponding parent strain.

13. A method of producing methionine which comprises a) cultivating the host cell of claim 8, and b) isolating the methionine.

14. A method of producing methionine which comprising:

a) transfecting the vector of claim 7 into a host cell, b) culturing the host cell, and c) optionally recovering the methionine.

* * * * *